US010626408B2

(12) United States Patent
Shoseyov et al.

(10) Patent No.: US 10,626,408 B2
(45) Date of Patent: Apr. 21, 2020

(54) COLLAGEN PRODUCING PLANTS AND METHODS OF GENERATING AND USING SAME

(71) Applicant: CollPlant Ltd., Ness Ziona (IL)

(72) Inventors: Oded Shoseyov, Karme Yosef (IL); Hanan Stein, Nes-Ziona (IL)

(73) Assignee: CollPlant Ltd., Rehovot (IL)

( * ) Notice: Subject to any disclaimer, the term of this patent is extended or adjusted under 35 U.S.C. 154(b) by 116 days.

(21) Appl. No.: 15/723,185

(22) Filed: Oct. 3, 2017

(65) Prior Publication Data

US 2018/0044692 A1 Feb. 15, 2018

Related U.S. Application Data

(60) Division of application No. 13/936,274, filed on Jul. 8, 2013, now Pat. No. 9,783,816, which is a division of application No. 13/541,880, filed on Jul. 5, 2012, now abandoned, which is a continuation of application No. 11/730,071, filed on Mar. 29, 2007, now Pat. No. 8,455,717, which is a continuation-in-part of application No. PCT/IL2005/001045, filed on Sep. 28, 2005.

(60) Provisional application No. 60/613,719, filed on Sep. 29, 2004.

(51) Int. Cl.
*C12N 15/82* (2006.01)
*C12N 9/02* (2006.01)
*C07K 14/78* (2006.01)
*C12P 21/02* (2006.01)

(52) U.S. Cl.
CPC .......... *C12N 15/8257* (2013.01); *C07K 14/78* (2013.01); *C12N 9/0071* (2013.01); *C12P 21/02* (2013.01); *C12Y 114/11002* (2013.01); *C12Y 114/11004* (2013.01)

(58) Field of Classification Search
CPC .............................. C12N 9/0071; C07K 14/78
See application file for complete search history.

(56) References Cited

U.S. PATENT DOCUMENTS

| | | | |
|---|---|---|---|
| 4,855,237 | A | 8/1989 | Morinaga et al. |
| 4,945,050 | A | 7/1990 | Sanford et al. |
| 5,316,931 | A | 5/1994 | Donson et al. |
| 5,593,859 | A | 1/1997 | Prockop et al. |
| 5,693,507 | A | 12/1997 | Daniell et al. |
| 6,617,431 | B1 | 9/2003 | Gruber et al. |
| 6,713,662 | B1 | 3/2004 | Karatzas et al. |
| 2002/0098578 | A1 | 7/2002 | Prockop et al. |
| 2002/0142391 | A1 | 10/2002 | Kivirikko et al. |
| 2004/0018592 | A1 | 1/2004 | Bell et al. |
| 2005/0059053 | A1 | 3/2005 | Fischer et al. |
| 2005/0172342 | A1 | 8/2005 | Karatzas et al. |
| 2007/0186312 | A1 | 8/2007 | Shoseyov et al. |
| 2012/0284817 | A1 | 11/2012 | Shoseyov et al. |
| 2013/0289243 | A1 | 10/2013 | Shoseyov et al. |

FOREIGN PATENT DOCUMENTS

| | | | |
|---|---|---|---|
| EP | 951537 | | 10/1999 |
| EP | 10168971.9 | | 7/2010 |
| EP | 2357241 | | 8/2011 |
| WO | WO 87/06261 | | 10/1987 |
| WO | WO 97/04123 | | 2/1997 |
| WO | WO 97/038710 | | 10/1997 |
| WO | WO 99/16890 | | 4/1999 |
| WO | WO 00/020612 | | 4/2000 |
| WO | WO 01/29242 | | 4/2001 |
| WO | WO 01/034647 | * | 5/2001 |
| WO | WO 01/34647 | | 5/2001 |
| WO | WO 02/099067 | | 12/2002 |
| WO | WO 03/066847 | | 8/2003 |
| WO | WO 2004/057001 | | 7/2004 |
| WO | WO 2004/058956 | | 7/2004 |
| WO | WO 2006/035442 | | 4/2006 |

OTHER PUBLICATIONS

Merle, C., et al. "Hydroxylated human homotrimeric collagen I in Agrobacterium tumefaciens-mediated transient expression and in transgenic tobacco plant." FEBS letters 515.1-3 (2002): 114-118. (Year: 2002).*

Olsen, David, et al. "Recombinant collagen and gelatin for drug delivery." Advanced drug delivery reviews 55.12 (2003): 1547-1567. (Year: 2003).*

Decision of Technical Board of Appeal, Appeal No. T1252/13-3.3.04 Dated Dec. 22, 2017 From the Boards of Appeal of the European Patent Office Re. Application No. 05789469.3. (21 Pages).

Examination Report dated Oct. 31, 2017 From the Seviço Publico Federal, Ministerio da Industria, Comercio Exterior e Serviços, Instituto Nacional da Propriedade Industrial do Brasil, INPI Re. Application No. PI0516303-0 and Its Machine Summary in English. (3 Pages).

Official Action dated Oct. 2, 2008 From the US Patent and Trademark Office Re. U.S. Appl. No. 11/730,071.

Advisory Action Before the Filing of an Appeal Brief dated Apr. 13, 2017 From the US Patent and Trademark Office Re. U.S. Appl. No. 13/936,274. (5 pages).

Appeal Dated Sep. 12, 2013 From the European Patent Office Re. Application No. 05789469.3.

Applicant-Initiated Interview Summary Dated May 11, 2017 From the US Patent and Trademark Office Re. U.S. Appl. No. 13/936,274. (4 pages).

Associate Report of Telephone Communication Dated May 25, 2012 From the Examiner of the Japanese Patent Office Re. 2007-534176.

(Continued)

*Primary Examiner* — Lee A Visone

(57) ABSTRACT

A method of producing collagen in a plant and plants producing collagen are provided. The method is effected by expressing in the plant at least one type of a collagen alpha chain in a manner enabling accumulation of the collagen alpha chain in a subcellular compartment devoid of endogenous P4H activity, thereby producing the collagen in the plant.

5 Claims, 10 Drawing Sheets

Specification includes a Sequence Listing.

(56) References Cited

OTHER PUBLICATIONS

Brief Communication (Letter From the Opponent) Dated Nov. 29, 2012 From the European Patent Office Re. Application No. 05789469.3.
Brief Communication Dated Feb. 4, 2016 From the European Patent Office Re. Application No. 10168971.9.
Communication of a Notice of Opposition Dated Sep. 6, 2017 From the European Patent Office Re. Application No. 14185576.7. (7 Pages).
Communication of a Notice of Opposition Dated Dec. 10, 2015 From the European Patent Office Re. Application No. 10168971.9.
Communication of a Notice of Opposition Dated Jun. 28, 2011 From the European Patent Office Re. Application No. 05789469.3.
Communication of Further Notices of Opposition Pursuant to Rule 79(2) EPC Dated Jan. 15, 2016 From the European Patent Office Re. Application No. 10168971.9.
Communication of Notices of Opposition (R. 79(1) EPC) Dated Jul. 8, 2011 From the European Patent Office Re. Application No. 05789469.3.
Communication of Notices of Opposition (R.79(1) EPC) Dated Feb. 4, 2016 From the European Patent Office Re. Application No. 10168971.9.
Communication of Notices of Opposition (R.79(1) EPC) Dated Oct. 6, 2017 From the European Patent Office Re. Application No. 14185576.7. (1 Page).
Communication of Notices of Opposition (R.79(1) EPC) Dated Jan. 15, 2016 From the European Patent Office Re. Application No. 10168971.9.
Communication Pursuant to Article 94(3) EPC dated Apr. 9, 2013 From the European Patent Office Re. Application No. 10168971.9.
Communication Pursuant to Article 94(3) EPC dated Jun. 9, 2008 From the European Patent Office Re. Application No. 05789469.3.
Communication Pursuant to Article 94(3) EPC dated Feb. 13, 2013 From the European Patent Office Re. Application No. 10181115.6.
Communication Pursuant to Article 94(3) EPC dated Jan. 15, 2016 From the European Patent Office Re. Application No. 14185576.7.
Communication Pursuant to Article 94(3) EPC dated Dec. 19, 2008 From the European Patent Office Re. Application No. 05789469.3.
Communication Pursuant to Article 94(3) EPC dated Mar. 19, 2012 From the European Patent Office Re. Application No. 10168971.9.
Communication Pursuant to Article 94(3) EPC dated Mar. 19, 2012 From the European Patent Office Re. Application No. 10181115.6.
Communication Pursuant to Article 94(3) EPC dated Aug. 21, 2012 From the European Patent Office Re. Application No. 10168971.9.
Communication Pursuant to Article 94(3) EPC dated Jan. 28, 2008 From the European Patent Office Re. Application No. 05789469.3.
Communication Pursuant to Article 94(3) EPC dated May 29, 2017 From the European Patent Office Re. Application No. 16171177.5. (4 Pages).
Communication Pursuant to Article 96(2) EPC dated Aug. 21, 2007 From the European Patent Office Re. Application No. 05789469.3.
Communication Pursuant to Rule 58 EPC or Rule 159 EPC dated Nov. 24, 2010 From the European Patent Office Re. Application No. 10168971.9.
Decision to Refuse a European Patent Application dated Apr. 28, 2014 From the European Patent Office Re. Application No. 10181115.6.
European Search Report and the European Search Opinion dated Jul. 8, 2011 From the European Patent Office Re. Application No. 10168971.9.
European Search Report and the European Search Opinion dated Sep. 14, 2016 From the European Patent Office Re. Application No. 16171177.5.
European Search Report and the European Search Opinion dated Apr. 24, 2015 From the European Patent Office Re. Application No. 14185576.7.
European Search Report and the European Search Opinion dated Jun. 24, 2011 From the European Patent Office Re. Application No. 10181115.6.
Examination Report dated Aug. 4, 2010 From the Instituto Mexicano de la Propriedad Industrial Re. Application No. MX/a/2007/003767.
Examination Report dated Apr. 5, 2011 From the Government of India, Patent Office Re. Application No. 1819/CHENP/2007.
Examination Report dated Nov. 5, 2010 From the Instituto Mexicano de la Propriedad Industrial Re. Application No. MX/a/2007/003767.
Examination Report dated Aug. 27, 2010 From the Government of India, Patent Office Re. Application No. 1819/CHENP/2007.
Examination Report dated Mar. 28, 2014 From the Government of India, Patent Office Re. Application No. 5239/CHENP/2011.
Examiner's Report dated Apr. 1, 2010 From the Australian Government, IP Australia Re. Application No. 2007201384.
Examiner's Report dated Jan. 4, 2011 From the Australian Government, IP Australia Re. Application No. 2007201384.
Examiner's Report dated Sep. 23, 2011 From the Australian Government, IP Australia Re. Application No. 2011211341.
Hearing Notice Dated Feb. 10, 2017 From the Government of India, Patent Office Re. Application No. 5239/CHENP/2011. (1 Page).
Interlocutory Decision in Opposition Proceedings (Art. 101(3)(a) and 106(2) EPC) Dated Mar. 22, 2013 From the European Patent Office Re. Application No. 05789469.3.
International Preliminary Report on Patentability dated Apr. 12, 2007 From the International Bureau of WIPO Re. Application No. PCT/IL2005/001045.
International Search Report dated Mar. 20, 2006 From the International Searching Authority Re. Application No. PCT/IL2005/001045.
Notice of Allowance dated Apr. 16, 2013 From the US Patent and Trademark Office Re. U.S. Appl. No. 11/730,071.
Office Action dated Feb. 1, 2012 From the Israeli Patent Office Re. Application No. 182320 and Its Translation Into English.
Office Action dated Aug. 3, 2009 From the Israeli Patent Office Re. Application No. 182320 and Its Translation Into English.
Office Action dated Aug. 23, 2010 From the Israeli Patent Office Re. Application No. 182320 and Its Translation Into English.
Official Action dated Jun. 2, 2008 From the US Patent and Trademark Office Re. U.S. Appl. No. 11/730,071.
Official Action dated Apr. 8, 2013 From the US Patent and Trademark Office Re. U.S. Appl. No. 13/541,880.
Official Action dated Jun. 17, 2010 From the US Patent and Trademark Office Re. U.S. Appl. No. 11/730,071.
Official Action dated Sep. 18, 2009 From the US Patent and Trademark Office Re. U.S. Appl. No. 11/730,071.
Official Action dated Feb. 22, 2010 From the US Patent and Trademark Office Re. U.S. Appl. No. 11/730,071.
Official Action dated Jan. 22, 2008 From the US Patent and Trademark Office Re. U.S. Appl. No. 11/730,071.
Official Action dated Jan. 30, 2017 From the US Patent and Trademark Office Re. U.S. Appl. No. 13/936,274. (12 pages).
Opposition Brief Dated Aug. 30, 2017 From the From the European Patent Office Re. Application No. 14185576.7. (11 Pages).
Order (No. 18/2017) Under Section 15 of the Patents Act, 1970 Dated Mar. 17, 2017 From the Government of India, Patent Office, Intellectual Property Building Re. Application No. 5239/CHENP/2011. (2 Pages).
Partial European Search Report dated Mar. 17, 2011 From the European Patent Office Re. Application No. 10181115.6.
Partial European Search Report dated Jan. 23, 2015 From the European Patent Office Re. Application No. 14185576.7.
Provision of the Minutes in Accordance With Rule 124(4) EPC Dated Mar. 22, 2013 From the European Patent Office Re. Application No. 05789469.3.
Provision of the Minutes in Accordance With Rule 124(4) EPC dated Apr. 25, 2014 From the European Patent Office Re. Application No. 10181115.6.
Requisition dated Jun. 8, 2012 From the Canadian Intellectual Property Office Re. Application No. 2,582,051.
Requisition dated May 16, 2013 From the Canadian Intellectual Property Office Re. Application No. 2,582,051.
Requisition dated Feb. 21, 2014 From the Canadian Intellectual Property Office Re. Application No. 2,582,051.
Restriction Official Action dated May 23, 2016 From the US Patent and Trademark Office Re. U.S. Appl. No. 13/936,274.

(56) References Cited

OTHER PUBLICATIONS

Restriction Official Action dated Aug. 30, 2012 From the US Patent and Trademark Office Re. U.S. Appl. No. 13/541,880.
Summons to Attend Oral Proceedings Pursuant to Rule 115(1) EPC Dated Jan. 3, 2017 From the European Patent Office Re. Application No. 10168971.9. (13 Pages).
Summons to Attend Oral Proceedings Pursuant to Rule 115(1) EPC Dated Jan. 21, 2014 From the European Patent Office Re. Application No. 10181115.6.
Summons to Attend Oral Proceedings Pursuant to Rule 115(1) EPC Dated Jun. 28, 2016 From the European Patent Office Re. Application No. 05789469.3.
Summons to Attend Oral Proceedings Pursuant to Rule 115(1) EPC Dated Jul. 30, 2012 From the European Patent Office Re. Application No. 05789469.3.
Summons to Attend Oral Proceedings Pursuant to Rule 115(1) EPC Dated Oct. 31, 2013 From the European Patent Office Re. Application No. 10181115.6.
Translation of Notice of Reason for Rejection dated Sep. 2, 2011 From the Japanese Patent Office Re. Application No. 2007-534176.
Translation of Notice of Reason for Rejection dated May 7, 2013 From the Japanese Patent Office Re. Application No. 2011-259678.
Translation of Notice of Reason for Rejection dated May 10, 2011 From the Japanese Patent Office Re. Application No. 2007-534176.
Translation of Office Action dated Aug. 7, 2009 From the State Intellectual Property Office of the People's Republic of China Re.: Application No. 200580040821.7.
Translation of Office Action dated Aug. 16, 2010 From the State Intellectual Property Office of the People's Republic of China Re.: Application No. 200580040821.7.
Written Opinion dated Mar. 20, 2006 From the International Searching Authority Re. Application No. PCT/IL2005/001045.
Written Opinion dated Apr. 23, 2008 From the Intellectual Property Office of Singapore Issued by Australian Government, IP Australia Re.: Application No. SG 200702377-3.
Bulleid et al. "Recombinant Expression Systems for the Production of Collagen", Biochemical Society Transactions, 28(4): 350-353, 2000.
Dawson et al. "A Tobacco Mosaic Virus-Hybrid Expresses and Loses an Added Gene", Virology, 172: 285-292, 1989.
French et al. "Bacterial Gene Inserted in an Engineered RNA Virus: Efficient Expression in Monocotyledonous Plant Cells", Science, 231: 1294-1297, Mar. 14, 1986.
Fromm et al. "Stable Tranformation of Maize After Gene Transfer by Electroporation", Nature, 319: 791-793, Feb. 27, 1986.
Galili et al. "The 5' Leader Sequence of Tobacco Mosaic Virus RNA Enhances the Expression of Foreign Gene Transcripts In Vitro and In Viivo", Nucleic Acids Research, 15(8): 3257-3273, 1987.
Gatenby "Regulation and Expression of Plant Genes in Microorganisms", Plant Biotechnology, Chap.5: 93-112, 1989.
Han et al. "Segregation of Type I Collagen Homo- and Heterotrimers in Fibrils", Journal of Molecular Biology, 383(1): 122-132, Oct. 31, 2008.
Hare et al. "Metabolic Implications of Stress-Induced Proline Accumulation in Plants", Plant Growth Regulation, 21: 79-102, 1997.
Hieta et al. "Cloning and Characterization of a Low Molecular Weight Prolyl 4-Hydroxylase From *Arabidopsis thaliana*", The Journal of Biological Chemistry, XP002368907, 277(26): 23965-23971, Jun. 28, 2002.
Horsch et al. "Leaf Disc Transformation", Plant Molecular Biological Manual, A5: 1-9, 1988.
Horvath et al. "The Production of Recombinant Proteins in Transgenic Barley Grains", Proc. Natl. Acad. Sci. USA, XP002173225, 97(4): 1914-1919, Feb. 15, 2000. p. 1917, r-h Col.
Hulmes "Building Collagen Molecules, Fibrils, and Suprafibrillar Structures", Journal of Structurural Biology, XP002626609, 137(1-2): 2-10, 2002.
Inkinen "Connective Tissue Formation in Wound Healing. An Experimental Study", Academic Dissertation, University of Helsinki, Faculty of Science, Department of Biosciences, Division of Biochemistry, Sep. 2003.
Jiang et al. "Membrane Anchors for Vacuolar Targeting: Application in Plant Bioreactors", Trends in Biotechnology, XP004335891, 20(3): 99-102, Mar. 1, 2002.
Kivirikko Declaration of Professor Kivirikkco, MD, PhD, 5 P., Dec. 2013.
Klee et al. "Agrobacterium Tranformation System", In: 'Cell Culture and Somatic Cell Genetics', Molecular Biology of Plant Nuclear Genes, 6(Chap.1): 2-23, 1989.
Klee et al. "Agrobacterium-Mediated Plants Transformation and Its Further Applications to Plant Biology", Annual Review of Plant Physiology, 38: 467-486, 1987.
Klein et al. "Factors Influencing Gene Delivery Into *Zea mays* Cells by High-Velocity Microprojectiles", Bio/Technology, 6: 559-563, May 1988.
Laemmli "Cleavage of Structural Proteins During the Assembly of the Head of Bacteriophage T4", Nature, 227: 680-685, Aug. 15, 1970.
Maijsterek et al "Prospects and Limitations of the Rational Engineering of Fibrillar Collagens", Protein Science, 12: 2063-2072, 2003.
Marttila et al. "A Barley (*Hordeum vulgare* L.) LEA3 Protein, HVA1, Is Abundant in Protein Storage Vacuoles", Planta, 199: 602-611, 1996.
Marty "Plant Vacuoles", Plant Cell, XP002640272, 11(4): 587-599, Apr. 1999.
Matsuoka et al. "Cis-Elements of Protein Transport to the Plant Vacuoles", Journal of Experimental Botany, XP001188956, 50(331): 165-174, Feb. 1, 1999.
McCabe et al. "Stable Transformation of Soybean (*Glycine max*) by Particle Acceleration", Bio/Technology, 6: 923-926, Aug. 1988.
Merle et al. "Hydroxylated Human Homotrimeric Collagen I in Agrobacterium Tumefaciens-Mediated Transient Expression and in Transgenic Tobacco Plant", FEBS Letters, XP004347752, 515(1-3): 114-118, Mar. 27, 2002.
Miles et al. "The Role of the Alpha2 Chain in the Stabilization of the Collagen Type I Heterotrimer: A Study of the Type I Homotrimer in Oim Mouse Tissues", Journal of Molecular Biology, 321(5): 797-805, Aug. 30, 2002.
Nakamura et al. "Protein Targeting to the Vacuole in Plant Cells", Plant Physiology, XP002038306, 101(1): Jan. 1-5, 1993.
Neuhaus et al. "Plant Transformation by Microinjection Techniques", Physiologia Plantarum, 79: 213-217, 1990.
Neuhaus et al. "Sorting of Proteins to Vacuoles in Plant Cells", Plant Molecular Biology, 38: 127-144, 1998.
Neuhaus et al. "Transgenic Rapeseed Plants Pbtained by the Microinjection of DNA Into Microspore-Derived Embryoids", Theoretical and Applied Genetics, 75: 30-36, 1987.
Niemes et al. "Sorting of Plant Vacuolar Proteins Is Initiated in the ER", The Plant Journal, 62(4): 601-614, May 2010.
Nokelainen "Recombinant Human Collagens. Characterization of Type II Collagen Expressed in Insect Cells and Production of Types I-III Collagen in the Yeast Pichia Pastoris", Collagen Research Unit, Biocenter Oulu and Department of Mediical Biochemistry, University of Oulu, Finland, 70 P., Aug. 10, 200.
Nokelainen et al. "High-Level Production of Human Type I Collagen in the Yeast *Pichia pastoris*", Yeast, XP008068378, 18: 797-806, Jan. 1, 2011. Table I.
Ohta "High-Efficiency Genetic Transformation of Maize by a Mixture of Pollen and Exogenous DNA", Proc. Natl. Acad. Sci. USA, 83: 715-719, Feb. 1986.
Olsen et al. "Production of Human Type I Collagen in Yeast Reveals Unexpected New Insights Into the Molecular Assembly of Collagen Trimers", The Journal of Biological Chemistry, XP002969135, 276(26): 24038-24043, Jun. 29, 2001. Figs.1, 4, Table 1.
Olsen et al. "Recombinant Collagen and Gelatin for Drug Delivery", Advanced Drug Delivery Reviews, XP002368792, 55(12): 1547-1567, Nov. 28, 2003. p. 1553, 1-h Col.—p. 1554, r-h Col.

(56) References Cited

OTHER PUBLICATIONS

Osorio "Development of Transgenic Barley Expressing Human Type I Collagen", Thesis for the Degree of Master of Science in Crop Science, Washington State University, 132 P., Dec. 2004.
Perret et al "Unhydroxylated Triple-Helical Collagen 1 Produced in Transgenic Plants Provides New Clues on the Role of Hydroxyproline in Collagen Folding and Fibril Formation", The Journal of Biological Chemistry, 276(47): 43693-43698, Nov. 23, 2001.
Perret et al. "Prolyl Hydroxylation of Collagen Type I Is Required for Efficient Binding to Integrin Alpha1Beta1 and the Platelet Glycoprotein VI But Not to Alpha2Beta1", The Journal of Biological Chemistry, XP002626606, 278(32): 29873-29879, Aug. 8, 2003.
Ritala et al "Production of a Recombinant Industrial Protein Using Barley Cell Cultures", Protein Expression and Purification, 59: 274-281, 2008.
Ruggiero et al. "Triple Helix Assembly and Processing of Human Collagen Produced in Transgenic Tobacco Plants", FEBS Letters, XP004261062, 469(1): 132-136, Mar. 3, 2000. p. 136, 1-h Col.
Sanford "Biolistic Plant Transformation", Physiologia Plantarum, 79: 206-209, 1990.
Shimamoto et al. "Fertile Transgenic Rice Plants Regenerated From Transformed Protoplasts", Nature, 338: 274-276, Mar. 16, 1989.
Shoseyov et al. Replacement Drawings: Clearer Version of Patent's Figures From a Corresponding US Application 2007/0186312.
Stein et al. "Production of Bioactive, Post-Translationally Modified, Heterotrimeric, Human Recombinant Type-I Collagen in Transgenic Tobacco", Biomacromolecules, 10(9): 2640-2645, Aug. 14, 2009.
Stephan et al. "Expression and Supramolecular Assembly of Recombinant [Alpha]1(VIII) and [Alpha]2(VIII) Collagen Homotrimers", The Journal of Biological Chemistry, XP002626607, 279(20): 21469-21477, May 14, 2004. p. 21470.
Takamatsu et al. "Expression of Bacterial Chloramphenicol Acetyltransferase Gene in Tobacco Plants Mediated by TMV-RNA", The EMBO Journal, 6(2): 307-311, 1987.
Takamatsu et al. "Production of Enkephalin in Tobacco Protoplasts Using Tobacco Mosaic Virus RNA Vector", FEBS Letters, 269: 73-76, 1990. Abstract.
Tanaka et al. "Plant Prolyl Hydroxylase Recognizes Poly(L-Proline) II Helix", Journal of Biological Chemistry, 256(22): 11397-11400, 1981.
Toman et al. "Production of Recombinant Human Type I Procollagen Homotrimer in the Mammary Gland of Transgenic Mice", Transgenic Research, XP002626608, 8(6): 415-427, Dec. 1999. p. 416, r-h Col., Figs.1, 5.
Toriyama et al. "Transgenic Rice Plants After Direct Gene Transfer Into Protoplasts", Bio/Technology, 6: 1072-1074, 1988.
Turpeenniemi-Hujanen et al. "Concomitant Hydroxylation of Proline and Lysine Residues in Collagen Using Purified Enzymes In Vitro", Biochimica et Biophysica Acta, 800(1): 59-65, 1984.
Veijola et al. "Cloning, Baculovirus Expression, and Characterization of the a Subunit of Prolyl 4-Hydroxylase from the Nematode Caenorhabditis Elegans", The Journal of Biochemistry, 269(43): 26746-26753, Oct. 28, 1994.
Vuorela et al. "Assembly of Human Prolyl 4-Hydroxylase and Type III Collagen in the Yeast Pichia Pastoris: Formation of a Stable Enzyme Tetramer Requires Coexpression With Collagen and Assembly of a Stable Collagen Requires Coexpression With Prolyl 4-Hydroxylase", The EMBO Journal, XP002153732, 16(22): 6702-6712, 1997.
Wang et al. "The Third Activity for Lysyl Hydroxylase 3: Galactosylation of Hydroxylysyl Residues in Collagens In Vitro", Matrix Biology, XP002368908, 21(7): 559-566, Nov. 2002.
Wong Po Foo et al. "Genetic Engineering of Fibrous Proteins: Spider Dragline Silk and Collagen", Advanced Drug Delivery Reviews, 54(8): 1131-1143, Oct. 18, 2002.
Yoshida et al. "The Plant Vesicular Transport Engineering for Production of Useful Recombinant Proteins", Journal of Molecular Catalysis B: Enzymatic, XP002640279, 28(4-6); 167-171, Jun. 1, 2004. Fig.1, Tables 1-3.
Zhang et al "Purification and Characterization of a 44-kDa Recombinant Collagen I Alpha 1 Fragment From Corn Grain", Journal of Agricultural and Food Chemistry, 57: 880-887, 2009.
Zhang et al. "Transgenic Rice Plants Produced by Electroporation-Mediated Plasmid Uptake Into Protoplasts", Plant Cell Reports, 7: 379-384, 1988.
Communication Pursuant to Article 94(3) EPC dated Nov. 20, 2018 From the European Patent Office Re. Application No. 17205280.5. (3 Pages).
Communication Pursuant to Article 94(3) EPC dated Jan. 15, 2018 From the European Patent Office Re. Application No. 16171177.5. (4 Pages).
European Search Report and the European Search Opinion dated Jan. 29, 2018 From the European Patent Office Re. Application No. 17205280.5. (11 Pages).
Communication Pursuant to Article 94(3) EPC dated Jun. 11, 2018 From the European Patent Office Re. Application No. 16171177.5. (4 Pages).
Communication Pursuant to Article 94(3) EPC dated Sep. 13, 2018 From the European Patent Office Re. Application No. 16171177.5. (3 Pages).
Decision Revoking the European Patent (Art. 101(2) EPC) Dated Jun. 15, 2018 From the European Patent Office Re. Application No. 14185576.7. (6 Pages).

* cited by examiner

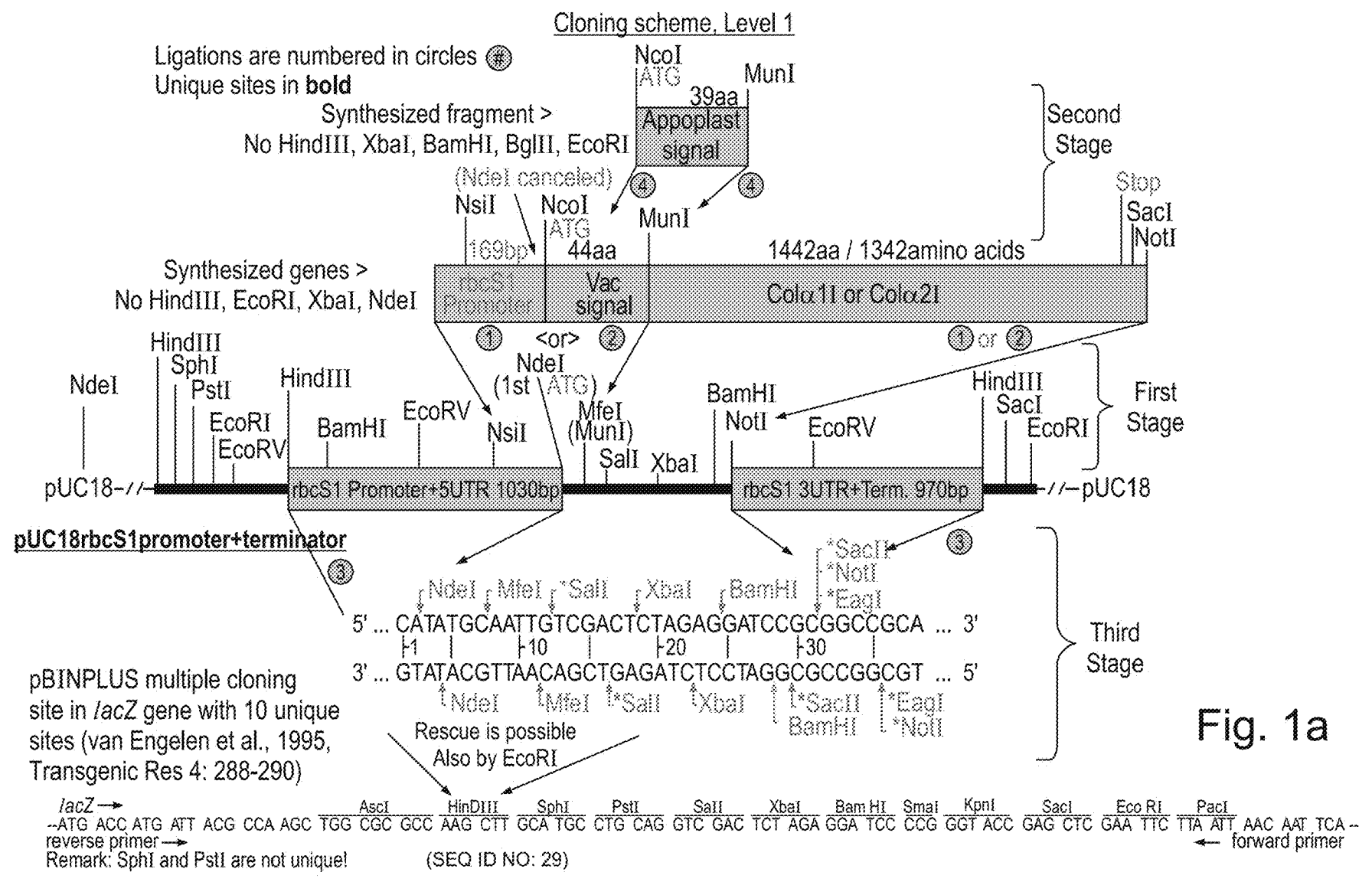

Cloning scheme, Level 1

Ligations are numbered in circles (#)
Unique sites in bold

Synthesized fragment >
No HindIII, XbaI, BamHI, BglII, EcoRI

NcoI
ATG
39aa
MunI
Appoplast signal
(4)
(4)

Second Stage (NdeI canceled)
NsiI
NcoI
ATG
MunI
169bp
44aa
1442aa / 1342amino acids
Stop
SacI
NotI Synthesized genes >
No HindIII, EcoRI, XbaI, NdeI rbcS1 Promoter
Vac signal
Colα1I or Colα2I (1) <or> (2)
(1) or (2)

NdeI
HindIII
SphI
PstI
EcoRI
EcoRV
HindIII
BamHI
EcoRV
NsiI
NdeI (1st ATG)
MfeI (MunI)
SalI
XbaI
BamHI
NotI
EcoRV
HindIII
SacI
EcoRI First Stage pUC18–//– rbcS1 Promoter+5UTR 1030bp rbcS1 3UTR+Term. 970bp –//–pUC18 pUC18rbcS1promoter+terminator

(3)
(3)

NdeI MfeI *SalI XbaI BamHI *SacII *NotI *EagI

5' ... CATATGCAATTGTCGACTCTAGAGGATCCGCGGCCGCA ... 3'
1 10 20 30
3' ... GTATACGTTAACAGCTGAGATCTCCTAGGCGCCGGCGT ... 5'

NdeI MfeI *SalI XbaI BamHI *SacII *EagI *NotI

Third Stage pBINPLUS multiple cloning site in *lacZ* gene with 10 unique sites (van Engelen et al., 1995, Transgenic Res 4: 288-290)

Rescue is possible
Also by EcoRI

Fig. 1a

*lacZ* →

AscI HinDIII SphI PstI SalI XbaI Bam HI SmaI KpnI SacI Eco RI PacI

--ATG ACC ATG ATT ACG CCA AGC TGG CGC GCC AAG CTT GCA TGC CTG CAG GTC GAC TCT AGA GGA TCC CCG GGT ACC GAG CTC GAA TTC TTA ATT AAC AAT TCA -- reverse primer →

← forward primer

Remark: SphI and PstI are not unique!

(SEQ ID NO: 29)

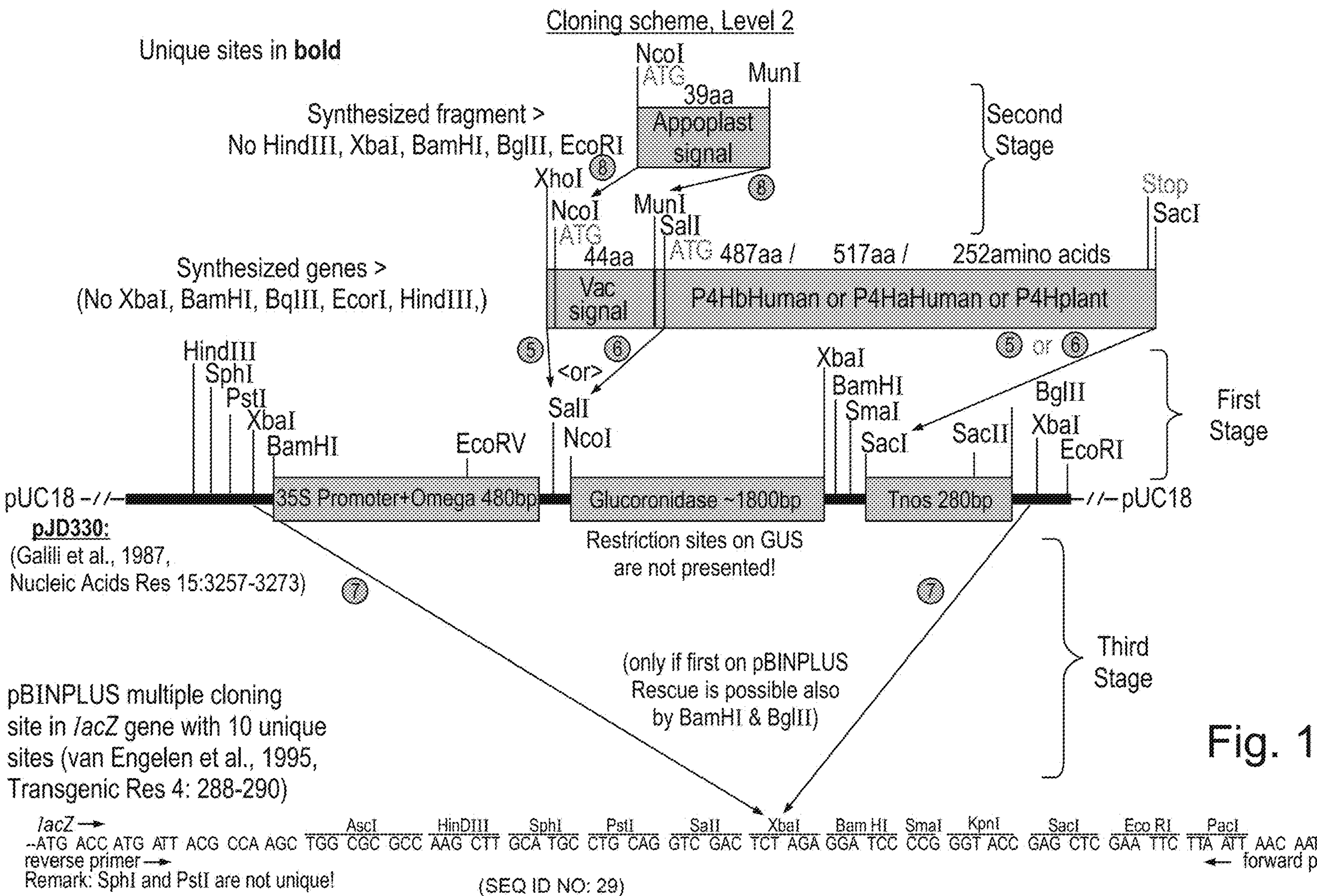
Cloning scheme, Level 2
Unique sites in bold
Synthesized fragment >
No HindIII, XbaI, BamHI, BglII, EcoRI
NcoI
ATG
39aa
MunI
Appoplast signal
8
Second Stage
XhoI
NcoI
ATG
44aa
MunI
SalI
ATG
487aa / 517aa / 252amino acids
Stop
SacI
Synthesized genes >
(No XbaI, BamHI, BqlII, EcorI, HindIII,)
Vac signal
P4HbHuman or P4HaHuman or P4Hplant
5
6
5 or 6
<or>
HindIII
SphI
PstI
XbaI
BamHI
EcoRV
SalI
NcoI
XbaI
BamHI
SmaI
SacI
SacII
BglII
XbaI
EcoRI
First Stage
pUC18
35S Promoter+Omega 480bp
Glucoronidase ~1800bp
Tnos 280bp
pUC18
pJD330:
(Galili et al., 1987,
Nucleic Acids Res 15:3257-3273)
Restriction sites on GUS are not presented!
7
Third Stage
(only if first on pBINPLUS
Rescue is possible also
by BamHI & BglII)
pBINPLUS multiple cloning
site in *lacZ* gene with 10 unique
sites (van Engelen et al., 1995,
Transgenic Res 4: 288-290)
Fig. 1b
*lacZ*
AscI HinDIII SphI PstI SalI XbaI Bam HI SmaI KpnI SacI Eco RI PacI
--ATG ACC ATG ATT ACG CCA AGC TGG CGC GCC AAG CTT GCA TGC CTG CAG GTC GAC TCT AGA GGA TCC CCG GGT ACC GAG CTC GAA TTC TTA ATT AAC AAT TCA --
reverse primer
forward primer
Remark: SphI and PstI are not unique!
(SEQ ID NO: 29)

COLLAGEN PRODUCING PLANTS AND METHODS OF GENERATING AND USING SAME

RELATED APPLICATIONS

This application is a division of U.S. patent application Ser. No. 13/936,274 filed on Jul. 8, 2013, which is a division of U.S. patent application Ser. No. 13/541,880 filed on Jul. 5, 2012, which is a continuation of U.S. patent application Ser. No. 11/730,071 filed on Mar. 29, 2007, now U.S. Pat. No. 8,455,717, which is a continuation-in-part (CIP) of PCT Patent Application No. PCT/IL2005/001045 having International Filing Date of Sep. 28, 2005, which claims the benefit of priority of U.S. Provisional Patent Application No. 60/613,719 filed on Sep. 29, 2004. The contents of the above applications are all incorporated by reference as if fully set forth herein in their entirety.

SEQUENCE LISTING STATEMENT

The ASCII file, entitled 71282SequenceListing.txt, created on Oct. 3, 2017, comprising 142,455 bytes, submitted concurrently with the filing of this application is incorporated herein by reference.

FIELD AND BACKGROUND OF THE INVENTION

The present invention relates to collagen producing plants and methods of generating and using same. More particularly, the present invention relates to a novel approach for generating plants capable of producing high levels of hydroxylated collagen chains which are capable of forming native triple helix type I collagen fibers.

Collagens are the main structural proteins responsible for the structural integrity of vertebrates and many other multicellular organisms. Type I collagen represents the prototypical fibrillar collagen and is the major collagen type in most tissues.

Type I collagen is the predominant collagen component of bone and tendon and is found in large amounts in skin, aorta, and lung. Type I collagen fibers provide great tensile strength and limited extensibility. The most abundant molecular form of type I collagen is a heterotrimer composed of two different alpha chains [alpha 1(I)]$_2$ and alpha 2(I) (Inkinen, 2003). All fibrillar collagen molecules contain three polypeptide chains constructed from a repeating Gly-X-Y triplet, where X and Y can be any amino acid but are frequently the imino acids proline and hydroxyproline.

Fibril forming collagens are synthesized as precursor procollagens containing globular N- and C-terminal extension propeptides. The biosynthesis of procollagen is a complex process involving a number of different post-translational modifications including proline and lysine hydroxylation, N-linked and O-linked glycosylation and both intra- and inter-chain disulphide-bond formation. The enzymes carrying out these modifications act in a coordinated fashion to ensure the folding and assembly of a correctly aligned and thermally stable triple-helical molecule.

Each procollagen molecule assembles within the rough endoplasmic reticulum from the three constituent polypeptide chains. As the polypeptide chain is co-translationally translocated across the membrane of the endoplasmic reticulum, hydroxylation of proline and lysine residues occurs within the Gly-X-Y repeat region. Once the polypeptide chain is fully translocated into the lumen of the endoplasmic reticulum the C-propeptide folds. Three pro-alpha chains then associate via their C-propeptides to form a trimeric molecule allowing the Gly-X-Y repeat region to form a nucleation point at its C-terminal end, ensuring correct alignment of the chains. The Gly-X-Y region then folds in a C-to-N direction to form a triple helix.

The temporal relationship between polypeptide chain modification and triple-helix formation is crucial as hydroxylation of proline residues is required to ensure stability of the triple helix at body temperature, once formed, the triple helix no longer serves as a substrate for the hydroxylation enzyme. The C-propeptides (and to a lesser extent the N-propeptides) keep the procollagen soluble during its passage through the cell (Bulleid et al., 2000). Following or during secretion of procollagen molecules into the extracellular matrix, propeptides are removed by procollagen N- and C-proteinases, thereby triggering spontaneous self-assembly of collagen molecules into fibrils (Hulmes, 2002). Removal of the propeptides by procollagen N- and C-proteinases lowers the solubility of procollagen by >10000-fold and is necessary and sufficient to initiate the self-assembly of collagen into fibers. Crucial to this assembly process are short non triple-helical peptides called telopeptides at the ends of the triple-helical domain, which ensure correct registration of the collagen molecules within the fibril structure and lower the critical concentration for self-assembly (Bulleid et al., 2000). In nature, the stability of the triple-helical structure of collagen requires the hydroxylation of prolines by the enzyme prolyl-4-hydroxylase (P4H) to form residues of hydroxyproline within a collagen chain.

Plants expressing collagen chains are known in the art, see for example, U.S. Pat. No. 6,617,431 and (Merle et al., 2002, Ruggiero et al., 2000). Although plants are capable of synthesizing hydroxyproline-containing proteins the prolyl hydroxylase that is responsible for synthesis of hydroxyproline in plant cells exhibits relatively loose substrate sequence specificity as compared with mammalian P4H and thus, production of collagen containing hydroxyproline only in the Y position of Gly-X-Y triplets requires plant co-expression of collagen and P4H genes (Olsen et al, 2003).

An attempt to produce human collagens that rely on the hydroxylation machinery naturally present in plants resulted in collagen that is poor in proline hydroxylation (Merle et al., 2002). Such collagen melts or loses its triple helical structure at temperatures below 30° C. Co-expression of collagen and prolyl-hydroxylase results with stable hydroxylated collagen that is biologically relevant for applications at body temperatures (Merle et al., 2002).

Lysyl hydroxylase (LH,EC 1.14.11.4), galactosyltransferase (EC 2.4.1.50) and glucosyltransferase (EC 2.4.1.66) are enzymes involved in posttranslational modifications of collagens. They sequentially modify lysyl residues in specific positions to hydroxylysyl, galactosylhydroxylysyl and glucosylgalactosyl hydroxylysyl residues. These structures are unique to collagens and essential for their functional activity (Wang et al, 2002). A single human enzyme, Lysyl hydroxylase 3 (LH3) can catalyze all three consecutive steps in hydroxylysine linked carbohydrate formation (Wang et al, 2002).

Hydroxylysins of a human collagen expressed in tobacco form less than 2% of the hydroxylysins found in a bovine collagen (0.04% of residues/1.88% of residues). This suggests that plant endogenic Lysyl hydroxylase is unable to sufficiently hydroxylate lysines in collagen.

While reducing the present invention to practice, the present inventors uncovered that efficient hydroxylation of collagen chains relies upon sequestering of the collagen chain along with an enzyme capable of correctly modifying this polypeptide.

SUMMARY OF THE INVENTION

According to one aspect of the present invention there is provided a method of producing collagen in a plant or an isolated plant cell comprising expressing in the plant or the isolated plant cell at least one type of a collagen alpha chain and exogenous P4H in a manner enabling accumulation of the at least one type of the collagen alpha chain and the exogenous P4H in a subcellular compartment devoid of endogenous P4H activity, thereby producing the collagen in the plant.

According to an additional aspect of the present invention there is provided According to further features in preferred embodiments of the invention described below, the method further comprises expressing exogenous LH3 in the subcellular compartment devoid of endogenous P4H activity.

According to still further features in the described preferred embodiments the at least one type of the collagen alpha chain includes a signal peptide for targeting to an apoplast or a vacuole.

According to still further features in the described preferred embodiments the at least one type of the collagen alpha chain is devoid of an ER targeting or retention sequence.

According to still further features in the described preferred embodiments the at least one type of the collagen alpha chain is expressed in a DNA-containing organelle of the plant.

According to still further features in the described preferred embodiments the exogenous P4H includes a signal peptide for targeting to an apoplast or a vacuole.

According to still further features in the described preferred embodiments the exogenous P4H is devoid of an ER targeting or retention sequence.

According to still further features in the described preferred embodiments the exogenous P4H is expressed in a DNA-containing organelle of the plant.

According to still further features in the described preferred embodiments the at least one type of the collagen alpha chain is alpha 1 chain.

According to still further features in the described preferred embodiments the at least one type of the collagen alpha chain is alpha 2 chain.

According to still further features in the described preferred embodiments the at least one type of the collagen alpha chain includes a C-terminus and/or an N-terminus propeptide.

According to still further features in the described preferred embodiments the plant is selected from the group consisting of Tobacco, Maize, Alfalfa, Rice, Potato, Soybean, Tomato, Wheat, Barley, Canola and Cotton.

According to still further features in the described preferred embodiments the at least one type of the collagen alpha chain or the exogenous P4H are expressed in only a portion of the plant.

According to still further features in the described preferred embodiments the portion of the plant is leaves, seeds, roots, tubers or stems.

According to still further features in the described preferred embodiments the exogenous P4H is capable of specifically hydroxylating the Y position of Gly-X-Y triplets of the at least one type of the collagen alpha chain.

According to still further features in the described preferred embodiments the exogenous P4H is human P4H.

According to still further features in the described preferred embodiments the plant is subjected to a stress condition.

According to still further features in the described preferred embodiments the stress condition is selected from the group consisting of drought, salinity, injury, cold and spraying with stress inducing compounds.

According to another aspect of the present invention there is provided a genetically modified plant or isolated plant cell capable of accumulating a collagen alpha chain having a hydroxylation pattern identical to that produced when the collagen alpha chain is expressed in human cells.

According to yet another aspect of the present invention there is provided a genetically modified plant or isolated plant cell capable of accumulating a collagen alpha chain in a subcellular compartment devoid of endogenous P4H activity.

According to still further features in the described preferred embodiments the genetically modified plant further comprises an exogenous P4H.

According to still further features in the described preferred embodiments the at least one type of the collagen alpha chain includes a signal peptide for targeting to an apoplast or a vacuole.

According to still further features in the described preferred embodiments the at least one type of the collagen alpha chain is devoid of an ER targeting or retention sequence.

According to still further features in the described preferred embodiments the at least one type of the collagen alpha chain is expressed in a DNA-containing organelle of the plant.

According to still further features in the described preferred embodiments the exogenous P4H includes a signal peptide for targeting to an apoplast or a vacuole.

According to still further features in the described preferred embodiments the exogenous P4H is devoid of an ER targeting or retention sequence.

According to still further features in the described preferred embodiments the exogenous P4H is expressed in a DNA-containing organelle of the plant.

According to still further features in the described preferred embodiments the collagen alpha chain is alpha 1 chain.

According to still further features in the described preferred embodiments the collagen alpha chain is alpha 2 chain.

According to still further features in the described preferred embodiments the collagen alpha chain includes a C-terminus and/or an N-terminus propeptide.

According to still another aspect of the present invention there is provided a plant system comprising a first genetically modified plant capable of accumulating a collagen alpha 1 chain and a second genetically modified plant capable of accumulating a collagen alpha 2 chain.

According to yet another aspect of the present invention there is provided a plant system comprising a first genetically modified plant capable of accumulating a collagen alpha 1 chain and a collagen alpha 2 chain and a second genetically modified plant capable of accumulating P4H.

According to still further features in the described preferred embodiments at least one of the first genetically modified plant and the second genetically modified plant further comprises exogenous P4H.

According to yet another aspect of the present invention there is provided a method of producing fibrillar collagen comprising: (a) expressing in a first plant a collagen alpha 1 chain; (b) expressing in a second plant a collagen alpha 2 chain, wherein expression in the first plant and the second plant the is configured such that the collagen alpha 1 chain and the collagen alpha 2 chain are each capable of accumulating in a subcellular compartment devoid of endogenous P4H activity; and (c) crossing the first plant and the second plant and selecting progeny expressing the collagen alpha 1 chain and the collagen alpha 2 chain thereby producing fibrillar collagen.

According to still further features in the described preferred embodiments the method further comprises expressing an exogenous P4H in each of the first plant and the second plant.

According to still further features in the described preferred embodiments each of the collagen alpha 1 chain and the collagen alpha 2 chain includes a signal peptide for targeting to an apoplast or a vacuole.

According to still further features in the described preferred embodiments each of the collagen alpha 1 chain and the collagen alpha 2 chain is devoid of an ER targeting or retention sequence.

According to still further features in the described preferred embodiments steps (a) and (b) are effected via expression in a DNA-containing organelle of the plant.

According to still further features in the described preferred embodiments the exogenous P4H includes a signal peptide for targeting to an apoplast or a vacuole.

According to still further features in the described preferred embodiments the exogenous P4H is devoid of an ER targeting or retention sequence.

According to still further features in the described preferred embodiments the exogenous P4H is expressed in a DNA-containing organelle of the plant.

According to still further features in the described preferred embodiments each of the collagen alpha 1 chain and the collagen alpha 2 chain includes a C-terminus and/or an N-terminus propeptide.

According to still further features in the described preferred embodiments the exogenous P4H is capable of specifically hydroxylating the Y position of Gly-X-Y triplets of the at least one type of the collagen alpha chain.

According to still further features in the described preferred embodiments the exogenous P4H is human P4H.

According to still further features in the described preferred embodiments the first plant and the second plant are subjected to a stress condition.

According to still further features in the described preferred embodiments the stress condition is selected from the group consisting of drought, salinity, injury, heavy metal toxicity and cold stress.

According to yet another aspect of the present invention there is provided a method of producing fibrillar collagen comprising: (a) expressing in a first plant a collagen alpha 1 chain and a collagen alpha 2 chain, wherein expression in the first plant is configured such that the collagen alpha 1 chain and the collagen alpha 2 chain are each capable of accumulating in a subcellular compartment devoid of endogenous P4H activity; (b) expressing in a second plant an exogenous P4H capable of accumulating in the subcellular compartment devoid of endogenous P4H activity; and (c) crossing the first plant and the second plant and selecting progeny expressing the collagen alpha 1 chain, the collagen alpha 2 chain and the P4H thereby producing fibrillar collagen.

According to yet another aspect of the present invention there is provided a nucleic acid construct comprising a polynucleotide encoding a human P4H positioned under the transcriptional control of a promoter functional in plant cells.

According to still further features in the described preferred embodiments the promoter is selected from the group consisting of the CaMV 35S promoter, the Ubiquitin promoter, the rbcS promoter and the SVBV promoter.

According to yet another aspect of the present invention there is provided a genetically modified plant or isolated plant cell being capable of expressing collagen alpha 1 chain, collagen alpha 2 chain, P4H, LH3 and protease C and/or protease N.

According to still further features in the described preferred embodiments the collagen alpha 1 chain and the collagen alpha 2 chain are each capable of accumulating in a subcellular compartment devoid of endogenous plant P4H activity.

According to yet another aspect of the present invention there is provided a genetically modified plant or isolated plant cell being capable of accumulating collagen having a temperature stability characteristic identical to that of mammalian collagen.

According to still further features in the described preferred embodiments the collagen is type I collagen.

According to still further features in the described preferred embodiments the mammalian collagen is human collagen.

According to yet another aspect of the present invention there is provided a collagen-encoding sequence optimized for expression in a plant.

According to still further features in the described preferred embodiments the collagen encoding sequence is as set forth by SEQ ID NO:1.

The present invention successfully addresses the shortcomings of the presently known configurations by providing a plant capable of expressing correctly hydroxylated collagen chains which are capable of assembling into collagen having properties similar to that of human collagen.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1*a-d* illustrate construction of various expression cassettes and vectors used to transform test plants. All of the coding sequences synthesized as a part of the present study were optimized for expression in tobacco. FIG. 1*a* shows a cloning scheme of type I collagen alpha I chain or type II collagen alpha 2 chain into a plant expression vector in accordance with some embodiments of the present invention; FIG. 1*b* shows a cloning scheme of the enzyme prolyl-4-hydroxylase (P4H) into a plant expression vector in accordance with some embodiments of the present invention; FIG. 1*c* shows a cloning scheme proteinase C or proteinase N into a plant expression vector in accordance with some embodiments of the present invention; FIG. 1*d* shows a cloning scheme of Lysyl hydroxylase 3 (LH3) into a plant expression vector in accordance with some embodiments of the present invention. A multiple cloning site set forth in SEQ ID NO: 29 is shown at the bottom of each panel.

In FIG. 6*a*—total soluble protein from tobacco 2-9 (expressing only col alpha1 and no P4H) and 3-5 (expressing both col alpha 1+2 and human P4H alpha and beta subunits) were subjected to heat treatment (15 minutes in 38° C. or 43° C.) followed by Trypsin digestion (20 minutes in R.T.) and tested with anti-Collagen I antibody in a Western blot procedure. Positive controls were samples of 500 ng human collagen I+total soluble proteins of w.t. tobacco. In FIG. 6*b*—total soluble proteins were extracted from transgenic tobacco 13-6 (expressing collagen I alpha 1 and alpha 2 chains—pointed by arrows, human P4H alpha and beta subunits and human LH3) and subjected to heat treatment (20 minutes in 33° C., 38° C. or 42° C.), immediately cooled on ice to prevent reassembly of triple helix and incubated with pepsin for 30 minutes in room temperature (about 22° C.) followed by testing with anti-Collagen I antibody ((# AB745 from Chemicon Inc.) in a standard Western blot procedure. Positive control was sample of ~50 ng human collagen I (# CC050 from Chemicon Inc., extracted from human placenta by pepsin digestion) which was added to total soluble proteins extracted from w.t. tobacco.

DESCRIPTION OF SPECIFIC EMBODIMENTS OF THE INVENTION

Figure 1C:
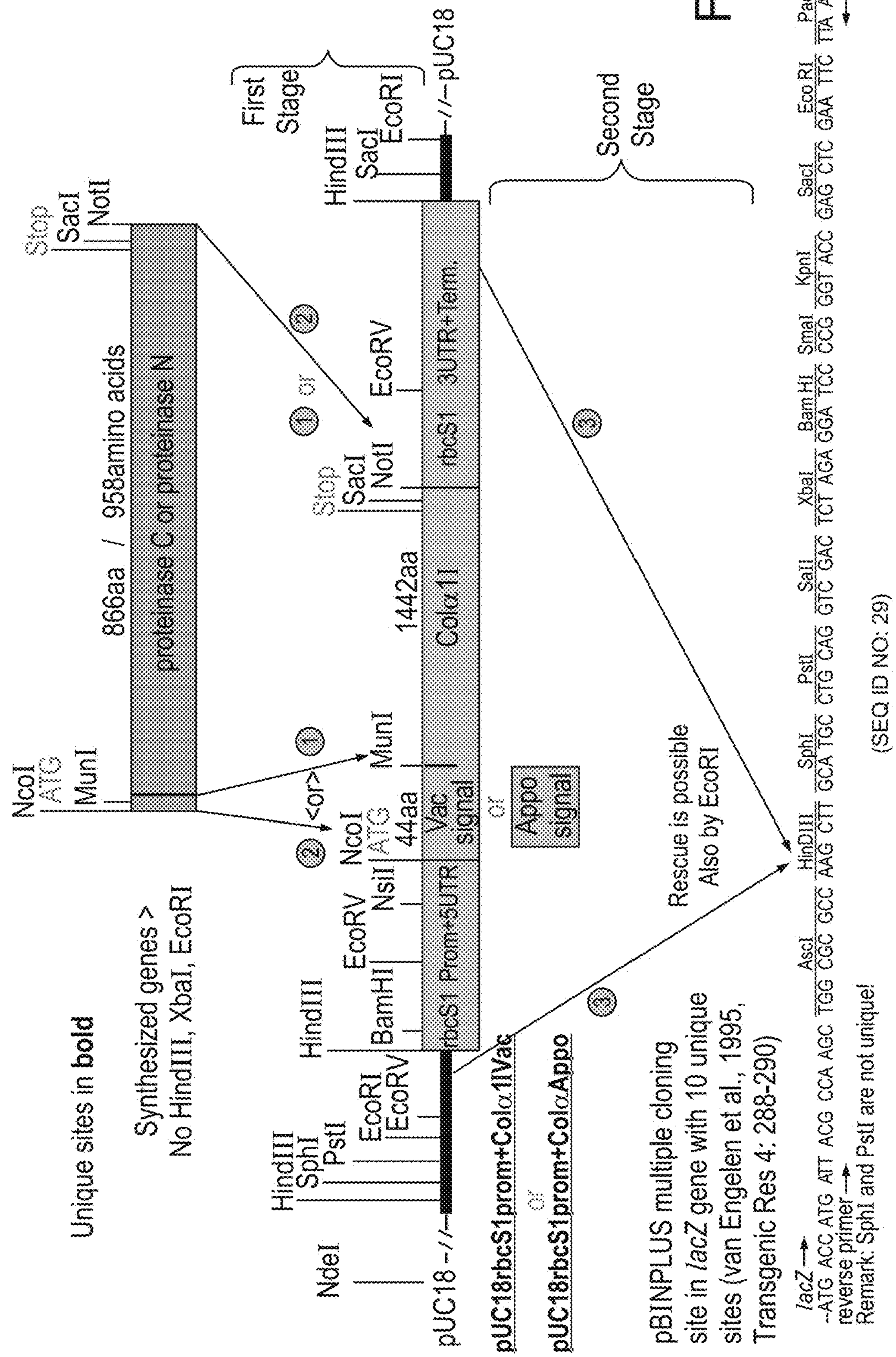

The present invention is of plants expressing and accumulating collagen which can be used to produce collagen and collagen fibers which display characteristics of mammalian collagen.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Collagen producing plants are known in the art. Although such plants can be used to produce collagen chains as well as collagen, such chains are incorrectly hydroxylated and thus self-assembly thereof, whether in planta or not, leads to collagen which is inherently unstable.

While reducing the present invention to practice, the present inventors have devised a plant expression approach which ensures correct hydroxylation of collagen chains and thus enables in-planta production of collagen which closely mimics the characteristics (e.g. temperature stability) of human type I collagen.

Thus, according to one aspect of the present invention there is provided a genetically modified plant which is capable of expressing at least one type of a collagen alpha chain and accumulating it in a subcellular compartment which is devoid of endogenous P4H activity.

As used herein, the phrase "genetically modified plant" refers to any lower (e.g. moss) or higher (vascular) plant or a tissue or an isolated cell thereof (e.g., of a cell suspension) which is stably or transiently transformed with an exogenous polynucleotide sequence. Examples of plants include Tobacco, Maize, Alfalfa, Rice, Potato, Soybean, Tomato, Wheat, Barley, Canola, Cotton, Carrot as well as lower plants such as moss.

As used herein, the phrase "collagen chain" refers to a collagen subunit such as the alpha 1 or 2 chains of collagen fibers, preferably type I fibers. As used herein, the phrase "collagen" refers to an assembled collagen trimer, which in the case of type I collagen includes two alpha 1 chains and one alpha 2 chain. A collagen fiber is collagen which is devoid of terminal propeptides C and N.

As is used herein, the phrase "subcellular compartment devoid of endogenous P4H activity" refers to any compartmentalized region of the cell which does not include plant P4H or an enzyme having plant-like P4H activity. Examples of such subcellular compartments include the vacuole, apoplast and cytoplasm as well as organelles such as the chloroplast, mitochondria and the like.

Any type of collagen chain can be expressed by the genetically modified plant of the present invention. Examples include Fibril-forming collagens (types I, II, III, V, and XI), networks forming collagens (types IV, VIII, and X), collagens associated with fibril surfaces (types IX, XII, and XIV), collagens which occur as transmembrane proteins (types XIII and XVII), or form 11-nm periodic beaded filaments (type VI). For further description please see Hulmes, 2002.

Preferably, the collagen chain expressed is an alpha 1 and/or 2 chain of type I collagen. The expressed collagen alpha chain can be encoded by any polynucleotide sequences derived from any mammal. Preferably, the sequences encoding collagen alpha chains are human and are set forth by SEQ ID NOs: 1 and 4.

Typically, alpha collagen chains expressed in plants may or may not include their terminal propeptides (i.e. propeptide C and propeptide N).

Ruggiero et al. (2000) note that processing of procollagen by plant proteolytic activity is different then normal processing in human and that propeptide C is removed by plant proteolytic activity although the cleavage site is unknown. Cleavage of the C propeptide may take place on a procollagen peptide before the assembly of trimmer (association of three C-Propeptides is essential for initiating the assembly of trimmers).

N-propeptide cleavage by plant proteolytic activity takes place in mature plants but not in plantlets. Such cleavage removes 2 amino acids from the N telopeptide (2 out of 17).

The C-propeptides (and to a lesser extent the N-propeptides) maintain the procollagen soluble during its passage through the animal cell (Bulleid et al., 2000) and are expected to have a similar effect in the plant cell. Following or during secretion of procollagen molecules into the extracellular matrix, propeptides are removed by procollagen N- and C-proteinases, thereby triggering spontaneous self-assembly of collagen molecules into fibrils (Hulmes, 2002). Removal of the propeptides by procollagen N- and C-proteinases lowers the solubility of procollagen by >10000-fold and is necessary and sufficient to initiate the self-assembly of collagen into fibers. Crucial to this assembly process are short non triple-helical peptides called telopeptides at the ends of the triple-helical domain, which ensure correct registration of the collagen molecules within the fibril structure and lower the critical concentration for self-assembly (Bulleid et al., 2000). Prior art describe the use of pepsin to cleave the propeptides during production of collagen (Bulleid et al 2000). However pepsin damages the telopeptides and as a result, pepsin-extracted collagen is unable to form ordered fibrillar structures (Bulleid et al 2000).

Protein disulfide isomerase (PDI) that form the beta subunit of human P4H was shown to bind to the C-propeptide prior to trimmer assembly thereby also acting as a molecular chaperone during chain assembly (Ruggiero et al, 2000).

The use of human Procollagen I N-proteinase and Procollagen C-proteinase expressed in a different plants may generate collagen that is more similar to the native human collagen and can form ordered fibrillar structures.

In a case where N or C propeptides or both are included in the expressed collagen chain, the genetically modified plant of the present invention can also express the respective protease (i.e. C or N or both). Polynucleotide sequences encoding such proteases are exemplified by SEQ ID NOs: 18 (protease C) and 20 (Protease N). Such proteases can be expressed such that they are accumulated in the same subcellular compartment as the collagen chain.

Accumulation of the expressed collagen chain in a subcellular compartment devoid of endogenous P4H activity can be effected via any one of several approaches.

For example, the expressed collagen chain can include a signal sequence for targeting the expressed protein to a subcellular compartment such as the apoplast or an organelle (e.g. chloroplast). Examples of suitable signal sequences include the chloroplast transit peptide (included in Swiss-Prot entry P07689, amino acids 1-57) and the Mitochondrion transit peptide (included in Swiss-Prot entry P46643, amino acids 1-28). The Examples section which follows provides additional examples of suitable signal sequences as well as guidelines for employing such signal sequences in expression of collagen chains in plant cells.

Alternatively, the sequence of the collagen chain can be modified in a way which alters the cellular localization of collagen when expressed in plants.

As is mentioned hereinabove, the ER of plants includes a P4H which is incapable of correctly hydroxylating collagen chains. Collagen alpha chains natively include an ER targeting sequence which directs expressed collagen into the ER where it is post-translationally modified (including incorrect hydroxylation). Thus, removal of the ER targeting sequence will lead to cytoplasmic accumulation of collagen chains which are devoid of post translational modification including any hydroxylations.

Example 1 of the Examples section which follows describes generation of collagen sequences which are devoid of ER sequences.

Still alternatively, collagen chains can be expressed and accumulated in a DNA containing organelle such as the chloroplast or mitochondria. Further description of chloroplast expression is provided hereinbelow.

As is mentioned hereinabove, hydroxylation of alpha chains is required for assembly of a stable type I collagen. Since alpha chains expressed by the genetically modified plant of the present invention accumulate in a compartment devoid of endogenous P4H activity, such chains must be isolated from the plant, plant tissue or cell and in-vitro hydroxylated. Such hydroxylation can be achieved by the method described by Turpeenniemi-Hujanen and Myllyla (Concomitant hydroxylation of proline and lysine residues in collagen using purified enzymes in vitro. Biochim Biophys Acta. 1984 Jul. 16; 800(1):59-65).

Although such in-vitro hydroxylation can lead to correctly hydroxylated collagen chains, it can be difficult and costly to achieve.

To overcome the limitations of in-vitro hydroxylation, the genetically modified plant of the present invention preferably also co-expresses P4H which is capable of correctly hydroxylating the collagen alpha chain(s) [i.e. hydroxylating only the proline (Y) position of the Gly-X-Y triplets]. P4H is an enzyme composed of two subunits, alpha and beta. Both are needed to form an active enzyme while the Beta subunit also posses a chaperon function.

The P4H expressed by the genetically modified plant of the present invention is preferably a human P4H which is encoded by, for example, SEQ ID's NO:12 and 14. In addition, P4H mutants which exhibit enhanced substrate specificity, or P4H homologues can also be used.

A suitable P4H homologue is exemplified by an *Arabidopsis* oxidoreductase identified by NCBI accession NP_179363. Pairwise alignment of this protein sequence and a human P4H alpha subunit conducted by the present inventors revealed the highest homology between functional domains of any known P4H homologs of plants.

Since P4H needs to co-accumulate with the expressed collagen chain, the coding sequence thereof is preferably modified accordingly (addition of signal sequences, deletions which may prevent ER targeting etc).

In mammalian cells, collagen is also modified by Lysyl hydroxylase, galactosyltransferase and glucosyltransferase. These enzymes sequentially modify lysyl residues in specific positions to hydroxylysyl, galactosylhydroxylysyl and glucosylgalactosyl hydroxylysyl residues. A single human enzyme, Lysyl hydroxylase 3 (LH3) can catalyze all three consecutive steps in hydroxylysine linked carbohydrate formation.

Thus, the genetically modified plant of the present invention preferably also expresses mammalian LH3. An LH3 encoding sequence such as that set forth by SEQ ID NO: 22 can be used for such purposes.

The collagen chain(s) and modifying enzymes described above can be expressed from a stably integrated or a transiently expressed nucleic acid construct which includes polynucleotide sequences encoding the alpha chains and/or modifying enzymes (e.g. P4H and LH3) positioned under the transcriptional control of plant functional promoters. Such a nucleic acid construct (which is also termed herein as an expression construct) can be configured for expression throughout the whole plant, defined plant tissues or defined plant cells, or at define developmental stages of the plant. Such a construct may also include selection markers (e.g. antibiotic resistance), enhancer elements and an origin of replication for bacterial replication.

It will be appreciated that constructs including two expressible inserts (e.g. two alpha chain types, or an alpha chain and P4H) preferably include an individual promoter for each insert, or alternatively such constructs can express a single transcript chimera including both insert sequences from a single promoter. In such a case, the chimeric transcript includes an IRES sequence between the two insert sequences such that the downstream insert can be translated therefrom.

Numerous plant functional expression promoters and enhancers which can be either tissue specific, developmentally specific, constitutive or inducible can be utilized by the constructs of the present invention, some examples are provided hereinunder.

As used herein in the specification and in the claims section that follows the phrase "plant promoter" or "promoter" includes a promoter which can direct gene expression in plant cells (including DNA containing organelles). Such a promoter can be derived from a plant, bacterial, viral, fungal or animal origin. Such a promoter can be constitutive, i.e., capable of directing high level of gene expression in a plurality of plant tissues, tissue specific, i.e., capable of directing gene expression in a particular plant tissue or tissues, inducible, i.e., capable of directing gene expression under a stimulus, or chimeric, i.e., formed of portions of at least two different promoters.

Thus, the plant promoter employed can be a constitutive promoter, a tissue specific promoter, an inducible promoter or a chimeric promoter.

Examples of constitutive plant promoters include, without being limited to, CaMV35S and CaMV19S promoters, FMV34S promoter, sugarcane bacilliform badnavirus promoter, CsVMV promoter, *Arabidopsis* ACT2/ACT8 actin promoter, *Arabidopsis* ubiquitin UBQ1 promoter, barley leaf thionin BTH6 promoter, and rice actin promoter.

Examples of tissue specific promoters include, without being limited to, bean phaseolin storage protein promoter, DLEC promoter, PHS□ promoter, zein storage protein promoter, conglutin gamma promoter from soybean, AT2S1 gene promoter, ACT11 actin promoter from *Arabidopsis*, napA promoter from *Brassica napus* and potato patatin gene promoter.

The inducible promoter is a promoter induced by a specific stimuli such as stress conditions comprising, for example, light, temperature, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr203J and str246C active in pathogenic stress.

Preferably the promoter utilized by the present invention is a strong constitutive promoter such that over expression of the construct inserts is effected following plant transformation.

It will be appreciated that any of the construct types used in the present invention can be co-transformed into the same plant using same or different selection markers in each construct type. Alternatively the first construct type can be introduced into a first plant while the second construct type can be introduced into a second isogenic plant, following which the transgenic plants resultant therefrom can be crossed and the progeny selected for double transformants. Further self-crosses of such progeny can be employed to generate lines homozygous for both constructs.

There are various methods of introducing nucleic acid constructs into both monocotyledonous and dicotyledenous plants (Potrykus, I., Annu. Rev. Plant. Physiol., Plant. Mol. Biol. (1991) 42:205-225; Shimamoto et al., Nature (1989) 338:274-276). Such methods rely on either stable integration of the nucleic acid construct or a portion thereof into the genome of the plant, or on transient expression of the nucleic acid construct in which case these sequences are not inherited by a progeny of the plant.

In addition, several methods exist in which a nucleic acid construct can be directly introduced into the DNA of a DNA containing organelle such as a chloroplast.

There are two principle methods of effecting stable genomic integration of exogenous sequences such as those included within the nucleic acid constructs of the present invention into plant genomes:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues.

Following transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Transient expression methods which can be utilized for transiently expressing the isolated nucleic acid included within the nucleic acid construct of the present invention include, but are not limited to, microinjection and bombardment as described above but under conditions which favor transient expression, and viral mediated expression wherein a packaged or unpackaged recombinant virus vector including the nucleic acid construct is utilized to infect plant tissues or cells such that a propagating recombinant virus established therein expresses the non-viral nucleic acid sequence.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

The above described transformation approaches can be used to produce collagen chains and/or modifying enzymes as well as assembled collagen (with or without propeptides) in any species of plant, or plant tissue or isolated plants cell derived therefrom.

Preferred plants are those which are capable of accumulating large amounts of collagen chains, collagen and/or the processing enzymes described herein. Such plants may also be selected according to their resistance to stress conditions and the ease at which expressed components or assembled collagen can be extracted. Examples of preferred plants include Tobacco, Maize, Alfalfa, Rice, Potato, Soybean, Tomato, Wheat, Barley, Canola and Cotton.

Collagen fibers are extensively used in the food and cosmetics industry. Thus, although collagen fiber components (alpha chains) and modifying enzymes expressed by plants find utility in industrial synthesis of collagen, complete collagen production in plants is preferred for its simplicity and cost effectiveness.

Several approaches can be used to generate type I collagen in plants. For example, collagen alpha 1 chain can be isolated from a plant expressing collagen alpha 1 and P4H (and optionally LH3) and mixed with a collagen alpha 2 chain which is isolated from a plant expressing collagen alpha 2 and P4H (and optionally LH3 and protease C and/or N). Since collagen alpha 1 chain self assembles into a triple helix by itself, it may be necessary to denature such a homo-trimer prior to mixing and renaturation with the collagen alpha 2 chain.

Preferably, a first plant expressing collagen alpha 1 and P4H (and optionally LH3 and protease C and/or N) can be crossed with a second (and preferably isogenic) plant which expresses collagen alpha 2 or alternatively, a first plant expressing both alpha chains can be crossed with a second plant expressing P4H and optionally LH3 and protease C and/or N.

It should be noted that although the above described plant breeding approaches utilize two individually transformed plants, approaches which utilize three or more individually transformed plants, each expressing one or two components can also be utilized.

One of ordinary skill in the art would be well aware of various plant breeding techniques and as s such no further description of such techniques is provided herein.

Although plant breeding approaches are preferred, it should be noted that a single plant expressing collagen alpha 1 and 2, P4H and LH3 (and optionally protease C and/or N) can be generated via several transformation events each designed for introducing one more expressible components into the cell. In such cases, stability of each transformation event can be verified using specific selection markers.

In any case, transformation and plant breeding approaches can be used to generate any plant, expressing any number of components. Presently preferred are plants which express collagen alpha 1 and 2 chains, P4H, LH3 and at least one protease (e.g. protease C and/or N). As is further described in the Examples section which follows, such plants accumulate collagen which exhibits stability at temperatures of up to 42° C.

Progeny resulting from breeding or alternatively multiple-transformed plants can be selected, by verifying presence of exogenous mRNA and/or polypeptides by using nucleic acid or protein probes (e.g. antibodies). The latter approach is preferred since it enables localization of the expressed polypeptide components (by for example, probing fractionated plants extracts) and thus also verifies a potential for correct processing and assembly. Examples of suitable probes are provided in the Examples section which follows Once collagen-expressing progeny is identified, such plants are further cultivated under conditions which maximize expression of the collagen chains as well as the modifying enzymes.

Since free proline accumulation may facilitate over production of different proline-rich proteins including the collagen chains expressed by the genetically modified plants of the present invention, preferred cultivating conditions are those which increase free proline accumulation in the cultivated plant.

Free proline accumulates in a variety of plants in response to a wide range of environmental stresses including water deprivation, salinization, low temperature, high temperature, pathogen infection, heavy metal toxicity, anaerobiosis, nutrient deficiency, atmospheric pollution and UV-irradiation (Hare and Cress, 1997).

Free proline may also accumulate in response to treatment of the plant or soil with compounds such as ABA or stress inducing compounds such as copper salt, paraquate, salicylic acid and the like.

Thus, collagen-expressing progeny can be grown under different stress conditions (e.g. different concentrations of NaCl ranging from 50 mM up to 250 mM). In order to further enhance collagen production, the effect of various stress conditions on collagen expression will examined and optimized with respect to plant viability, biomass and collagen accumulation.

Plant tissues/cells are preferably harvested at maturity, and the collagen fibers are isolated using well know prior art extraction approaches, one such approach is detailed below.

Leaves of transgenic plants are ground to a powder under liquid nitrogen and the homogenate is extracted in 0.5 M acetic acid containing 0.2 M NaCl for 60 h at 4° C. Insoluble material is removed by centrifugation. The supernatant containing the recombinant collagen is salt-fractionated at 0.4 M and 0.7 M NaCl. The 0.7 M NaCl precipitate, containing the recombinant heterotrimeric collagen, is dissolved in and dialyzed against 0.1 M acetic acid and stored at −20° C. (following Ruggiero et al., 2000).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Constructs and Transformation Schemes

Figure 1D:
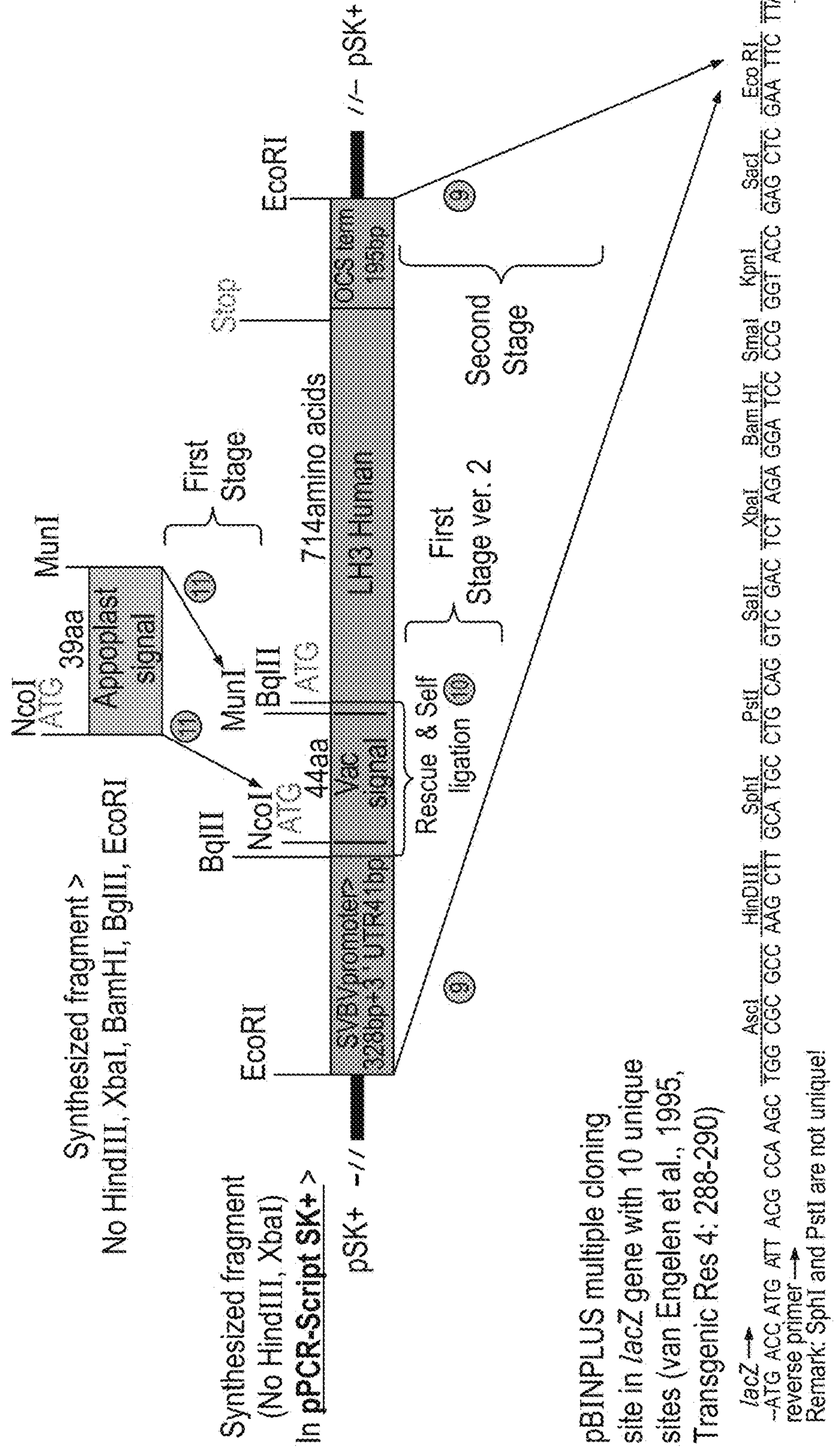

Constructions of expression cassettes and vectors used in this work are illustrated in FIG. 1*a-d*. All of the coding sequences in this work were optimized for expression in tobacco and chemically synthesized with desired flanking regions (SEQ ID NOs: 1, 4, 7, 12, 14, 16, 18, 20, 22). FIG. 1*a*—the synthetic genes coding for Col1 and Col2 (SEQ ID's 1, 4) fused either to the vacuolar signal or to the apoplast signal (encoded by SEQ ID NO: 7) or without signals were cloned in expression cassettes composed of a *Chrysanthemum* rbcS1 promoter and 5' UTR (SEQ ID NO: 10) and a *Chrysanthemum* rbcS1 3'UTR and terminator (SEQ ID NO: 11). The complete expression cassettes were cloned in the multiple cloning site of the pBINPLUS plant transformation vector (van Engelen et al., 1995, Transgenic Res 4: 288-290). FIG. 1*b*—The synthetic genes coding for P4H beta-human, P4H alpha-human and P4H-plant (SEQ ID NOs: 12, 14 and 16) fused either to the vacuolar signal or to the apoplast signal (encoded by SEQ ID NO: 7) or without signals were cloned in expression cassettes composed of the CaMV 35S promoter and TMV omega sequence and *Agrobacterium* Nopaline synthetase (NOS) terminator carried by the vector pJD330 (Galili et al., 1987, Nucleic Acids Res 15: 3257-3273). The complete expression cassettes were cloned in the multiple cloning site of the pBINPLUS vectors carrying the expression cassettes of Col1 or Col2. FIG. 1*c*—The synthetic genes coding for Proteinase C and Proteinase N (SEQ ID NOs: 18, 20) fused either to the vacuolar signal or to the apoplast signal (encoded by SEQ ID NO: 7) were cloned in expression cassettes composed of a *Chrysanthemum* rbcS1 promoter and 5' UTR (SEQ ID NO: 10) and a *Chrysanthemum* rbcS1 3'UTR and terminator (SEQ ID NO: 11). The complete expression cassettes were cloned in the multiple cloning site of the pBINPLUS plant transformation vector. FIG. 1*d*—The synthetic gene coding for LH3 (SEQ ID NO: 22) with flanking Strawberry vein banding virus (SVBV) promoter (NCBI accession AF331666

REGION: 623 . . . 950 version AF331666.1 GI:13345788) and terminated by *Agrobacterium* octopin synthase (OCS) terminator (NCBI accession Z37515 REGION: 1344 . . . 1538 version Z37515.1 GI:886843) fused either to the vacuolar signal or to the apoplast signal (encoded by SEQ ID NO: 7) or without signals was cloned in the multiple cloning site of the pBINPLUS vector carrying the expression cassettes of Col1 and P4H beta.

Figure 2:
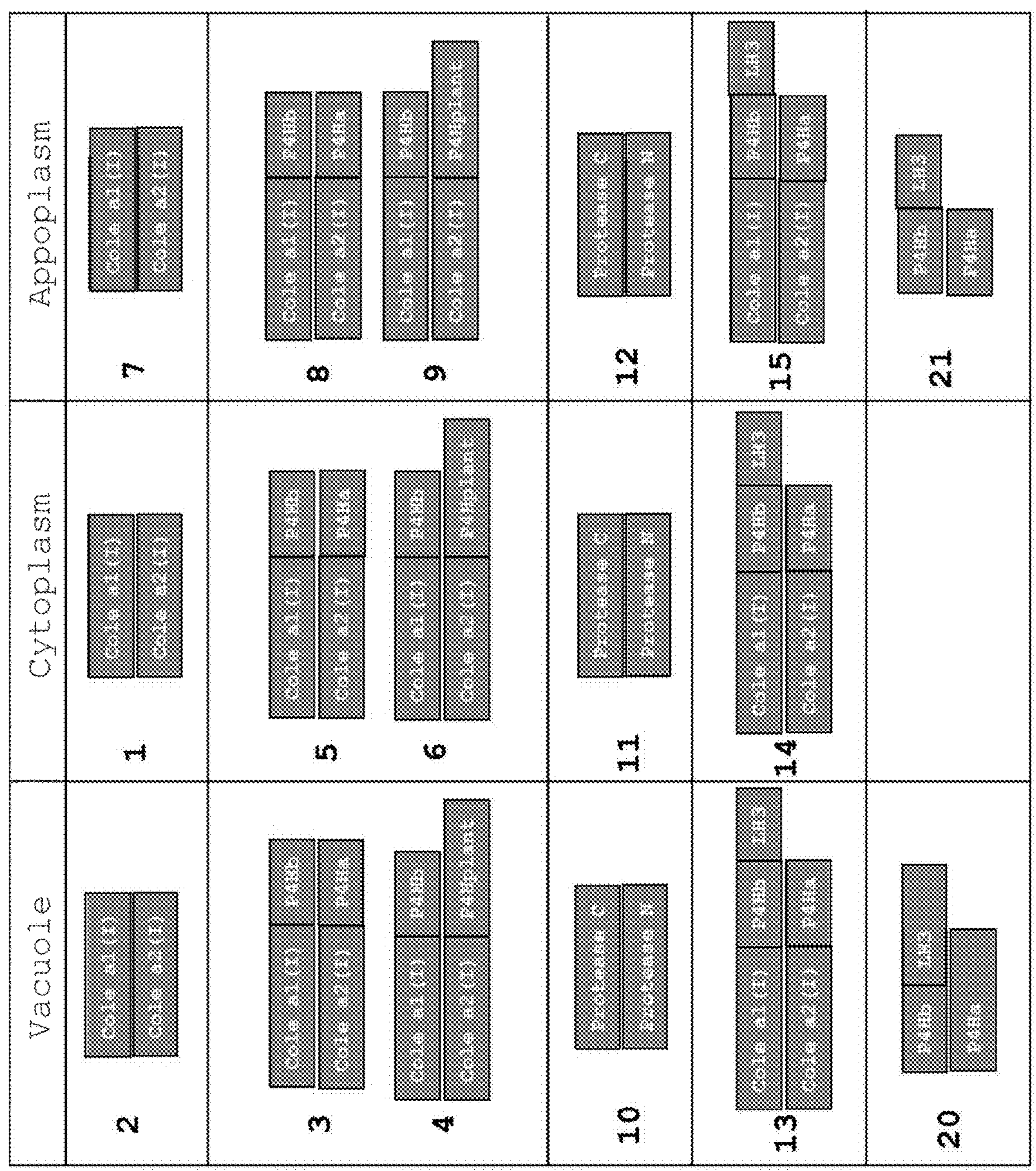
FIG. 2 illustrates various co-transformations approaches. Each expression cassette is represented by the short name of the coding sequence. The coding sequences are specified in table 1. Each co-transformation was performed by two pBINPLUS binary vectors. Each rectangle represents a single pBINPLUS vector carrying one, two or three expression cassettes. Promoter and terminators are specified in Example 1.

Co-transformations schemes utilizing the expression cassettes described in FIG. 1 into a host plant are illustrated in FIG. 2. Each expression cassette insert is represented by a short name of the coding sequence. The coding sequences and related SEQ ID NOs. are described in Table 1. Each co-transformation is preformed by two pBINPLUS binary vectors. Each rectangle represents a single pBINPLUS vector carrying one, two or three expression cassettes. Promoters and terminators are specified in FIG. 1.

Example 2

Plant Collagen Expression

Synthetic polynucleotide sequences encoding the proteins listed in Table 1 below were designed and optimized for expression in tobacco plants.

(ii) Apoplast signal of *Arabidopsis thaliana* endo-1,4-beta-glucanase (Cell, NCBI accession CAA67156.1 GI:2440033); SEQ ID NO. 9, encoded by SEQ ID NO. 7.

Construction of Plasmids

Plant expression vectors were constructed as taught in Example 1, the composition of each constructed expression vector was confirmed via restriction analysis and sequencing.

Expression vectors including the following expression cassettes were constructed:

1. Collagen alpha 1
2. Collagen alpha 1+human P4H beta subunit
3. Collagen alpha 1+human P4H beta subunit+human LH3
4. Collagen alpha 2
5. Collagen alpha 2+with human P4H alpha subunit
6. Collagen alpha 2+with *Arabidopsis* P4H
7. Human P4H beta subunit+human LH3
8. Human P4H alpha subunit Each of the above described coding sequences was either translationally fused to a vacuole transit peptide or to an apoplasm transit peptide or was devoid of any transit peptide sequences, in which case cytoplasmic accumulation is expected.

TABLE 1

List of expressed proteins

| Name: | SwissProt accession | Amino acids | Splicing isoform | Deletions | name | Included in SEQ ID NO. | Encoded by SEQ ID NO. |
|---|---|---|---|---|---|---|---|
| Collagen alpha 1(I) chain [Precursor] | p02452 | 1442 | One version | ER signal | Col1 | 3 | 1 |
| Collagen alpha 2(I) chain [Precursor] | p08123 Two changes done in p08123: D549A and N249I | 1342 | One version | ER signal | Col2 | 6 | 4 |
| Prolyl 4-hydroxylase beta subunit | p07237 | 487 | One version | ER signal, KDEL | P4H betaHuman | 13 | 12 |
| Prolyl 4-hydroxylase alpha-1 subunit | p13674 | 517 | P13674-1 | ER signal | P4H alphaHuman | 15 | 14 |
| Prolyl 4-hydroxylase Plant | No entry in Swissprot. NCBI accession: gi: 15227885 | 252 | One version | Mitochondrial signal predicted as: aa1-39 | P4Hplant | 17 | 16 |
| Procollagen C-proteinase | p13497 | 866 | P13497-1 BMP1-3 | ER signal, propeptide | Proteinase C | 19 | 18 |
| Procollagen I N-proteinase | o95450 | 958 | O95450-1 LpNPI | ER signal, propeptide | Proteinase N | 21 | 20 |
| Lysyl hydroxylase 3 | o60568 | 714 | One version | ER signal | LH3 | 23 | 22 |

Signal Peptides (i) Vacuole signal sequence of barley gene for Thiol protease aleurain precursor (NCBI accession P05167 GI:113603)

```
                                          (SEQ ID NO: 24)
MAHARVLLLALAVLATAAVAVASSSSFADSNPIRPVTDRAASTLA.
```

Plant Transformation and PCR Screening

Tobacco plants (*Nicotiana tabacum*, Samsun NN) were transformed with the above described expression vectors according to the transformation scheme taught in FIG. 2.

Figure 3:
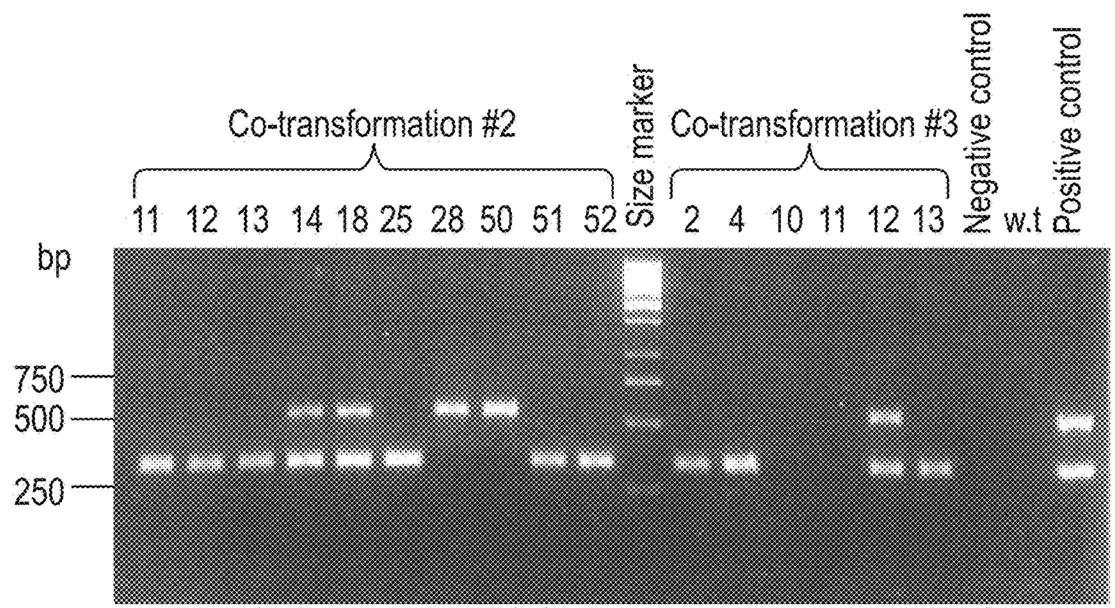
FIG. 3 is a multiplex PCR screening of transformants showing plants that are positive for Collagen alpha 1 (324 bp fragment) or Collagen alpha 2 (537 bp fragment) or both.

Resultant transgenic plants were screened via multiplex PCR using four primers which were designed capable of amplifying a 324 bp fragment of Collagen alpha 1 and a 537 bp fragment of Collagen alpha 2 (Table 2). FIG. 3 illustrates the results of one mulitplex PCR screen.

TABLE 2

| List of primers for multiplex PCR for amplification of a 324 bp fragment of Collagen alpha I and a 537 bp fragment of Collagen alpha 2 | | |
|---|---|---|
| Col1 forward primer (24-mer): | 5' ATCACCAGGAGAACAGGGACCATC 3' | SEQ ID 25 |
| Col1 reverse primer (29-mer): | 5' TCCACTTCCAAATCTCTATCCCTAACAAC 3' | SEQ ID 26 |
| Col2 forward primer (23-mer): | 5' AGGCATTAGAGGCGATAAGGGAG 3' | SEQ ID 27 |
| Col2 reverse primer (27-mer): | 5' TCAATCCAATAATAGCCACTTGACCAC 3' | SEQ ID 28 |

Example 3

Detection of Human Collagen in Transgenic Tobacco Plants

Figure 4:
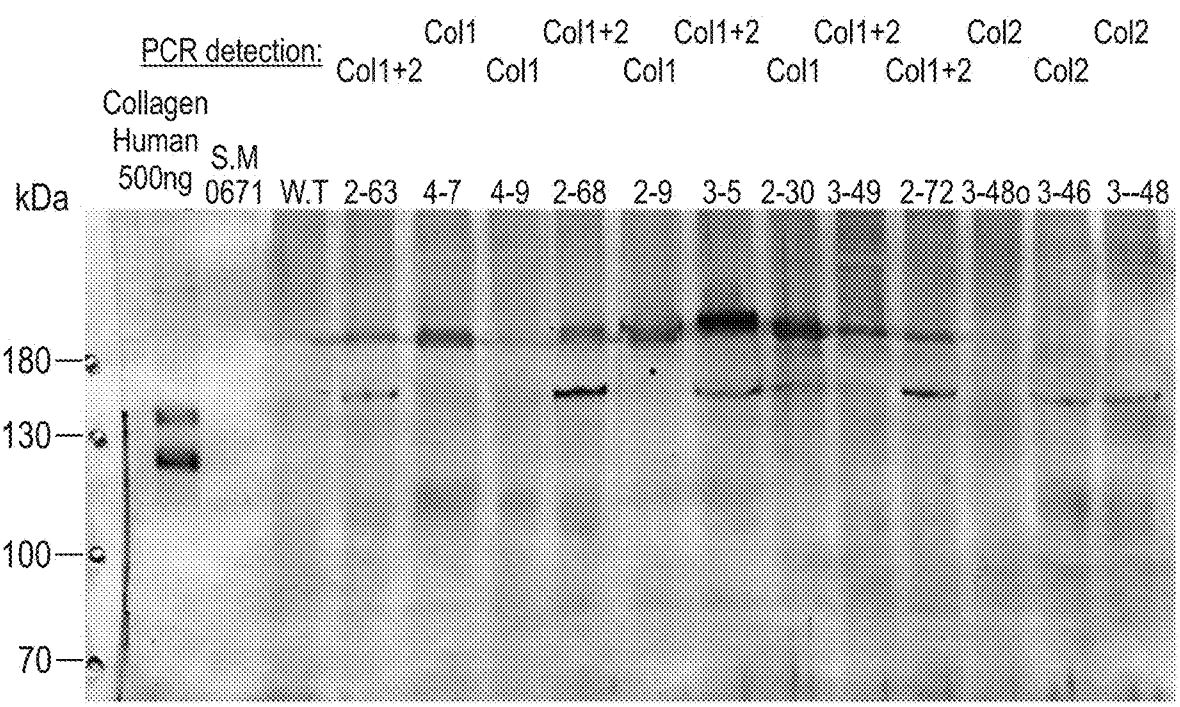
FIG. 4 is western blot analysis of transgenic plants generated by co-transformations 2, 3 and 4. Total soluble proteins were extracted from tobacco co-transformants #2, #3 and #4 and tested with anti-Collagen I antibody (# AB745 from Chemicon Inc.). Size markers were # SM0671 from Fermentas Inc. W.T. is a wild type tobacco. Positive collagen bands are visible in plants that are PCR positive for collagen type I alpha 1 or alpha 2 or both. Positive control band of 500 ng collagen type I from human placenta (# CC050 from Chemicon Inc., extracted from human placenta by pepsin digestion) represents about 0.3% of the total soluble proteins (about 150 μg) in the samples from the transgenic plants. The larger band at about 140 kDa in the human collagen sample is a procollagen with it's C-propeptide as detected by anti carboxy-terminal pro-peptide of collagen type I antibody (# MAB1913 from Chemicon Inc.). The smaller band at about 120 kDa in the human collagen sample is a collagen without propeptides. Due to their unusual composition proline rich proteins (including collagen)s consistently migrate on polyacrylamid gels as bands with molecular mass higher than expected. Therefore the collagen chains without propeptides with a molecular weight of about 95 kDa migrate as a band of about 120 kDa.

Total soluble proteins were extracted from tobacco transformants 2, 3 and 4 by grinding 500 mg of leaves in 0.5 ml 50 mM Tris-HCl pH=7.5 with a "Complete" protease inhibitor cocktail (product #1836145 from Roche Diagnostics GmbH, 1 tablet per 50 ml buffer). The crude extract was mixed with 250 μl 4× Sample application buffer containing 10% beta-mercapto-ethanol and 8% SDS, the samples were boiled for 7 minutes and centrifuged for 8 minutes in 13000 rpm. 20 μl of the supernatant were loaded in a 10% polyacrylamide gel and tested with anti-Collagen I (denatured) antibody ((# AB745 from Chemicon Inc.) in a standard Western blot procedure (FIG. 4). W.T. is a wild type tobacco. Positive collagen bands are visible in plants that are PCR positive for collagen typeI alpha 1 or alpha 2 or both. Positive control band of 500 ng collagen type I from human placenta (# CC050 from Chemicon Inc.) represents about 0.3% of the total soluble proteins (about 150 μg) in the samples from the transgenic plants.

Figure 5:
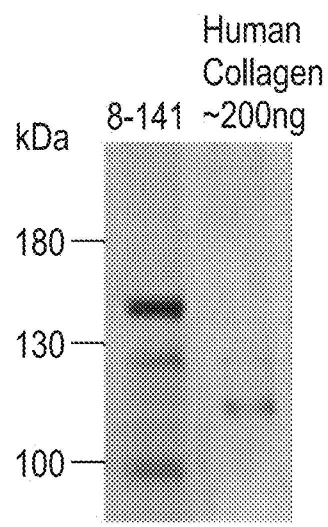
FIG. 5 is a western blot analysis of transgenic plant generated by co-transformation #8 (carrying appoplast signals translationally fused to the collagen chains). Total soluble proteins were extracted from transgenic tobacco leaves and tested with anti-Collagen I antibody (# AB745 from Chemicon Inc.) Positive collagen alpha 2 band is visible in plant 8-141. Collagen type I from human placenta (# CC050 from Chemicon Inc.) served as control.

Plants expressing collagen at the expected molecular weight up to ~1% of the total soluble proteins were detected when collagen was targeted to the vacuole (FIG. 4). Subcellular targeting of full length collagen to the apoplast was successfully achieved (FIG. 5). Plants expressing collagen in the cytoplasm (i.e. no targeting peptide) did not accumulate collagen to detectable levels showing that subcellular targeting of collagen in plants is critical for success.

In addition in contrast to the studies of Ruggiero et al. 2000 and Merle et al. 2002 which showed that collagen lacking the N-propeptide was subjected to significant proteolysis, using the present approach full length collagen proteins with C-propeptide and N-propeptide accumulated in subcellular compartments at high levels.

The present data also clearly shows that crossing two plants each expressing a different collagen chain type is advantageous in that it enables selection of plants expressing optimal levels of each chain type and subsequent plant crossing to achieve the desired collagen producing plant.

Collagen produced by the plants of the present invention includes the native propeptides and therefore is expected to form a larger protein then the human control that was purified by proteolysis. The calculated molecular weight of Collagen alpha 1 and alpha 2 chains without hydroxylations or glycosylations are the following: Col1 with propeptides—136 kDa, Col1 without propeptides—95 kDa, Col2 with propeptides—127 kDa, Col2 without propeptides—92 kDa.

As can be seen in FIG. 4, the Col1 bands in transformants 3-5 and 3-49 appears larger then Col1 bands in other plants. This indicates prolines hydroxylation in collagen chains by human proline-4-hydroxylase holoenzyme composed of alpha and beta subunits that were coexpressed in these plants and targeted to the same subcellular compartment as the human collagen chains (e.g. vacuole).

Example 4

Collagen Triple Helix Assembly and Thermal Stability in Transgenic Plants

Figure 6A:
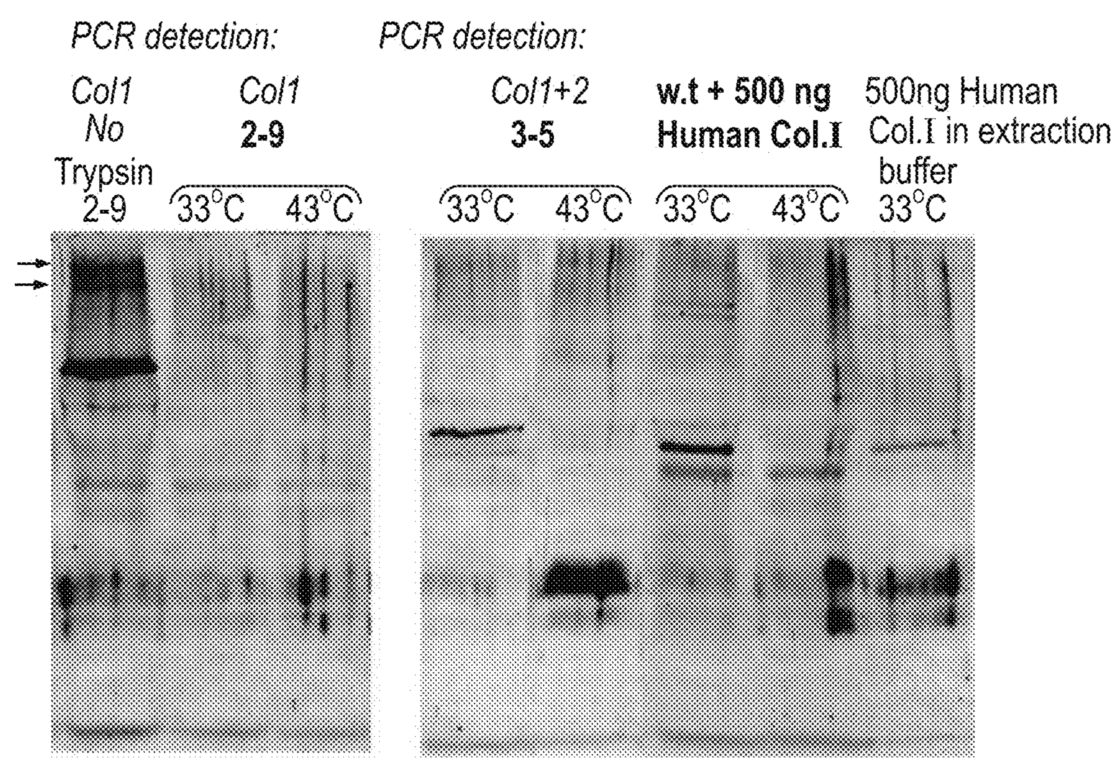
FIGS. 6*a-b* illustrate collagen triple helix assembly and thermal stability as qualified by heat treatment and Trypsin or Pepsin digestion.
Figure 6B:
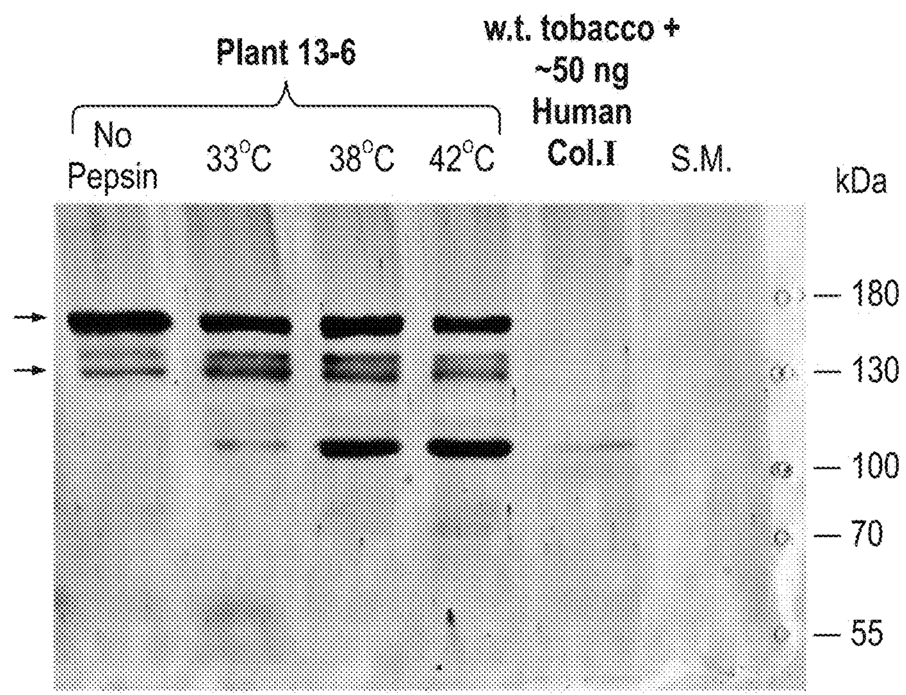

Assembly of collagen triple helix and the helix thermal stability in transgenic plants were tested by thermal denaturation followed by trypsin or pepsin digestion of the total crude protein extract of transgenic plants (FIGS. 6*a*-*b*).

In a first experiment, total soluble proteins from tobacco 2-9 (expressing only col alfa1 and no P4H) and 3-5 (expressing both col alfa1+2 and P4H) were extracted by grinding 500 mg leaves in 0.5 ml of 50 mM Tris-HCl pH=7.5, centrifuging for 10 minutes in 13000 rpm and collecting the supernatant. 50 μl of the supernatant were subjected to heat treatment (15 minutes in 33° C. or 43° C.) and then immediately placed on ice. Trypsin digestion was initiated by adding to each sample 60 of 1 mg/ml Trypsin in 50 mM Tris-HCl pH=7.5. The samples were incubated for 20 minutes at room temperature (about 22° C.). The digestion was terminated by addition of 20 μl 4× sample application buffer containing 10% betamercaptoethanol and 8% SDS, the samples were boiled for 7 minutes and centrifuged for 7 minutes at 13000 rpm. 50 μl of the supernatant were loaded onto a 10% polyacrylamide gel and tested with anti-Collagen I antibody ((# AB745 from Chemicon Inc.) using a standard Western blot procedure. Positive controls were samples of ~500 ng human collagen I (# CC050 from Chemicon Inc., extracted from human placenta by pepsin digestion) which was added to 50 μl total soluble proteins extracted from w.t. tobacco.

As shown in FIG. 6*a*, collagen triple helix that formed in plants #3-5 as well as control human collagen was resistant to denaturation at 33° C. In contrast, collagen formed by plants #2-9 denatured at 33° C. This difference in thermal stability indicates a successful triple helix assembly and post translational proline hydroxylation in transformants #3-5 which express both collagen alpha 1 and collagen alpha 2 as well as P4H beta and alpha subunits.

Two bands in transformants #2-9 may represent dimers or trimers, which are stable following 7 minutes of boiling with SDS and mercaptoethanol. Similar bands are visible in human collagen (upper panel) and in transformants #3-5. A possible explanation is a covalent bond between two peptides in different triple helixes (cross link), formed following oxidative deamination of two lysines by Lysine oxidase.

In a second experiment, total soluble proteins from transgenic tobacco 13-6 (expressing collagen I alpha 1 and alpha 2 chains—pointed by arrows, human P4H alpha and beta subunits and human LH3) were extracted by grinding 500 mg of leaves in 0.5 ml of 100 mM Tris-HCl pH=7.5 and 300 mM NaCl, centrifuging for 7 minutes at 10000 rpm and collecting the supernatant. 50 μl of the supernatant was subjected to heat treatment (20 minutes in 33° C., 38° C. or 42° C.) and then immediately placed on ice. Pepsin digestion was initiated by adding to each sample 4.50 of 0.1M HCl and 4 µl of 2.5 mg/ml Pepsin in 10 mM acetic acid. The samples were incubated for 30 minutes at room temperature (about 22° C.). The digestion was terminated by adding 5 µl of unbuffered 1 M Tris. Each sample was mixed with 22 µl 4× Sample application buffer containing 10% beta-mercapto-ethanol and 8% SDS, boiled for 7 minutes and centrifuged for 7 minutes in 13000 rpm. 40 µl of the supernatant were loaded in a 10% polyacrylamide gel and tested with anti-Collagen I antibody ((# AB745 from Chemicon Inc.) in a standard Western blot procedure. Positive control was sample of ~50 ng human collagen I (# CC050 from Chemicon Inc., extracted from human placenta by pepsin digestion) added to total soluble proteins from w.t. tobacco.

As is illustrated in FIG. 6*b*, collagen triple helix that formed in plant #13-6 was resistant to denaturation at 42° C. Cleavage of the propetides is first visible at 33° C. and gradually increases in efficiency when the temperature is raised to 38° C. and again to 42° C. The cleaved collagen triple helix domain shows a similar migration on the gel to the migration of the pepsin treated human collagen. The human collagen that was used in this experiment was extracted from human placenta by pepsin proteolysis and therefore lacks the propeptides and some of the telopeptides.

Example 5

Plant P4H Expression

Induction of Native Plant P4H

Figure 7:
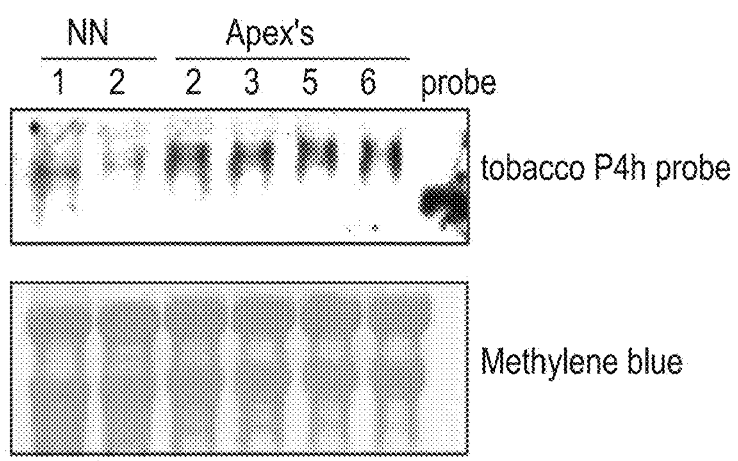
FIG. 7 illustrates Northern blot analysis conducted on wild type tobacco. Blots were probed with tobacco P4H cDNA.
Figure 7:
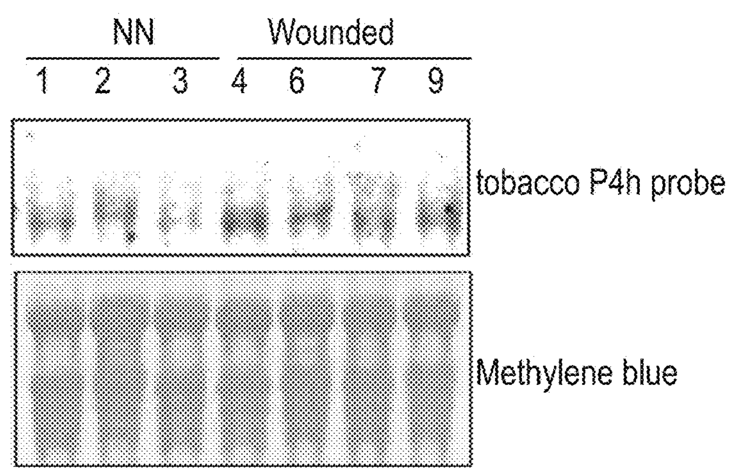

Tobacco P4H cDNA was cloned and used as a probe to determine conditions and treatments that would induce endogenous P4H expression. Northern blot analysis (FIG. 7) clearly shows that P4H is expressed at relatively high levels in the shoot apex and at low levels in leaves. P4H level was induced significantly in leaves 4 hours following abrasion treatment ("wounded" in the lower panel). Similar results were achieved using other stress conditions (not shown).

Figure 8:
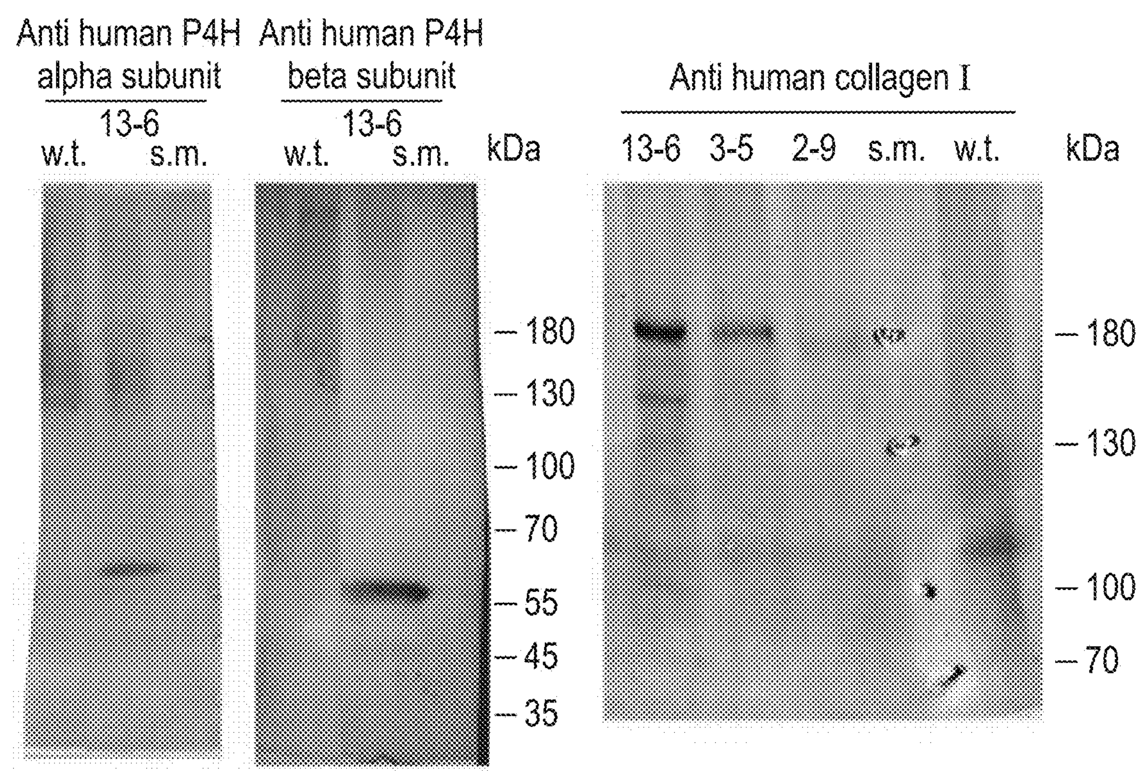
FIG. 8 is a western blot analysis of transgenic plants generated by co-transformations 2, 3 and 13. Total soluble protein was extracted from tobacco co-transformants and tested with anti human P4H alpha and beta and anti-Collagen I antibodies.

Detection of Human P4H Alpha and Beta Subunits and Collagen Alpha 1 and Alpha 2 Chains in Transgenic Tobacco Plants Detection of human P4H alpha and beta subunits and collagen type I alpha 1 and alpha 2 chains in transgenic tobacco plants was effected using anti-human P4H alpha subunit antibody (#63-163 from ICN Biomedicals Inc.), anti-human P4H beta subunit antibody (# MAB2701 from Chemicon Inc.) and anti-Collagen I antibody (# AB745 from Chemicon Inc.). The results of a western blot probed with these antibodies are shown in FIG. 8.

Expression of P4H alpha, P4H beta and collagen I alpha 1 and alpha 2 bands was confirmed in plant 13-6 (also transformed also with human LH3). The calculated molecular weights of P4H alpha and beta including the vacuolar signal peptide are 65.5 kDa and 53.4 kDa respectively. The calculated molecular weights of Collagen alpha 1 and alpha 2 chains with propeptides, without hydroxylations or glycosylations are 136 kDa and 127 kDa respectively.

Example 6

Vacuolar Targeted Collagen is Stably Expressed in Dark-Grown Plants

Collagen Expressing Plants—

The 20-279 parental tobacco plant line was generated by co-transformation with an expression vector expressing P4Hbeta+LH3 and another expression vector expressing P4Halpha. Each gene is preceded by a vacuolar targeting determinant of aleurain, a plant vacuolar thiol protease, The 2-300 parental tobacco plant line was generated by co-transformation with an expression vector expressing col1 and another expression vector expressing col2. Each gene is preceded by a vacuolar targeting determinant of aleurain, a plant vacuolar thiol protease.

The 13-652 plant was generated by co-transformation of tobacco plant with an expression vector encoding Col1, P4Hbeta and LH3 and a second expression vector encoding Col2 and P4H alpha. Each gene is preceded by a vacuolar targeting determinant of aleurain, a plant vacuolar thiol protease, Cassete sequences included in the vectors are described in Example 1 above.

Light and Darkness Trial—

Analysis of six 13-6/52 homozygote plants. Samples from leaf #4+5/6 were taken daily at the same time (12:30) for 8 days, from 3 plants that were grown at regular conditions (16 hours under light conditions and 8 hours in the dark) and from 3 plants that were grown only in the dark.

Total Protein Extraction and Western Blot Analysis—

Ninety mg of tobacco leaves were homogenized by mixer mill Type MM301 (Retsch) in an extraction buffer (100 mM Tris HCl pH=7.5, protease inhibitor cocktail available from Roche Catalog Number, 04-693-116-001) at 4° C. Following 30 min of centrifugation (20,000×g at 4° C.), the supernatant was collected. Protein samples were fractionated on 8% SDS-PAGE (Laemmli 1970) and transferred to a nitrocellulose membrane using BIO-RAD™ Protein TRANS-BLOT™ apparatus. The membrane was blocked for 30 min at room temperature in 3% (g/v) skim milk (Difco), and then reacted with either commercial rabbit anti-human collagen type I polyclonal antibodies (Chemicon), for over night (o.n.) at room temperature. The membrane was rinsed with water 3-5 times and then washed for 30 min in TBS. Following incubation with a secondary antibody [goat anti rabbit-IgG antibody conjugated to alkaline phosphatase (chemicon)] for 2 hours at room temperature, the membrane was rinsed with water for 3-5 times and washed for 30 min in TBS. Immunodetection was effected with nitrotetrazolium blue chloride (NBT, Sigma) and 5-bromo-4-chloro-3-indolyl phosphate p-toluidine salt (BCIP, Sigma), at room temperature for 2 hour-o.n.

Results

Figure 9:
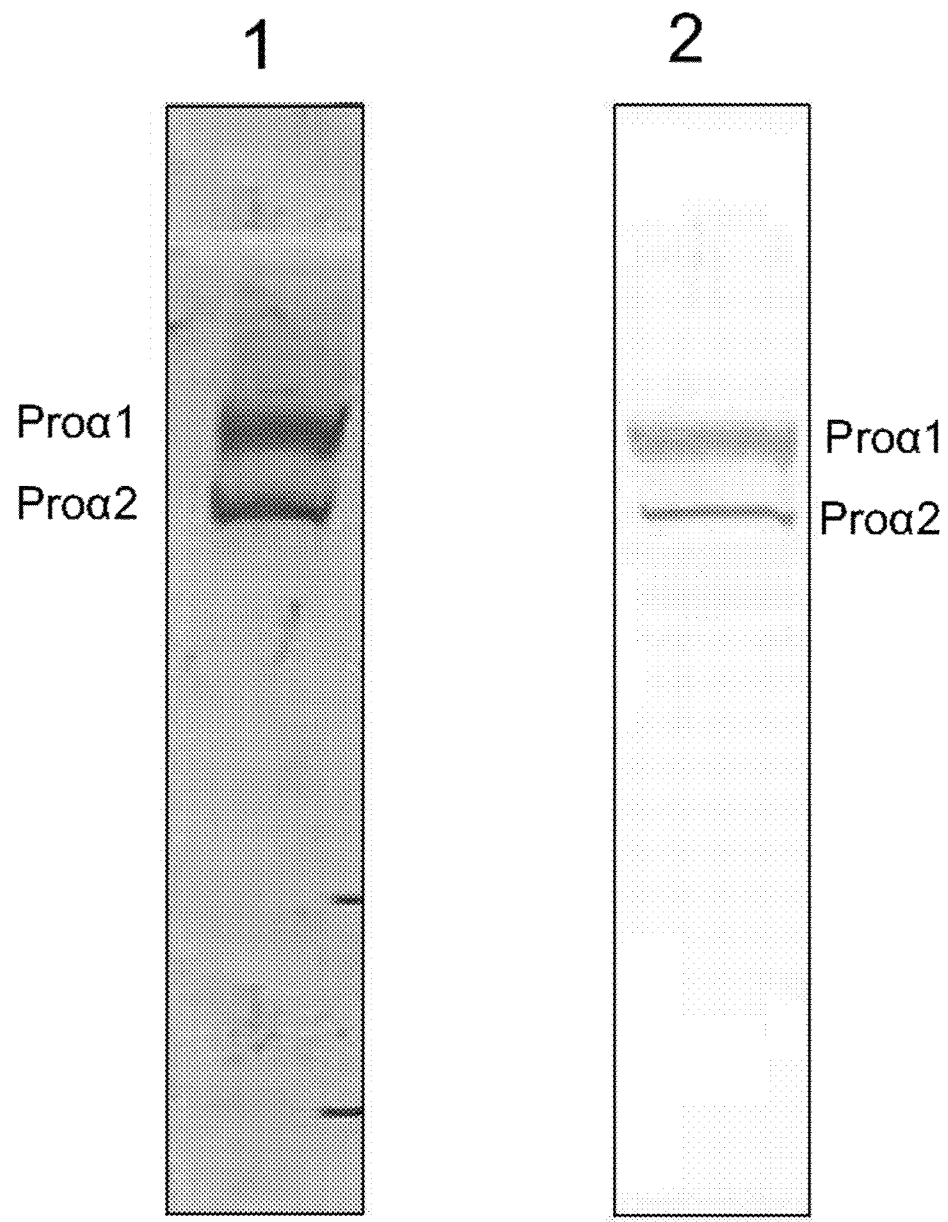
FIG. 9 is a western blot analysis of (lane 1) cross breeding vacuolar targeted plants A(2-300♀y+20-279♂) grown under normal light regimen; and 13-652 vacuolar targeted plants grown for 8 days in the dark. All plants express exogenous col1, col2, P4H α and β as well as LH3 (PCR validated).

As shown in FIG. 9, tobacco plants transgenic for vacuolar targeted collagen express Proα1 and Proα2 (lane 1). Collagen from dark grown vacuolar targeted plants exhibited similar stability (lane 2), substantiating the exceptional stability of collagen generated according to the teachings of the present invention It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES

Other References are Cited in the Document

1. Bulleid N J, John D C, Kadler K E. Recombinant expression systems for the production of collagen. Biochem Soc Trans. 2000; 28(4):350-3. Review. PMID: 10961917 [PubMed—indexed for MEDLINE]
2. Hare P D, Cress W A. Metabolic implications of stress-induced proline accumulation in plants. Plant Growth Regulation 1997; 21: 79-102.
3. Hieta R, Myllyharju J. Cloning and characterization of a low molecular weight prolyl 4-hydroxylase from *Arabidopsis thaliana*. Effective hydroxylation of proline-rich, collagen-like, and hypoxia-inducible transcription factor alpha-like peptides. J Biol Chem. 2002 Jun. 28; 277(26): 23965-71. Epub 2002 Apr. 25. PMID: 11976332 [PubMed—indexed for MEDLINE]
4. Hulmes D J. Building collagen molecules, fibrils, and suprafibrillar structures. J Struct Biol. 2002 January-February; 137(1-2):2-10. Review. PMID: 12064927 [PubMed—indexed for MEDLINE]
5. Inkinen K. Connective tissue formation in wound healing. An experimental study. Academic Dissertation, September 2003. University of Helsinki, Faculty of Science, Department of Biosciences, Division of Biochemistry (ISBN 952-10-1313-3)
6. Merle C, Perret S, Lacour T, Jonval V, Hudaverdian S, Garrone R, Ruggiero F, Theisen M. Hydroxylated human homotrimeric collagen I in *Agrobacterium tumefaciens*-mediated transient expression and in transgenic tobacco plant. FEBS Lett. 2002 Mar. 27; 515(1-3):114-8. PMID: 11943205 [PubMed—indexed for MEDLINE]
7. Olsen D, Yang C, Bodo M, Chang R, Leigh S, Baez J, Carmichael D, Perala M, Hamalainen E R, Jarvinen M, Polarek J. Recombinant collagen and gelatin for drug delivery. Adv Drug Deliv Rev. 2003 Nov. 28; 55(12): 1547-67. PMID: 14623401 [PubMed—in process]
8. Ruggiero F, Exposito J Y, Bournat P, Gruber V, Perret S, Comte J, Olagnier B, Garrone R, Theisen M.

Triple helix assembly and processing of human collagen produced in transgenic tobacco plants. FEBS Lett. 2000 Mar. 3; 469(1):132-6. PMID: 10708770 [PubMed—indexed for MEDLINE]

9. Tanaka M, Sato K, Uchida T. Plant prolyl hydroxylase recognizes poly(L-proline) II helix. J Biol Chem. 1981 Nov. 25; 256(22):11397-400. PMID: 6271746 [PubMed—indexed for MEDLINE]
10. Wang C, Luosujarvi H, Heikkinen J, Risteli M, Uitto L, Myllyla R. The third activity for lysyl hydroxylase 3: galactosylation of hydroxylysyl residues in collagens in vitro. Matrix Biol. 2002 November; 21(7):559-66. PMID: 12475640 [PubMed—indexed for MEDLINE]

What is claimed:

1. A plant system comprising:

(a) a first genetically modified plant which comprises:

(i) an exogenous polynucleotide sequence encoding a collagen alpha 1 chain; and (ii) an exogenous polynucleotide sequence encoding a collagen alpha 2 chain; and (b) a second genetically modified plant which comprises (iii) an exogenous polynucleotide sequence encoding human prolyl-4-hydroxylase (P4H); and (iv) an exogenous polynucleotide sequence encoding human lysyl hydroxylase (LH3), wherein each of said collagen alpha 1 chain, said collagen alpha 2 chain, said P4H and said LH3 is attached to a vacuole transit peptide and a plant promoter, wherein each of said collagen alpha 1 chain, said collagen alpha 2 chain, said P4H and said LH3 is devoid of an ER retention signal.

2. The plant system of claim 1, wherein said collagen is type I collagen.

3. The plant system of claim 1, wherein said collagen is human collagen.

4. The plant system of claim 3, wherein said human collagen is encoded by SEQ ID NOs: 1 and 4.

5. The plant system of claim 1, wherein each of said collagen alpha 1 chain and said collagen alpha 2 chain comprises a C-terminus and/or an N-terminus propeptide.

* * * * *

SEQUENCE LISTING

```
<160> NUMBER OF SEQ ID NOS: 29

<210> SEQ ID NO 1
<211> LENGTH: 4662
<212> TYPE: DNA
<213> ORGANISM: Artificial sequence
<220> FEATURE:
<223> OTHER INFORMATION: Synthetic sequence containing the coding
      regions of the vacuolar signal sequence of barley gene for Thiol
      protease aleurain precursor fused to the human Collagen alpha 1(I)
      chain and flanking regions

<400> SEQUENCE: 1

gcgatgcatg taatgtcatg agccacatga tccaatggcc acaggaacgt aagaatgtag      60

atagatttga ttttgtccgt tagatagcaa acaacattat aaaaggtgtg tatcaatacg     120

aactaattca ctcattggat tcatagaagt ccattcctcc taagtatcta aaccatggct     180

cacgctcgtg ttctcctcct cgctctcgct gttttggcaa cagctgctgt ggctgtggct     240

tctagttctt cttttgctga ttcaaaccct attagacctg ttactgatag agcagcttcc     300

actttggctc aattgcaaga ggagggccag gttgagggcc aagatgagga tatccctcca     360

attacatgcg tgcaaaatgg cttgcgttac cacgataggg atgtgtggaa acctgaacct     420

tgtcgtatct gtgtgtgtga taacggcaag gtgctctgcg atgatgttat ctgcgatgag     480

acaaaaaatt gccctggcgc tgaagttcct gagggcgagt gttgccctgt gtgccctgat     540

ggttccgagt ccccaactga tcaggaaact actggcgtgg agggcccaaa aggagatact     600

ggtccacgtg gtcctagggg tccagcaggt cctccaggta gagatggtat tccaggccag     660

cctggattgc caggaccacc aggcccacct ggcccaccag gacctcctgg tcttggtgga     720
```

-continued

```
aatttcgctc cacaactctc ttatggctat gatgagaagt caacaggtgg tatttccgtt    780
ccaggtccta tgggaccatc cggaccaaga ggtctcccag gtcctccagg tgctcctgga    840
cctcaaggct ttcaaggacc tccaggcgaa ccaggagaac caggcgcttc tggaccaatg    900
ggcccaaggg gaccacctgg cccaccagga aaaaatggcg atgatggcga agctggaaag    960
cctggtcgtc ctggagagag aggtcctcct ggcccacagg gtgcaagagg cttgccagga   1020
actgctggct tgcctggaat gaagggacat aggggcttct ccggcctcga tggcgctaag   1080
ggtgatgctg gccctgctgg accaaagggc gagccaggtt cccctggaga aaacggtgct   1140
cctggacaaa tgggtcctcg tggacttcca ggagaaaggg gtcgtccagg cgctccagga   1200
ccagcaggtg ctaggggaaa cgatggtgca acaggcgctg ctggccctcc tggcccaact   1260
ggtcctgctg gccctccagg attcccaggc gcagttggag ctaaaggaga agcaggacca   1320
cagggcccta ggggttctga aggacctcag ggtgttagag gtgaaccagg tcctccaggc   1380
ccagctggag cagctggtcc agcaggaaat ccaggtgctg atggtcaacc tggagctaag   1440
ggcgctaatg gcgcaccagg tatcgcaggc gcaccaggtt ttcctggcgc tagaggccca   1500
agtggtcctc aaggaccagg tggaccacca ggtccaaaag gcaattctgg cgaacctggc   1560
gctccaggtt ctaaaggaga tactggtgct aaaggcgaac caggacctgt tggtgttcag   1620
ggtcctcctg gtcctgctgg agaagaagga aaaagaggtg ctcgtggaga accaggacca   1680
actggacttc ctggacctcc tggtgaacgt ggcggacctg gctcaagggg tttccctgga   1740
gctgatggag tggcaggtcc aaaaggccct gctggagaga gaggttcacc aggtccagct   1800
ggtcctaagg gctcccctgg tgaagcaggt agaccaggcg aagcaggatt gccaggcgca   1860
aagggattga caggctctcc tggtagtcct ggcccagatg gaaaaacagg cccaccaggt   1920
ccagcaggac aagatggacg tccaggccca ccaggtcctc ctggagcaag gggacaagct   1980
ggcgttatgg gttttccagg acctaaaggt gctgctggag agccaggaaa ggcaggtgaa   2040
agaggagttc ctggtccacc aggagcagtg ggtcctgctg gcaaagatgg tgaagctgga   2100
gcacagggcc ctccaggccc tgctggccca gctggcgaac gtggagaaca aggcccagct   2160
ggtagtccag gatttcaagg attgcctggc cctgctggcc ctccaggaga agcaggaaaa   2220
cctggagaac aaggagttcc tggtgatttg ggagcacctg gaccttcagg agcacgtggt   2280
gaaagaggct tccctggcga gaggggtgtt caaggtccac caggtccagc aggacctaga   2340
ggtgctaatg gcgctcctgg caacgatgga gcaaaaggtg atgctggtgc tcctggcgca   2400
cctggaagtc agggtgctcc tggattgcaa ggaatgcctg gagagagggg tgctgctggc   2460
ttgccaggcc caaagggcga taggggtgat gctggaccaa aaggtgctga tggatcccca   2520
ggaaaagatg gagttcgtgg tcttactggc ccaatcggac ctccaggccc tgctggcgct   2580
ccaggtgata agggcgaaag tggcccaagt ggacctgctg gacctactgg tgctagaggt   2640
gcacctggtg ataggggtga acctggacca cctggtccag ctggttttgc tggtcctcct   2700
ggagctgatg gacaacctgg cgcaaagggt gaaccaggtg atgctggcgc aaagggagat   2760
gctggtccac ctggacctgc tggtccagca ggcccccctg ggccaatcgg taatgttgga   2820
gcaccaggtg ctaagggagc taggggttcc gctggtccac ctggagcaac aggatttcca   2880
ggcgctgctg gtagagttgg cccaccaggc ccatccggaa acgcaggccc tcctggtcct   2940
ccaggtcctg ctggcaagga gggtggcaaa ggaccaaggg gcgaaactgg ccctgctggt   3000
agacctggcg aagttggccc tcctggacca ccaggtccag caggagaaaa aggttcccca   3060
ggagctgatg gcccagctgg tgctccagga actccaggcc ctcaaggtat tgctggacag   3120
```

```
agaggcgttg tgggactccc tggtcaaagg ggagagagag gatttccagg cttgccagga   3180

cctagtggag aacctggaaa acaaggccca tcaggcgcta gtggagagcg tggacctcct   3240

ggccctatgg gacctcctgg attggctggc ccacctggcg aatcaggtcg tgaaggcgca   3300

ccaggcgcag aaggatcacc tggaagagat ggatcccctg gtgctaaagg cgatcgtgga   3360

gaaactggtc cagcaggccc accaggcgca ccaggtgcac ctggcgctcc aggacctgtg   3420

ggaccagctg gaaaatccgg agatagggc gagacaggcc cagcaggacc agctggacct   3480

gttggccctg ctggcgctcg tggaccagca ggacctcaag gaccaagggg agataaggga   3540

gaaacaggcg aacaaggcga taggggcatt aagggtcata ggggttttag tggcctccag   3600

ggtcctcctg gcccacctgg atcaccagga gaacagggac catctggtgc ttccggccca   3660

gctggtccaa gaggacctcc aggatcagct ggtgcacctg gaaaagatgg tcttaacggt   3720

ctcccaggac caatcggccc tccaggacct agaggaagaa caggagatgc tggccctgtt   3780

ggccctccag gacctcctgg tccaccaggt ccacctggtc ctccatcagc tggattcgat   3840

ttttcatttc ttccacagcc accacaagag aaagctcacg atggcggcag atattaccgt   3900

gctgatgatg ctaacgttgt tagggataga gatttggaag tggatacaac tttgaaatcc   3960

ctctcccagc aaattgaaaa cattagatct ccagaaggtt cacgtaaaaa cccagctaga   4020

acatgtcgtg atttgaaaat gtgtcactcc gattggaaaa gtggtgaata ctggattgat   4080

ccaaatcagg gctgtaatct cgatgctatc aaagtttctt gtaacatgga aacaggcgaa   4140

acatgcgttt atcctactca accttccgtg gctcagaaaa attggtacat ctcaaaaaat   4200

cctaaagata agaggcacgt ttggttcggt gaaagtatga ctgatggatt tcaatttgag   4260

tacggcggtc aaggtagtga tccagctgat gtggctattc aactcacatt tttgcgtctt   4320

atgtccacag aggcatcaca aaacatcact taccactgca aaaacagtgt ggcttatatg   4380

gatcaacaaa caggaaacct taagaaggct cttcttttga agggctcaaa cgagattgag   4440

attagagcag agggcaactc aaggtttact tattcagtta ctgttgatgg ctgcacttca   4500

catactggcg cttggggtaa aacagttatc gagtataaga ctacaaaaac atcaagactc   4560

ccaatcattg atgttgctcc tctcgatgtt ggcgctcctg atcaagagtt cggttttgat   4620

gtgggcccag tttgtttcct ctaatgagct cgcggccgca tc                      4662


<210> SEQ ID NO 2
<211> LENGTH: 4662
<212> TYPE: DNA
<213> ORGANISM: Artificial sequence
<220> FEATURE:
<223> OTHER INFORMATION: Synthetic sequence of the vacuolar signal
      sequence of barley gene for Thiol protease aleurain precursor
      fused to the human Collagen alpha 1(I) chain and flanking regions
<220> FEATURE:
<221> NAME/KEY: CDS
<222> LOCATION: (175)..(4644)

<400> SEQUENCE: 2

gcgatgcatg taatgtcatg agccacatga tccaatggcc acaggaacgt aagaatgtag     60

atagatttga ttttgtccgt tagatagcaa acaacattat aaaaggtgtg tatcaatacg    120

aactaattca ctcattggat tcatagaagt ccattcctcc taagtatcta aacc atg      177
                                                            Met
                                                            1

gct cac gct cgt gtt ctc ctc ctc gct ctc gct gtt ttg gca aca gct      225
Ala His Ala Arg Val Leu Leu Leu Ala Leu Ala Val Leu Ala Thr Ala
            5                   10                  15
```

```
gct gtg gct gtg gct tct agt tct tct ttt gct gat tca aac cct att      273
Ala Val Ala Val Ala Ser Ser Ser Ser Phe Ala Asp Ser Asn Pro Ile
        20                  25                  30

aga cct gtt act gat aga gca gct tcc act ttg gct caa ttg caa gag      321
Arg Pro Val Thr Asp Arg Ala Ala Ser Thr Leu Ala Gln Leu Gln Glu
    35                  40                  45

gag ggc cag gtt gag ggc caa gat gag gat atc cct cca att aca tgc      369
Glu Gly Gln Val Glu Gly Gln Asp Glu Asp Ile Pro Pro Ile Thr Cys
50                  55                  60                  65

gtg caa aat ggc ttg cgt tac cac gat agg gat gtg tgg aaa cct gaa      417
Val Gln Asn Gly Leu Arg Tyr His Asp Arg Asp Val Trp Lys Pro Glu
                70                  75                  80

cct tgt cgt atc tgt gtg tgt gat aac ggc aag gtg ctc tgc gat gat      465
Pro Cys Arg Ile Cys Val Cys Asp Asn Gly Lys Val Leu Cys Asp Asp
            85                  90                  95

gtt atc tgc gat gag aca aaa aat tgc cct ggc gct gaa gtt cct gag      513
Val Ile Cys Asp Glu Thr Lys Asn Cys Pro Gly Ala Glu Val Pro Glu
        100                 105                 110

ggc gag tgt tgc cct gtg tgc cct gat ggt tcc gag tcc cca act gat      561
Gly Glu Cys Cys Pro Val Cys Pro Asp Gly Ser Glu Ser Pro Thr Asp
    115                 120                 125

cag gaa act act ggc gtg gag ggc cca aaa gga gat act ggt cca cgt      609
Gln Glu Thr Thr Gly Val Glu Gly Pro Lys Gly Asp Thr Gly Pro Arg
130                 135                 140                 145

ggt cct agg ggt cca gca ggt cct cca ggt aga gat ggt att cca ggc      657
Gly Pro Arg Gly Pro Ala Gly Pro Pro Gly Arg Asp Gly Ile Pro Gly
                150                 155                 160

cag cct gga ttg cca gga cca cca ggc cca cct ggc cca cca gga cct      705
Gln Pro Gly Leu Pro Gly Pro Pro Gly Pro Pro Gly Pro Pro Gly Pro
            165                 170                 175

cct ggt ctt ggt gga aat ttc gct cca caa ctc tct tat ggc tat gat      753
Pro Gly Leu Gly Gly Asn Phe Ala Pro Gln Leu Ser Tyr Gly Tyr Asp
        180                 185                 190

gag aag tca aca ggt ggt att tcc gtt cca ggt cct atg gga cca tcc      801
Glu Lys Ser Thr Gly Gly Ile Ser Val Pro Gly Pro Met Gly Pro Ser
    195                 200                 205

gga cca aga ggt ctc cca ggt cct cca ggt gct cct gga cct caa ggc      849
Gly Pro Arg Gly Leu Pro Gly Pro Pro Gly Ala Pro Gly Pro Gln Gly
210                 215                 220                 225

ttt caa gga cct cca ggc gaa cca gga gaa cca ggc gct tct gga cca      897
Phe Gln Gly Pro Pro Gly Glu Pro Gly Glu Pro Gly Ala Ser Gly Pro
                230                 235                 240

atg ggc cca agg gga cca cct ggc cca cca gga aaa aat ggc gat gat      945
Met Gly Pro Arg Gly Pro Pro Gly Pro Pro Gly Lys Asn Gly Asp Asp
            245                 250                 255

ggc gaa gct gga aag cct ggt cgt cct gga gag aga ggt cct cct ggc      993
Gly Glu Ala Gly Lys Pro Gly Arg Pro Gly Glu Arg Gly Pro Pro Gly
        260                 265                 270

cca cag ggt gca aga ggc ttg cca gga act gct ggc ttg cct gga atg     1041
Pro Gln Gly Ala Arg Gly Leu Pro Gly Thr Ala Gly Leu Pro Gly Met
    275                 280                 285

aag gga cat agg ggc ttc tcc ggc ctc gat ggc gct aag ggt gat gct     1089
Lys Gly His Arg Gly Phe Ser Gly Leu Asp Gly Ala Lys Gly Asp Ala
290                 295                 300                 305

ggc cct gct gga cca aag ggc gag cca ggt tcc cct gga gaa aac ggt     1137
Gly Pro Ala Gly Pro Lys Gly Glu Pro Gly Ser Pro Gly Glu Asn Gly
                310                 315                 320

gct cct gga caa atg ggt cct cgt gga ctt cca gga gaa agg ggt cgt     1185
Ala Pro Gly Gln Met Gly Pro Arg Gly Leu Pro Gly Glu Arg Gly Arg
```

```
            325                 330                 335

cca ggc gct cca gga cca gca ggt gct agg gga aac gat ggt gca aca     1233
Pro Gly Ala Pro Gly Pro Ala Gly Ala Arg Gly Asn Asp Gly Ala Thr
        340                 345                 350

ggc gct gct ggc cct cct ggc cca act ggt cct gct ggc cct cca gga     1281
Gly Ala Ala Gly Pro Pro Gly Pro Thr Gly Pro Ala Gly Pro Pro Gly
    355                 360                 365

ttc cca ggc gca gtt gga gct aaa gga gaa gca gga cca cag ggc cct     1329
Phe Pro Gly Ala Val Gly Ala Lys Gly Glu Ala Gly Pro Gln Gly Pro
370                 375                 380                 385

agg ggt tct gaa gga cct cag ggt gtt aga ggt gaa cca ggt cct cca     1377
Arg Gly Ser Glu Gly Pro Gln Gly Val Arg Gly Glu Pro Gly Pro Pro
                390                 395                 400

ggc cca gct gga gca gct ggt cca gca gga aat cca ggt gct gat ggt     1425
Gly Pro Ala Gly Ala Ala Gly Pro Ala Gly Asn Pro Gly Ala Asp Gly
            405                 410                 415

caa cct gga gct aag ggc gct aat ggc gca cca ggt atc gca ggc gca     1473
Gln Pro Gly Ala Lys Gly Ala Asn Gly Ala Pro Gly Ile Ala Gly Ala
        420                 425                 430

cca ggt ttt cct ggc gct aga ggc cca agt ggt cct caa gga cca ggt     1521
Pro Gly Phe Pro Gly Ala Arg Gly Pro Ser Gly Pro Gln Gly Pro Gly
    435                 440                 445

gga cca cca ggt cca aaa ggc aat tct ggc gaa cct ggc gct cca ggt     1569
Gly Pro Pro Gly Pro Lys Gly Asn Ser Gly Glu Pro Gly Ala Pro Gly
450                 455                 460                 465

tct aaa gga gat act ggt gct aaa ggc gaa cca gga cct gtt ggt gtt     1617
Ser Lys Gly Asp Thr Gly Ala Lys Gly Glu Pro Gly Pro Val Gly Val
                470                 475                 480

cag ggt cct cct ggt cct gct gga gaa gaa gga aaa aga ggt gct cgt     1665
Gln Gly Pro Pro Gly Pro Ala Gly Glu Glu Gly Lys Arg Gly Ala Arg
            485                 490                 495

gga gaa cca gga cca act gga ctt cct gga cct cct ggt gaa cgt ggc     1713
Gly Glu Pro Gly Pro Thr Gly Leu Pro Gly Pro Pro Gly Glu Arg Gly
        500                 505                 510

gga cct ggc tca agg ggt ttc cct gga gct gat gga gtg gca ggt cca     1761
Gly Pro Gly Ser Arg Gly Phe Pro Gly Ala Asp Gly Val Ala Gly Pro
    515                 520                 525

aaa ggc cct gct gga gag aga ggt tca cca ggt cca gct ggt cct aag     1809
Lys Gly Pro Ala Gly Glu Arg Gly Ser Pro Gly Pro Ala Gly Pro Lys
530                 535                 540                 545

ggc tcc cct ggt gaa gca ggt aga cca ggc gaa gca gga ttg cca ggc     1857
Gly Ser Pro Gly Glu Ala Gly Arg Pro Gly Glu Ala Gly Leu Pro Gly
                550                 555                 560

gca aag gga ttg aca ggc tct cct ggt agt cct ggc cca gat gga aaa     1905
Ala Lys Gly Leu Thr Gly Ser Pro Gly Ser Pro Gly Pro Asp Gly Lys
            565                 570                 575

aca ggc cca cca ggt cca gca gga caa gat gga cgt cca ggc cca cca     1953
Thr Gly Pro Pro Gly Pro Ala Gly Gln Asp Gly Arg Pro Gly Pro Pro
        580                 585                 590

ggt cct cct gga gca agg gga caa gct ggc gtt atg ggt ttt cca gga     2001
Gly Pro Pro Gly Ala Arg Gly Gln Ala Gly Val Met Gly Phe Pro Gly
    595                 600                 605

cct aaa ggt gct gct gga gag cca gga aag gca ggt gaa aga gga gtt     2049
Pro Lys Gly Ala Ala Gly Glu Pro Gly Lys Ala Gly Glu Arg Gly Val
610                 615                 620                 625

cct ggt cca cca gga gca gtg ggt cct gct ggc aaa gat ggt gaa gct     2097
Pro Gly Pro Pro Gly Ala Val Gly Pro Ala Gly Lys Asp Gly Glu Ala
                630                 635                 640

gga gca cag ggc cct cca ggc cct gct ggc cca gct ggc gaa cgt gga     2145
```

```
Gly Ala Gln Gly Pro Pro Gly Pro Ala Gly Pro Ala Gly Glu Arg Gly
            645                 650                 655

gaa caa ggc cca gct ggt agt cca gga ttt caa gga ttg cct ggc cct      2193
Glu Gln Gly Pro Ala Gly Ser Pro Gly Phe Gln Gly Leu Pro Gly Pro
        660                 665                 670

gct ggc cct cca gga gaa gca gga aaa cct gga gaa caa gga gtt cct      2241
Ala Gly Pro Pro Gly Glu Ala Gly Lys Pro Gly Glu Gln Gly Val Pro
    675                 680                 685

ggt gat ttg gga gca cct gga cct tca gga gca cgt ggt gaa aga ggc      2289
Gly Asp Leu Gly Ala Pro Gly Pro Ser Gly Ala Arg Gly Glu Arg Gly
690                 695                 700                 705

ttc cct ggc gag agg ggt gtt caa ggt cca cca ggt cca gca gga cct      2337
Phe Pro Gly Glu Arg Gly Val Gln Gly Pro Pro Gly Pro Ala Gly Pro
                710                 715                 720

aga ggt gct aat ggc gct cct ggc aac gat gga gca aaa ggt gat gct      2385
Arg Gly Ala Asn Gly Ala Pro Gly Asn Asp Gly Ala Lys Gly Asp Ala
            725                 730                 735

ggt gct cct ggc gca cct gga agt cag ggt gct cct gga ttg caa gga      2433
Gly Ala Pro Gly Ala Pro Gly Ser Gln Gly Ala Pro Gly Leu Gln Gly
        740                 745                 750

atg cct gga gag agg ggt gct gct ggc ttg cca ggc cca aag ggc gat      2481
Met Pro Gly Glu Arg Gly Ala Ala Gly Leu Pro Gly Pro Lys Gly Asp
    755                 760                 765

agg ggt gat gct gga cca aaa ggt gct gat gga tcc cca gga aaa gat      2529
Arg Gly Asp Ala Gly Pro Lys Gly Ala Asp Gly Ser Pro Gly Lys Asp
770                 775                 780                 785

gga gtt cgt ggt ctt act ggc cca atc gga cct cca ggc cct gct ggc      2577
Gly Val Arg Gly Leu Thr Gly Pro Ile Gly Pro Pro Gly Pro Ala Gly
                790                 795                 800

gct cca ggt gat aag ggc gaa agt ggc cca agt gga cct gct gga cct      2625
Ala Pro Gly Asp Lys Gly Glu Ser Gly Pro Ser Gly Pro Ala Gly Pro
            805                 810                 815

act ggt gct aga ggt gca cct ggt gat agg ggt gaa cct gga cca cct      2673
Thr Gly Ala Arg Gly Ala Pro Gly Asp Arg Gly Glu Pro Gly Pro Pro
        820                 825                 830

ggt cca gct ggt ttt gct ggt cct cct gga gct gat gga caa cct ggc      2721
Gly Pro Ala Gly Phe Ala Gly Pro Pro Gly Ala Asp Gly Gln Pro Gly
    835                 840                 845

gca aag ggt gaa cca ggt gat gct ggc gca aag gga gat gct ggt cca      2769
Ala Lys Gly Glu Pro Gly Asp Ala Gly Ala Lys Gly Asp Ala Gly Pro
850                 855                 860                 865

cct gga cct gct ggt cca gca ggc ccc cct ggg cca atc ggt aat gtt      2817
Pro Gly Pro Ala Gly Pro Ala Gly Pro Pro Gly Pro Ile Gly Asn Val
                870                 875                 880

gga gca cca ggt gct aag gga gct agg ggt tcc gct ggt cca cct gga      2865
Gly Ala Pro Gly Ala Lys Gly Ala Arg Gly Ser Ala Gly Pro Pro Gly
            885                 890                 895

gca aca gga ttt cca ggc gct gct ggt aga gtt ggc cca cca ggc cca      2913
Ala Thr Gly Phe Pro Gly Ala Ala Gly Arg Val Gly Pro Pro Gly Pro
        900                 905                 910

tcc gga aac gca ggc cct cct ggt cct cca ggt cct gct ggc aag gag      2961
Ser Gly Asn Ala Gly Pro Pro Gly Pro Pro Gly Pro Ala Gly Lys Glu
    915                 920                 925

ggt ggc aaa gga cca agg ggc gaa act ggc cct gct ggt aga cct ggc      3009
Gly Gly Lys Gly Pro Arg Gly Glu Thr Gly Pro Ala Gly Arg Pro Gly
930                 935                 940                 945

gaa gtt ggc cct cct gga cca cca ggt cca gca gga gaa aaa ggt tcc      3057
Glu Val Gly Pro Pro Gly Pro Pro Gly Pro Ala Gly Glu Lys Gly Ser
                950                 955                 960
```

```
cca gga gct gat ggc cca gct ggt gct cca gga act cca ggc cct caa     3105
Pro Gly Ala Asp Gly Pro Ala Gly Ala Pro Gly Thr Pro Gly Pro Gln
            965                 970                 975

ggt att gct gga cag aga ggc gtt gtg gga ctc cct ggt caa agg gga     3153
Gly Ile Ala Gly Gln Arg Gly Val Val Gly Leu Pro Gly Gln Arg Gly
        980                 985                 990

gag aga gga ttt cca ggc ttg  cca gga cct agt gga  gaa cct gga aaa   3201
Glu Arg Gly Phe Pro Gly Leu  Pro Gly Pro Ser Gly  Glu Pro Gly Lys
    995                 1000                 1005

caa  ggc cca tca ggc gct  agt gga gag cgt gga  cct cct ggc cct      3246
Gln  Gly Pro Ser Gly Ala  Ser Gly Glu Arg Gly  Pro Pro Gly Pro
1010                 1015                 1020

atg  gga cct cct gga ttg  gct ggc cca cct ggc  gaa tca ggt cgt      3291
Met  Gly Pro Pro Gly Leu  Ala Gly Pro Pro Gly  Glu Ser Gly Arg
1025                 1030                 1035

gaa  ggc gca cca ggc gca  gaa gga tca cct gga  aga gat gga tcc      3336
Glu  Gly Ala Pro Gly Ala  Glu Gly Ser Pro Gly  Arg Asp Gly Ser
1040                 1045                 1050

cct  ggt gct aaa ggc gat  cgt gga gaa act ggt  cca gca ggc cca      3381
Pro  Gly Ala Lys Gly Asp  Arg Gly Glu Thr Gly  Pro Ala Gly Pro
1055                 1060                 1065

cca  ggc gca cca ggt gca  cct ggc gct cca gga  cct gtg gga cca      3426
Pro  Gly Ala Pro Gly Ala  Pro Gly Ala Pro Gly  Pro Val Gly Pro
1070                 1075                 1080

gct  gga aaa tcc gga gat  agg ggc gag aca ggc  cca gca gga cca      3471
Ala  Gly Lys Ser Gly Asp  Arg Gly Glu Thr Gly  Pro Ala Gly Pro
1085                 1090                 1095

gct  gga cct gtt ggc cct  gct ggc gct cgt gga  cca gca gga cct      3516
Ala  Gly Pro Val Gly Pro  Ala Gly Ala Arg Gly  Pro Ala Gly Pro
1100                 1105                 1110

caa  gga cca agg gga gat  aag gga gaa aca ggc  gaa caa ggc gat      3561
Gln  Gly Pro Arg Gly Asp  Lys Gly Glu Thr Gly  Glu Gln Gly Asp
1115                 1120                 1125

agg  ggc att aag ggt cat  agg ggt ttt agt ggc  ctc cag ggt cct      3606
Arg  Gly Ile Lys Gly His  Arg Gly Phe Ser Gly  Leu Gln Gly Pro
1130                 1135                 1140

cct  ggc cca cct gga tca  cca gga gaa cag gga  cca tct ggt gct      3651
Pro  Gly Pro Pro Gly Ser  Pro Gly Glu Gln Gly  Pro Ser Gly Ala
1145                 1150                 1155

tcc  ggc cca gct ggt cca  aga gga cct cca gga  tca gct ggt gca      3696
Ser  Gly Pro Ala Gly Pro  Arg Gly Pro Pro Gly  Ser Ala Gly Ala
1160                 1165                 1170

cct  gga aaa gat ggt ctt  aac ggt ctc cca gga  cca atc ggc cct      3741
Pro  Gly Lys Asp Gly Leu  Asn Gly Leu Pro Gly  Pro Ile Gly Pro
1175                 1180                 1185

cca  gga cct aga gga aga  aca gga gat gct ggc  cct gtt ggc cct      3786
Pro  Gly Pro Arg Gly Arg  Thr Gly Asp Ala Gly  Pro Val Gly Pro
1190                 1195                 1200

cca  gga cct cct ggt cca  cca ggt cca cct ggt  cct cca tca gct      3831
Pro  Gly Pro Pro Gly Pro  Pro Gly Pro Pro Gly  Pro Pro Ser Ala
1205                 1210                 1215

gga  ttc gat ttt tca ttt  ctt cca cag cca cca  caa gag aaa gct      3876
Gly  Phe Asp Phe Ser Phe  Leu Pro Gln Pro Pro  Gln Glu Lys Ala
1220                 1225                 1230

cac  gat ggc ggc aga tat  tac cgt gct gat gat  gct aac gtt gtt      3921
His  Asp Gly Gly Arg Tyr  Tyr Arg Ala Asp Asp  Ala Asn Val Val
1235                 1240                 1245

agg  gat aga gat ttg gaa  gtg gat aca act ttg  aaa tcc ctc tcc      3966
Arg  Asp Arg Asp Leu Glu  Val Asp Thr Thr Leu  Lys Ser Leu Ser
1250                 1255                 1260
```

```
cag  caa att gaa aac att  aga tct cca gaa ggt  tca cgt aaa aac      4011
Gln  Gln Ile Glu Asn Ile  Arg Ser Pro Glu Gly  Ser Arg Lys Asn
1265                 1270                 1275

cca  gct aga aca tgt cgt  gat ttg aaa atg tgt  cac tcc gat tgg      4056
Pro  Ala Arg Thr Cys Arg  Asp Leu Lys Met Cys  His Ser Asp Trp
1280                 1285                 1290

aaa  agt ggt gaa tac tgg  att gat cca aat cag  ggc tgt aat ctc      4101
Lys  Ser Gly Glu Tyr Trp  Ile Asp Pro Asn Gln  Gly Cys Asn Leu
1295                 1300                 1305

gat  gct atc aaa gtt ttc  tgt aac atg gaa aca  ggc gaa aca tgc      4146
Asp  Ala Ile Lys Val Phe  Cys Asn Met Glu Thr  Gly Glu Thr Cys
1310                 1315                 1320

gtt  tat cct act caa cct  tcc gtg gct cag aaa  aat tgg tac atc      4191
Val  Tyr Pro Thr Gln Pro  Ser Val Ala Gln Lys  Asn Trp Tyr Ile
1325                 1330                 1335

tca  aaa aat cct aaa gat  aag agg cac gtt tgg  ttc ggt gaa agt      4236
Ser  Lys Asn Pro Lys Asp  Lys Arg His Val Trp  Phe Gly Glu Ser
1340                 1345                 1350

atg  act gat gga ttt caa  ttt gag tac ggc ggt  caa ggt agt gat      4281
Met  Thr Asp Gly Phe Gln  Phe Glu Tyr Gly Gly  Gln Gly Ser Asp
1355                 1360                 1365

cca  gct gat gtg gct att  caa ctc aca ttt ttg  cgt ctt atg tcc      4326
Pro  Ala Asp Val Ala Ile  Gln Leu Thr Phe Leu  Arg Leu Met Ser
1370                 1375                 1380

aca  gag gca tca caa aac  atc act tac cac tgc  aaa aac agt gtg      4371
Thr  Glu Ala Ser Gln Asn  Ile Thr Tyr His Cys  Lys Asn Ser Val
1385                 1390                 1395

gct  tat atg gat caa caa  aca gga aac ctt aag  aag gct ctt ctt      4416
Ala  Tyr Met Asp Gln Gln  Thr Gly Asn Leu Lys  Lys Ala Leu Leu
1400                 1405                 1410

ttg  aag ggc tca aac gag  att gag att aga gca  gag ggc aac tca      4461
Leu  Lys Gly Ser Asn Glu  Ile Glu Ile Arg Ala  Glu Gly Asn Ser
1415                 1420                 1425

agg  ttt act tat tca gtt  act gtt gat ggc tgc  act tca cat act      4506
Arg  Phe Thr Tyr Ser Val  Thr Val Asp Gly Cys  Thr Ser His Thr
1430                 1435                 1440

ggc  gct tgg ggt aaa aca  gtt atc gag tat aag  act aca aaa aca      4551
Gly  Ala Trp Gly Lys Thr  Val Ile Glu Tyr Lys  Thr Thr Lys Thr
1445                 1450                 1455

tca  aga ctc cca atc att  gat gtt gct cct ctc  gat gtt ggc gct      4596
Ser  Arg Leu Pro Ile Ile  Asp Val Ala Pro Leu  Asp Val Gly Ala
1460                 1465                 1470

cct  gat caa gag ttc ggt  ttt gat gtg ggc cca  gtt tgt ttc ctc      4641
Pro  Asp Gln Glu Phe Gly  Phe Asp Val Gly Pro  Val Cys Phe Leu
1475                 1480                 1485

taa tgagctcgcg gccgcatc                                             4662


<210> SEQ ID NO 3
<211> LENGTH: 1489
<212> TYPE: PRT
<213> ORGANISM: Artificial sequence
<220> FEATURE:
<223> OTHER INFORMATION: Synthetic Construct

<400> SEQUENCE: 3

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30
```

```
Ile Arg Pro Val Thr Asp Arg Ala Ala Ser Thr Leu Ala Gln Leu Gln
        35                  40                  45

Glu Glu Gly Gln Val Glu Gly Gln Asp Glu Asp Ile Pro Pro Ile Thr
    50                  55                  60

Cys Val Gln Asn Gly Leu Arg Tyr His Asp Arg Asp Val Trp Lys Pro
65                  70                  75                  80

Glu Pro Cys Arg Ile Cys Val Cys Asp Asn Gly Lys Val Leu Cys Asp
                85                  90                  95

Asp Val Ile Cys Asp Glu Thr Lys Asn Cys Pro Gly Ala Glu Val Pro
            100                 105                 110

Glu Gly Glu Cys Cys Pro Val Cys Pro Asp Gly Ser Glu Ser Pro Thr
        115                 120                 125

Asp Gln Glu Thr Thr Gly Val Glu Gly Pro Lys Gly Asp Thr Gly Pro
    130                 135                 140

Arg Gly Pro Arg Gly Pro Ala Gly Pro Pro Gly Arg Asp Gly Ile Pro
145                 150                 155                 160

Gly Gln Pro Gly Leu Pro Gly Pro Pro Gly Pro Pro Gly Pro Pro Gly
                165                 170                 175

Pro Pro Gly Leu Gly Gly Asn Phe Ala Pro Gln Leu Ser Tyr Gly Tyr
            180                 185                 190

Asp Glu Lys Ser Thr Gly Gly Ile Ser Val Pro Gly Pro Met Gly Pro
        195                 200                 205

Ser Gly Pro Arg Gly Leu Pro Gly Pro Pro Gly Ala Pro Gly Pro Gln
    210                 215                 220

Gly Phe Gln Gly Pro Pro Gly Glu Pro Gly Glu Pro Gly Ala Ser Gly
225                 230                 235                 240

Pro Met Gly Pro Arg Gly Pro Pro Gly Pro Pro Gly Lys Asn Gly Asp
                245                 250                 255

Asp Gly Glu Ala Gly Lys Pro Gly Arg Pro Gly Glu Arg Gly Pro Pro
            260                 265                 270

Gly Pro Gln Gly Ala Arg Gly Leu Pro Gly Thr Ala Gly Leu Pro Gly
        275                 280                 285

Met Lys Gly His Arg Gly Phe Ser Gly Leu Asp Gly Ala Lys Gly Asp
    290                 295                 300

Ala Gly Pro Ala Gly Pro Lys Gly Glu Pro Gly Ser Pro Gly Glu Asn
305                 310                 315                 320

Gly Ala Pro Gly Gln Met Gly Pro Arg Gly Leu Pro Gly Glu Arg Gly
                325                 330                 335

Arg Pro Gly Ala Pro Gly Pro Ala Gly Ala Arg Gly Asn Asp Gly Ala
            340                 345                 350

Thr Gly Ala Ala Gly Pro Pro Gly Pro Thr Gly Pro Ala Gly Pro Pro
        355                 360                 365

Gly Phe Pro Gly Ala Val Gly Ala Lys Gly Glu Ala Gly Pro Gln Gly
    370                 375                 380

Pro Arg Gly Ser Glu Gly Pro Gln Gly Val Arg Gly Glu Pro Gly Pro
385                 390                 395                 400

Pro Gly Pro Ala Gly Ala Ala Gly Pro Ala Gly Asn Pro Gly Ala Asp
                405                 410                 415

Gly Gln Pro Gly Ala Lys Gly Ala Asn Gly Ala Pro Gly Ile Ala Gly
            420                 425                 430

Ala Pro Gly Phe Pro Gly Ala Arg Gly Pro Ser Gly Pro Gln Gly Pro
        435                 440                 445

Gly Gly Pro Pro Gly Pro Lys Gly Asn Ser Gly Glu Pro Gly Ala Pro
```

```
    450                 455                 460

Gly Ser Lys Gly Asp Thr Gly Ala Lys Gly Glu Pro Gly Pro Val Gly
465                 470                 475                 480

Val Gln Gly Pro Pro Gly Pro Ala Gly Glu Glu Gly Lys Arg Gly Ala
                485                 490                 495

Arg Gly Glu Pro Gly Pro Thr Gly Leu Pro Gly Pro Pro Gly Glu Arg
            500                 505                 510

Gly Gly Pro Gly Ser Arg Gly Phe Pro Gly Ala Asp Gly Val Ala Gly
        515                 520                 525

Pro Lys Gly Pro Ala Gly Glu Arg Gly Ser Pro Gly Pro Ala Gly Pro
    530                 535                 540

Lys Gly Ser Pro Gly Glu Ala Gly Arg Pro Gly Glu Ala Gly Leu Pro
545                 550                 555                 560

Gly Ala Lys Gly Leu Thr Gly Ser Pro Gly Ser Pro Gly Pro Asp Gly
                565                 570                 575

Lys Thr Gly Pro Pro Gly Pro Ala Gly Gln Asp Gly Arg Pro Gly Pro
            580                 585                 590

Pro Gly Pro Pro Gly Ala Arg Gly Gln Ala Gly Val Met Gly Phe Pro
        595                 600                 605

Gly Pro Lys Gly Ala Ala Gly Glu Pro Gly Lys Ala Gly Glu Arg Gly
    610                 615                 620

Val Pro Gly Pro Pro Gly Ala Val Gly Pro Ala Gly Lys Asp Gly Glu
625                 630                 635                 640

Ala Gly Ala Gln Gly Pro Pro Gly Pro Ala Gly Pro Ala Gly Glu Arg
                645                 650                 655

Gly Glu Gln Gly Pro Ala Gly Ser Pro Gly Phe Gln Gly Leu Pro Gly
            660                 665                 670

Pro Ala Gly Pro Pro Gly Glu Ala Gly Lys Pro Gly Glu Gln Gly Val
        675                 680                 685

Pro Gly Asp Leu Gly Ala Pro Gly Pro Ser Gly Ala Arg Gly Glu Arg
    690                 695                 700

Gly Phe Pro Gly Glu Arg Gly Val Gln Gly Pro Pro Gly Pro Ala Gly
705                 710                 715                 720

Pro Arg Gly Ala Asn Gly Ala Pro Gly Asn Asp Gly Ala Lys Gly Asp
                725                 730                 735

Ala Gly Ala Pro Gly Ala Pro Gly Ser Gln Gly Ala Pro Gly Leu Gln
            740                 745                 750

Gly Met Pro Gly Glu Arg Gly Ala Ala Gly Leu Pro Gly Pro Lys Gly
        755                 760                 765

Asp Arg Gly Asp Ala Gly Pro Lys Gly Ala Asp Gly Ser Pro Gly Lys
    770                 775                 780

Asp Gly Val Arg Gly Leu Thr Gly Pro Ile Gly Pro Pro Gly Pro Ala
785                 790                 795                 800

Gly Ala Pro Gly Asp Lys Gly Glu Ser Gly Pro Ser Gly Pro Ala Gly
                805                 810                 815

Pro Thr Gly Ala Arg Gly Ala Pro Gly Asp Arg Gly Glu Pro Gly Pro
            820                 825                 830

Pro Gly Pro Ala Gly Phe Ala Gly Pro Pro Gly Ala Asp Gly Gln Pro
        835                 840                 845

Gly Ala Lys Gly Glu Pro Gly Asp Ala Gly Ala Lys Gly Asp Ala Gly
    850                 855                 860

Pro Pro Gly Pro Ala Gly Pro Ala Gly Pro Pro Gly Pro Ile Gly Asn
865                 870                 875                 880
```

-continued

```
Val Gly Ala Pro Gly Ala Lys Gly Ala Arg Gly Ser Ala Gly Pro Pro
                885                 890                 895

Gly Ala Thr Gly Phe Pro Gly Ala Ala Gly Arg Val Gly Pro Pro Gly
            900                 905                 910

Pro Ser Gly Asn Ala Gly Pro Pro Gly Pro Pro Gly Pro Ala Gly Lys
        915                 920                 925

Glu Gly Gly Lys Gly Pro Arg Gly Glu Thr Gly Pro Ala Gly Arg Pro
    930                 935                 940

Gly Glu Val Gly Pro Pro Gly Pro Pro Gly Pro Ala Gly Glu Lys Gly
945                 950                 955                 960

Ser Pro Gly Ala Asp Gly Pro Ala Gly Ala Pro Gly Thr Pro Gly Pro
                965                 970                 975

Gln Gly Ile Ala Gly Gln Arg Gly Val Val Gly Leu Pro Gly Gln Arg
            980                 985                 990

Gly Glu Arg Gly Phe Pro Gly Leu  Pro Gly Pro Ser Gly  Glu Pro Gly
        995                 1000                1005

Lys Gln  Gly Pro Ser Gly Ala  Ser Gly Glu Arg Gly  Pro Pro Gly
    1010                1015                1020

Pro Met  Gly Pro Pro Gly Leu  Ala Gly Pro Pro Gly  Glu Ser Gly
    1025                1030                1035

Arg Glu  Gly Ala Pro Gly Ala  Glu Gly Ser Pro Gly  Arg Asp Gly
    1040                1045                1050

Ser Pro  Gly Ala Lys Gly Asp  Arg Gly Glu Thr Gly  Pro Ala Gly
    1055                1060                1065

Pro Pro  Gly Ala Pro Gly Ala  Pro Gly Ala Pro Gly  Pro Val Gly
    1070                1075                1080

Pro Ala  Gly Lys Ser Gly Asp  Arg Gly Glu Thr Gly  Pro Ala Gly
    1085                1090                1095

Pro Ala  Gly Pro Val Gly Pro  Ala Gly Ala Arg Gly  Pro Ala Gly
    1100                1105                1110

Pro Gln  Gly Pro Arg Gly Asp  Lys Gly Glu Thr Gly  Glu Gln Gly
    1115                1120                1125

Asp Arg  Gly Ile Lys Gly His  Arg Gly Phe Ser Gly  Leu Gln Gly
    1130                1135                1140

Pro Pro  Gly Pro Pro Gly Ser  Pro Gly Glu Gln Gly  Pro Ser Gly
    1145                1150                1155

Ala Ser  Gly Pro Ala Gly Pro  Arg Gly Pro Pro Gly  Ser Ala Gly
    1160                1165                1170

Ala Pro  Gly Lys Asp Gly Leu  Asn Gly Leu Pro Gly  Pro Ile Gly
    1175                1180                1185

Pro Pro  Gly Pro Arg Gly Arg  Thr Gly Asp Ala Gly  Pro Val Gly
    1190                1195                1200

Pro Pro  Gly Pro Pro Gly Pro  Pro Gly Pro Pro Gly  Pro Pro Ser
    1205                1210                1215

Ala Gly  Phe Asp Phe Ser Phe  Leu Pro Gln Pro Pro  Gln Glu Lys
    1220                1225                1230

Ala His  Asp Gly Gly Arg Tyr  Tyr Arg Ala Asp Asp  Ala Asn Val
    1235                1240                1245

Val Arg  Asp Arg Asp Leu Glu  Val Asp Thr Thr Leu  Lys Ser Leu
    1250                1255                1260

Ser Gln  Gln Ile Glu Asn Ile  Arg Ser Pro Glu Gly  Ser Arg Lys
    1265                1270                1275
```

```
Asn Pro  Ala Arg Thr Cys Arg  Asp Leu Lys Met Cys  His Ser Asp
    1280                 1285                 1290

Trp Lys  Ser Gly Glu Tyr Trp  Ile Asp Pro Asn Gln  Gly Cys Asn
    1295                 1300                 1305

Leu Asp  Ala Ile Lys Val Phe  Cys Asn Met Glu Thr  Gly Glu Thr
    1310                 1315                 1320

Cys Val  Tyr Pro Thr Gln Pro  Ser Val Ala Gln Lys  Asn Trp Tyr
    1325                 1330                 1335

Ile Ser  Lys Asn Pro Lys Asp  Lys Arg His Val Trp  Phe Gly Glu
    1340                 1345                 1350

Ser Met  Thr Asp Gly Phe Gln  Phe Glu Tyr Gly Gly  Gln Gly Ser
    1355                 1360                 1365

Asp Pro  Ala Asp Val Ala Ile  Gln Leu Thr Phe Leu  Arg Leu Met
    1370                 1375                 1380

Ser Thr  Glu Ala Ser Gln Asn  Ile Thr Tyr His Cys  Lys Asn Ser
    1385                 1390                 1395

Val Ala  Tyr Met Asp Gln Gln  Thr Gly Asn Leu Lys  Lys Ala Leu
    1400                 1405                 1410

Leu Leu  Lys Gly Ser Asn Glu  Ile Glu Ile Arg Ala  Glu Gly Asn
    1415                 1420                 1425

Ser Arg  Phe Thr Tyr Ser Val  Thr Val Asp Gly Cys  Thr Ser His
    1430                 1435                 1440

Thr Gly  Ala Trp Gly Lys Thr  Val Ile Glu Tyr Lys  Thr Thr Lys
    1445                 1450                 1455

Thr Ser  Arg Leu Pro Ile Ile  Asp Val Ala Pro Leu  Asp Val Gly
    1460                 1465                 1470

Ala Pro  Asp Gln Glu Phe Gly  Phe Asp Val Gly Pro  Val Cys Phe
    1475                 1480                 1485

Leu


<210> SEQ ID NO 4
<211> LENGTH: 4362
<212> TYPE: DNA
<213> ORGANISM: Artificial sequence
<220> FEATURE:
<223> OTHER INFORMATION: Synthetic sequence containing the coding
      regions of the vacuolar signal sequence of barley gene for Thiol
      protease aleurain precursor fused to the human Collagen alpha 2(I)
      chain and flanking regions

<400> SEQUENCE: 4

gcgatgcatg taatgtcatg agccacatga tccaatggcc acaggaacgt aagaatgtag      60

atagatttga ttttgtccgt tagatagcaa acaacattat aaaaggtgtg tatcaatacg     120

aactaattca ctcattggat tcatagaagt ccattcctcc taagtatcta aaccatggct     180

cacgctcgtg ttctcctcct cgctctcgct gttttggcaa cagctgctgt ggctgtggct     240

tcaagttcta gttttgctga ttccaaccca attcgtccag ttactgatag agcagcttcc     300

actttggctc aattgcttca agaagaaact gtgaggaagg gccctgctgg cgataggggc     360

cctaggggcg aaaggggtcc accaggacct ccaggcaggg atggcgaaga tggtccaact     420

ggccctcctg gacctcctgg ccctccaggg ccacccggct tgggcggaaa cttcgcagct     480

caatacgatg gcaagggtgt tggtcttggt cctggtccta tgggcttgat gggacctaga     540

ggcccacctg gtgctgctgg tgctcctgga ccacagggtt ttcagggacc agctggcgag     600

ccaggagagc caggccaaac aggaccagct ggtgcaaggg gacctgctgg acctcctgga     660
```

```
aaagctggtg aagatggtca cccaggcaaa ccaggacgtc ctggcgaaag aggtgttgtt    720
ggaccacaag gcgctagggg atttccaggt acacctggat tgccaggttt taagggcatt    780
cgtggtcata acggcctcga tggattgaag ggacagcctg gcgcacctgg cgttaagggt    840
gaacctggag caccaggtga aaacggtact cctggccaga ctggtgcaag aggactccca    900
ggtgaaaggg gtagagttgg tgctcctgga cctgctggag ctaggggtag tgatggtagt    960
gttggtcctg tgggccctgc tggtccaatc ggttccgctg gcccacctgg attcccaggc   1020
gctccaggac ctaaaggaga aatcggtgct gtgggtaacg caggtcctac tggtccagca   1080
ggtcctcgtg gagaagtggg attgccagga ctttctggtc cagtgggccc tccaggcaac   1140
cctggagcta acggcttgac aggagctaaa ggcgcagcag gactccctgg agtggctggc   1200
gcaccaggat tgcctggtcc aaggggtatc ccaggccctg ttggcgcagc tggagctact   1260
ggtgcacgtg gacttgttgg cgaaccaggc cctgctggat caaaaggcga gtctggaaat   1320
aagggagaac ctggttctgc tggacctcaa ggtcctcctg gaccttctgg agaagaagga   1380
aaaaggggac caaatggcga ggctggatca gcaggtccac caggaccacc tggacttcgt   1440
ggatcccctg gtagtagagg acttccaggc gctgatggta gagcaggcgt tatgggacca   1500
ccaggaagta gaggagcatc cggtccagca ggagttaggg gtcctaacgg agatgctggt   1560
agaccaggtg aaccaggtct tatgggccca aggggcctcc caggtagtcc aggaaatatc   1620
ggccctgctg gaaaagaagg ccctgttgga cttccaggta ttgatggacg tcctggccct   1680
attggcccag caggtgcaag aggagaacct ggcaatattg gatttccagg accaaagggt   1740
ccaacaggcg atcctggaaa aaatggagat aagggtcatg ctggattggc aggcgcaagg   1800
ggcgctcctg gtccagatgg aaacaacggc gcacagggtc cacctggccc tcagggtgtt   1860
caaggcggaa aaggcgaaca aggcccagct ggaccaccag gctttcaagg cttgccagga   1920
ccaagtggtc cagcaggtga agttggcaag ccaggcgagc gtggacttca tggcgagttt   1980
ggactccctg gaccagcagg accaaggggt gaaagaggcc ctcctggaga gagtggcgct   2040
gctggaccaa caggcccaat cggtagtaga ggtcctagtg gacctccagg cccagatgga   2100
aataagggtg aaccaggagt tgtgggcgct gttggaacag ctggtccttc aggaccatca   2160
ggactcccag gcgagagagg cgctgctggc attcctggag gaaaaggtga aaaaggcgaa   2220
cctggcctcc gtggcgaaat cggaaatcct ggacgtgatg gtgctcgtgg tgcacacggc   2280
gctgtgggcg ctccaggccc tgctggtgct actggtgata gaggagaggc tggcgcagct   2340
ggcccagcag gtcctgctgg cccaaggggt agtcctggtg aaagaggcga agttggacct   2400
gctggcccta acggctttgc tggccctgct ggagcagcag gtcaacctgg cgctaaaggt   2460
gaaaggggcg gaaagggccc aaaaggtgaa aatggcgttg tgggaccaac tggtccagtg   2520
ggcgcagctg gacctgctgg tccaaatgga ccaccaggac cagcaggtag tagaggagat   2580
ggtggacctc caggaatgac aggttttcca ggtgctgctg gtagaacagg acctcctggt   2640
cctagtggta tttctggtcc accaggacca ccaggtcctg ctggaaaaga aggattgagg   2700
ggtccacgtg gtgatcaagg accagtgggc agaactggtg aagttggcgc agtgggacca   2760
cctggttttg ctggagaaaa gggcccttct ggagaggcag gaacagctgg tcctcctggt   2820
acacctggac ctcaaggact tttgggtgca cctggtattc tcggattgcc aggaagtagg   2880
ggcgaacgtg gacttcctgg cgtggcagga gcagttggag aacctggccc tctcggaatc   2940
gcaggcccac caggcgcaag aggaccacca ggagctgttg gatcaccagg cgtgaatggt   3000
gcacctggcg aggctggtcg tgatggaaac ccaggaaatg atggcccacc aggaagagat   3060
```

```
ggtcaacctg gacacaaagg cgagaggggc tacccaggaa atattggccc agttggtgct   3120

gctggcgcac caggcccaca cggtccagtt ggaccagcag gaaaacacgg taatcgtggc   3180

gaaacaggcc cttcaggccc agtgggacct gctggtgctg ttggcccaag aggaccatct   3240

ggacctcaag gcattagagg cgataaggga gagcctggcg aaaaaggacc tagaggcttg   3300

cctggtttta aggacacaa cggtctccaa ggacttccag gtatcgctgg tcatcatgga   3360

gatcagggtg ctcctggatc agtgggtcca gcaggtccta gaggcccagc aggcccttcc   3420

ggtccagcag gaaaggatgg acgtactggc caccctggaa ctgtgggccc tgctggaatt   3480

agaggtcctc aaggtcatca gggccctgct ggccctccag gtccaccagg tcctccaggc   3540

ccaccaggag tttcaggtgg tggttacgat tttggttacg atggtgattt ttaccgtgct   3600

gatcaaccta gaagtgctcc ttctctccgt cctaaagatt atgaagttga tgctactttg   3660

aaatcactta acaaccagat tgagactctt ctcacacctg agggatcaag aaagaatcca   3720

gcacgtacat gccgtgatct cagacttagt cacccagagt ggtcaagtgg ctattattgg   3780

attgatccta atcagggttg tacaatggag gctatcaaag tttactgtga ttttccaact   3840

ggagagacat gtattagggc acaacctgag aacattccag ctaaaaattg gtatcgttcc   3900

tctaaagata agaaacatgt ttggctcgga gagactatta acgctggttc tcagttcgag   3960

tataatgttg agggcgttac ttctaaagag atggcaactc agctcgcttt tatgagattg   4020

ctcgctaact acgcatccca aaacatcact tatcactgca aaaattccat tgcatatatg   4080

gatgaggaga caggaaattt gaagaaagca gttattctcc aaggtagtaa cgatgttgag   4140

cttgtggctg agggaaatag tagattcact tacacagttt tggtggatgg atgctcaaag   4200

aaaactaatg agtggggcaa gacaatcatt gagtacaaga caaataagcc ttctaggctc   4260

ccatttctcg atattgcacc tcttgatatc ggaggagctg atcacgagtt ttttgttgat   4320

atcggacctg tttgttttaa gtaatgagct cgcggccgca tc                       4362
```

```
<210> SEQ ID NO 5
<211> LENGTH: 4362
<212> TYPE: DNA
<213> ORGANISM: Artificial sequence
<220> FEATURE:
<223> OTHER INFORMATION: Synthetic sequence of the vacuolar signal
      sequence of barley gene for Thiol protease aleurain precursor
      fused to the human Collagen alpha 2(I) chain and flanking regions
<220> FEATURE:
<221> NAME/KEY: CDS
<222> LOCATION: (175)..(4344)

<400> SEQUENCE: 5

gcgatgcatg taatgtcatg agccacatga tccaatggcc acaggaacgt aagaatgtag     60

atagatttga ttttgtccgt tagatagcaa acaacattat aaaaggtgtg tatcaatacg    120

aactaattca ctcattggat tcatagaagt ccattcctcc taagtatcta aacc atg      177
                                                            Met
                                                            1

gct cac gct cgt gtt ctc ctc ctc gct ctc gct gtt ttg gca aca gct      225
Ala His Ala Arg Val Leu Leu Leu Ala Leu Ala Val Leu Ala Thr Ala
            5                   10                  15

gct gtg gct gtg gct tca agt tct agt ttt gct gat tcc aac cca att      273
Ala Val Ala Val Ala Ser Ser Ser Ser Phe Ala Asp Ser Asn Pro Ile
        20                  25                  30

cgt cca gtt act gat aga gca gct tcc act ttg gct caa ttg ctt caa      321
Arg Pro Val Thr Asp Arg Ala Ala Ser Thr Leu Ala Gln Leu Leu Gln
    35                  40                  45
```

```
gaa gaa act gtg agg aag ggc cct gct ggc gat agg ggc cct agg ggc      369
Glu Glu Thr Val Arg Lys Gly Pro Ala Gly Asp Arg Gly Pro Arg Gly
50                  55                  60                  65

gaa agg ggt cca cca gga cct cca ggc agg gat ggc gaa gat ggt cca      417
Glu Arg Gly Pro Pro Gly Pro Pro Gly Arg Asp Gly Glu Asp Gly Pro
                70                  75                  80

act ggc cct cct gga cct cct ggc cct cca ggg cca ccc ggc ttg ggc      465
Thr Gly Pro Pro Gly Pro Pro Gly Pro Pro Gly Pro Pro Gly Leu Gly
            85                  90                  95

gga aac ttc gca gct caa tac gat ggc aag ggt gtt ggt ctt ggt cct      513
Gly Asn Phe Ala Ala Gln Tyr Asp Gly Lys Gly Val Gly Leu Gly Pro
        100                 105                 110

ggt cct atg ggc ttg atg gga cct aga ggc cca cct ggt gct gct ggt      561
Gly Pro Met Gly Leu Met Gly Pro Arg Gly Pro Pro Gly Ala Ala Gly
    115                 120                 125

gct cct gga cca cag ggt ttt cag gga cca gct ggc gag cca gga gag      609
Ala Pro Gly Pro Gln Gly Phe Gln Gly Pro Ala Gly Glu Pro Gly Glu
130                 135                 140                 145

cca ggc caa aca gga cca gct ggt gca agg gga cct gct gga cct cct      657
Pro Gly Gln Thr Gly Pro Ala Gly Ala Arg Gly Pro Ala Gly Pro Pro
                150                 155                 160

gga aaa gct ggt gaa gat ggt cac cca ggc aaa cca gga cgt cct ggc      705
Gly Lys Ala Gly Glu Asp Gly His Pro Gly Lys Pro Gly Arg Pro Gly
            165                 170                 175

gaa aga ggt gtt gtt gga cca caa ggc gct agg gga ttt cca ggt aca      753
Glu Arg Gly Val Val Gly Pro Gln Gly Ala Arg Gly Phe Pro Gly Thr
        180                 185                 190

cct gga ttg cca ggt ttt aag ggc att cgt ggt cat aac ggc ctc gat      801
Pro Gly Leu Pro Gly Phe Lys Gly Ile Arg Gly His Asn Gly Leu Asp
    195                 200                 205

gga ttg aag gga cag cct ggc gca cct ggc gtt aag ggt gaa cct gga      849
Gly Leu Lys Gly Gln Pro Gly Ala Pro Gly Val Lys Gly Glu Pro Gly
210                 215                 220                 225

gca cca ggt gaa aac ggt act cct ggc cag act ggt gca aga gga ctc      897
Ala Pro Gly Glu Asn Gly Thr Pro Gly Gln Thr Gly Ala Arg Gly Leu
                230                 235                 240

cca ggt gaa agg ggt aga gtt ggt gct cct gga cct gct gga gct agg      945
Pro Gly Glu Arg Gly Arg Val Gly Ala Pro Gly Pro Ala Gly Ala Arg
            245                 250                 255

ggt agt gat ggt agt gtt ggt cct gtg ggc cct gct ggt cca atc ggt      993
Gly Ser Asp Gly Ser Val Gly Pro Val Gly Pro Ala Gly Pro Ile Gly
        260                 265                 270

tcc gct ggc cca cct gga ttc cca ggc gct cca gga cct aaa gga gaa     1041
Ser Ala Gly Pro Pro Gly Phe Pro Gly Ala Pro Gly Pro Lys Gly Glu
    275                 280                 285

atc ggt gct gtg ggt aac gca ggt cct act ggt cca gca ggt cct cgt     1089
Ile Gly Ala Val Gly Asn Ala Gly Pro Thr Gly Pro Ala Gly Pro Arg
290                 295                 300                 305

gga gaa gtg gga ttg cca gga ctt tct ggt cca gtg ggc cct cca ggc     1137
Gly Glu Val Gly Leu Pro Gly Leu Ser Gly Pro Val Gly Pro Pro Gly
                310                 315                 320

aac cct gga gct aac ggc ttg aca gga gct aaa ggc gca gca gga ctc     1185
Asn Pro Gly Ala Asn Gly Leu Thr Gly Ala Lys Gly Ala Ala Gly Leu
            325                 330                 335

cct gga gtg gct ggc gca cca gga ttg cct ggt cca agg ggt atc cca     1233
Pro Gly Val Ala Gly Ala Pro Gly Leu Pro Gly Pro Arg Gly Ile Pro
        340                 345                 350

ggc cct gtt ggc gca gct gga gct act ggt gca cgt gga ctt gtt ggc     1281
Gly Pro Val Gly Ala Ala Gly Ala Thr Gly Ala Arg Gly Leu Val Gly
```

```
    355                 360                 365

gaa cca ggc cct gct gga tca aaa ggc gag tct gga aat aag gga gaa      1329
Glu Pro Gly Pro Ala Gly Ser Lys Gly Glu Ser Gly Asn Lys Gly Glu
370                 375                 380                 385

cct ggt tct gct gga cct caa ggt cct cct gga cct tct gga gaa gaa      1377
Pro Gly Ser Ala Gly Pro Gln Gly Pro Pro Gly Pro Ser Gly Glu Glu
                390                 395                 400

gga aaa agg gga cca aat ggc gag gct gga tca gca ggt cca cca gga      1425
Gly Lys Arg Gly Pro Asn Gly Glu Ala Gly Ser Ala Gly Pro Pro Gly
            405                 410                 415

cca cct gga ctt cgt gga tcc cct ggt agt aga gga ctt cca ggc gct      1473
Pro Pro Gly Leu Arg Gly Ser Pro Gly Ser Arg Gly Leu Pro Gly Ala
        420                 425                 430

gat ggt aga gca ggc gtt atg gga cca cca gga agt aga gga gca tcc      1521
Asp Gly Arg Ala Gly Val Met Gly Pro Pro Gly Ser Arg Gly Ala Ser
    435                 440                 445

ggt cca gca gga gtt agg ggt cct aac gga gat gct ggt aga cca ggt      1569
Gly Pro Ala Gly Val Arg Gly Pro Asn Gly Asp Ala Gly Arg Pro Gly
450                 455                 460                 465

gaa cca ggt ctt atg ggc cca agg ggc ctc cca ggt agt cca gga aat      1617
Glu Pro Gly Leu Met Gly Pro Arg Gly Leu Pro Gly Ser Pro Gly Asn
                470                 475                 480

atc ggc cct gct gga aaa gaa ggc cct gtt gga ctt cca ggt att gat      1665
Ile Gly Pro Ala Gly Lys Glu Gly Pro Val Gly Leu Pro Gly Ile Asp
            485                 490                 495

gga cgt cct ggc cct att ggc cca gca ggt gca aga gga gaa cct ggc      1713
Gly Arg Pro Gly Pro Ile Gly Pro Ala Gly Ala Arg Gly Glu Pro Gly
        500                 505                 510

aat att gga ttt cca gga cca aag ggt cca aca ggc gat cct gga aaa      1761
Asn Ile Gly Phe Pro Gly Pro Lys Gly Pro Thr Gly Asp Pro Gly Lys
    515                 520                 525

aat gga gat aag ggt cat gct gga ttg gca ggc gca agg ggc gct cct      1809
Asn Gly Asp Lys Gly His Ala Gly Leu Ala Gly Ala Arg Gly Ala Pro
530                 535                 540                 545

ggt cca gat gga aac aac ggc gca cag ggt cca cct ggc cct cag ggt      1857
Gly Pro Asp Gly Asn Asn Gly Ala Gln Gly Pro Pro Gly Pro Gln Gly
                550                 555                 560

gtt caa ggc gga aaa ggc gaa caa ggc cca gct gga cca cca ggc ttt      1905
Val Gln Gly Gly Lys Gly Glu Gln Gly Pro Ala Gly Pro Pro Gly Phe
            565                 570                 575

caa ggc ttg cca gga cca agt ggt cca gca ggt gaa gtt ggc aag cca      1953
Gln Gly Leu Pro Gly Pro Ser Gly Pro Ala Gly Glu Val Gly Lys Pro
        580                 585                 590

ggc gag cgt gga ctt cat ggc gag ttt gga ctc cct gga cca gca gga      2001
Gly Glu Arg Gly Leu His Gly Glu Phe Gly Leu Pro Gly Pro Ala Gly
    595                 600                 605

cca agg ggt gaa aga ggc cct cct gga gag agt ggc gct gct gga cca      2049
Pro Arg Gly Glu Arg Gly Pro Pro Gly Glu Ser Gly Ala Ala Gly Pro
610                 615                 620                 625

aca ggc cca atc ggt agt aga ggt cct agt gga cct cca ggc cca gat      2097
Thr Gly Pro Ile Gly Ser Arg Gly Pro Ser Gly Pro Pro Gly Pro Asp
                630                 635                 640

gga aat aag ggt gaa cca gga gtt gtg ggc gct gtt gga aca gct ggt      2145
Gly Asn Lys Gly Glu Pro Gly Val Val Gly Ala Val Gly Thr Ala Gly
            645                 650                 655

cct tca gga cca tca gga ctc cca ggc gag aga ggc gct gct ggc att      2193
Pro Ser Gly Pro Ser Gly Leu Pro Gly Glu Arg Gly Ala Ala Gly Ile
        660                 665                 670

cct gga gga aaa ggt gaa aaa ggc gaa cct ggc ctc cgt ggc gaa atc      2241
```

```
Pro Gly Gly Lys Gly Glu Lys Gly Glu Pro Gly Leu Arg Gly Glu Ile
    675                 680                 685

gga aat cct gga cgt gat ggt gct cgt ggt gca cac ggc gct gtg ggc      2289
Gly Asn Pro Gly Arg Asp Gly Ala Arg Gly Ala His Gly Ala Val Gly
690                 695                 700                 705

gct cca ggc cct gct ggt gct act ggt gat aga gga gag gct ggc gca      2337
Ala Pro Gly Pro Ala Gly Ala Thr Gly Asp Arg Gly Glu Ala Gly Ala
                710                 715                 720

gct ggc cca gca ggt cct gct ggc cca agg ggt agt cct ggt gaa aga      2385
Ala Gly Pro Ala Gly Pro Ala Gly Pro Arg Gly Ser Pro Gly Glu Arg
            725                 730                 735

ggc gaa gtt gga cct gct ggc cct aac ggc ttt gct ggc cct gct gga      2433
Gly Glu Val Gly Pro Ala Gly Pro Asn Gly Phe Ala Gly Pro Ala Gly
        740                 745                 750

gca gca ggt caa cct ggc gct aaa ggt gaa agg ggc gga aag ggc cca      2481
Ala Ala Gly Gln Pro Gly Ala Lys Gly Glu Arg Gly Gly Lys Gly Pro
    755                 760                 765

aaa ggt gaa aat ggc gtt gtg gga cca act ggt cca gtg ggc gca gct      2529
Lys Gly Glu Asn Gly Val Val Gly Pro Thr Gly Pro Val Gly Ala Ala
770                 775                 780                 785

gga cct gct ggt cca aat gga cca cca gga cca gca ggt agt aga gga      2577
Gly Pro Ala Gly Pro Asn Gly Pro Pro Gly Pro Ala Gly Ser Arg Gly
                790                 795                 800

gat ggt gga cct cca gga atg aca ggt ttt cca ggt gct gct ggt aga      2625
Asp Gly Gly Pro Pro Gly Met Thr Gly Phe Pro Gly Ala Ala Gly Arg
            805                 810                 815

aca gga cct cct ggt cct agt ggt att tct ggt cca cca gga cca cca      2673
Thr Gly Pro Pro Gly Pro Ser Gly Ile Ser Gly Pro Pro Gly Pro Pro
        820                 825                 830

ggt cct gct gga aaa gaa gga ttg agg ggt cca cgt ggt gat caa gga      2721
Gly Pro Ala Gly Lys Glu Gly Leu Arg Gly Pro Arg Gly Asp Gln Gly
    835                 840                 845

cca gtg ggc aga act ggt gaa gtt ggc gca gtg gga cca cct ggt ttt      2769
Pro Val Gly Arg Thr Gly Glu Val Gly Ala Val Gly Pro Pro Gly Phe
850                 855                 860                 865

gct gga gaa aag ggc cct tct gga gag gca gga aca gct ggt cct cct      2817
Ala Gly Glu Lys Gly Pro Ser Gly Glu Ala Gly Thr Ala Gly Pro Pro
                870                 875                 880

ggt aca cct gga cct caa gga ctt ttg ggt gca cct ggt att ctc gga      2865
Gly Thr Pro Gly Pro Gln Gly Leu Leu Gly Ala Pro Gly Ile Leu Gly
            885                 890                 895

ttg cca gga agt agg ggc gaa cgt gga ctt cct ggc gtg gca gga gca      2913
Leu Pro Gly Ser Arg Gly Glu Arg Gly Leu Pro Gly Val Ala Gly Ala
        900                 905                 910

gtt gga gaa cct ggc cct ctc gga atc gca ggc cca cca ggc gca aga      2961
Val Gly Glu Pro Gly Pro Leu Gly Ile Ala Gly Pro Pro Gly Ala Arg
    915                 920                 925

gga cca cca gga gct gtt gga tca cca ggc gtg aat ggt gca cct ggc      3009
Gly Pro Pro Gly Ala Val Gly Ser Pro Gly Val Asn Gly Ala Pro Gly
930                 935                 940                 945

gag gct ggt cgt gat gga aac cca gga aat gat ggc cca cca gga aga      3057
Glu Ala Gly Arg Asp Gly Asn Pro Gly Asn Asp Gly Pro Pro Gly Arg
                950                 955                 960

gat ggt caa cct gga cac aaa ggc gag agg ggc tac cca gga aat att      3105
Asp Gly Gln Pro Gly His Lys Gly Glu Arg Gly Tyr Pro Gly Asn Ile
            965                 970                 975

ggc cca gtt ggt gct gct ggc gca cca ggc cca cac ggt cca gtt gga      3153
Gly Pro Val Gly Ala Ala Gly Ala Pro Gly Pro His Gly Pro Val Gly
        980                 985                 990
```

```
cca gca gga aaa cac ggt aat  cgt ggc gaa aca ggc  cct tca ggc cca    3201
Pro Ala Gly Lys His Gly Asn  Arg Gly Glu Thr Gly  Pro Ser Gly Pro
    995                 1000                 1005

gtg  gga cct gct ggt gct  gtt ggc cca aga gga  cca tct gga cct      3246
Val  Gly Pro Ala Gly Ala  Val Gly Pro Arg Gly  Pro Ser Gly Pro
1010                 1015                 1020

caa  ggc att aga ggc gat  aag gga gag cct ggc  gaa aaa gga cct      3291
Gln  Gly Ile Arg Gly Asp  Lys Gly Glu Pro Gly  Glu Lys Gly Pro
1025                 1030                 1035

aga  ggc ttg cct ggt ttt  aaa gga cac aac ggt  ctc caa gga ctt      3336
Arg  Gly Leu Pro Gly Phe  Lys Gly His Asn Gly  Leu Gln Gly Leu
1040                 1045                 1050

cca  ggt atc gct ggt cat  cat gga gat cag ggt  gct cct gga tca      3381
Pro  Gly Ile Ala Gly His  His Gly Asp Gln Gly  Ala Pro Gly Ser
1055                 1060                 1065

gtg  ggt cca gca ggt cct  aga ggc cca gca ggc  cct tcc ggt cca      3426
Val  Gly Pro Ala Gly Pro  Arg Gly Pro Ala Gly  Pro Ser Gly Pro
1070                 1075                 1080

gca  gga aag gat gga cgt  act ggc cac cct gga  act gtg ggc cct      3471
Ala  Gly Lys Asp Gly Arg  Thr Gly His Pro Gly  Thr Val Gly Pro
1085                 1090                 1095

gct  gga att aga ggt cct  caa ggt cat cag ggc  cct gct ggc cct      3516
Ala  Gly Ile Arg Gly Pro  Gln Gly His Gln Gly  Pro Ala Gly Pro
1100                 1105                 1110

cca  ggt cca cca ggt cct  cca ggc cca cca gga  gtt tca ggt ggt      3561
Pro  Gly Pro Pro Gly Pro  Pro Gly Pro Pro Gly  Val Ser Gly Gly
1115                 1120                 1125

ggt  tac gat ttt ggt tac  gat ggt gat ttt tac  cgt gct gat caa      3606
Gly  Tyr Asp Phe Gly Tyr  Asp Gly Asp Phe Tyr  Arg Ala Asp Gln
1130                 1135                 1140

cct  aga agt gct cct tct  ctc cgt cct aaa gat  tat gaa gtt gat      3651
Pro  Arg Ser Ala Pro Ser  Leu Arg Pro Lys Asp  Tyr Glu Val Asp
1145                 1150                 1155

gct  act ttg aaa tca ctt  aac aac cag att gag  act ctt ctc aca      3696
Ala  Thr Leu Lys Ser Leu  Asn Asn Gln Ile Glu  Thr Leu Leu Thr
1160                 1165                 1170

cct  gag gga tca aga aag  aat cca gca cgt aca  tgc cgt gat ctc      3741
Pro  Glu Gly Ser Arg Lys  Asn Pro Ala Arg Thr  Cys Arg Asp Leu
1175                 1180                 1185

aga  ctt agt cac cca gag  tgg tca agt ggc tat  tat tgg att gat      3786
Arg  Leu Ser His Pro Glu  Trp Ser Ser Gly Tyr  Tyr Trp Ile Asp
1190                 1195                 1200

cct  aat cag ggt tgt aca  atg gag gct atc aaa  gtt tac tgt gat      3831
Pro  Asn Gln Gly Cys Thr  Met Glu Ala Ile Lys  Val Tyr Cys Asp
1205                 1210                 1215

ttt  cca act gga gag aca  tgt att agg gca caa  cct gag aac att      3876
Phe  Pro Thr Gly Glu Thr  Cys Ile Arg Ala Gln  Pro Glu Asn Ile
1220                 1225                 1230

cca  gct aaa aat tgg tat  cgt tcc tct aaa gat  aag aaa cat gtt      3921
Pro  Ala Lys Asn Trp Tyr  Arg Ser Ser Lys Asp  Lys Lys His Val
1235                 1240                 1245

tgg  ctc gga gag act att  aac gct ggt tct cag  ttc gag tat aat      3966
Trp  Leu Gly Glu Thr Ile  Asn Ala Gly Ser Gln  Phe Glu Tyr Asn
1250                 1255                 1260

gtt  gag ggc gtt act tct  aaa gag atg gca act  cag ctc gct ttt      4011
Val  Glu Gly Val Thr Ser  Lys Glu Met Ala Thr  Gln Leu Ala Phe
1265                 1270                 1275

atg  aga ttg ctc gct aac  tac gca tcc caa aac  atc act tat cac      4056
Met  Arg Leu Leu Ala Asn  Tyr Ala Ser Gln Asn  Ile Thr Tyr His
1280                 1285                 1290
```

```
tgc  aaa aat tcc att gca  tat atg gat gag gag  aca gga aat ttg      4101
Cys  Lys Asn Ser Ile Ala  Tyr Met Asp Glu Glu  Thr Gly Asn Leu
1295                 1300                 1305

aag  aaa gca gtt att ctc  caa ggt agt aac gat  gtt gag ctt gtg      4146
Lys  Lys Ala Val Ile Leu  Gln Gly Ser Asn Asp  Val Glu Leu Val
1310                 1315                 1320

gct  gag gga aat agt aga  ttc act tac aca gtt  ttg gtg gat gga      4191
Ala  Glu Gly Asn Ser Arg  Phe Thr Tyr Thr Val  Leu Val Asp Gly
1325                 1330                 1335

tgc  tca aag aaa act aat  gag tgg ggc aag aca  atc att gag tac      4236
Cys  Ser Lys Lys Thr Asn  Glu Trp Gly Lys Thr  Ile Ile Glu Tyr
1340                 1345                 1350

aag  aca aat aag cct tct  agg ctc cca ttt ctc  gat att gca cct      4281
Lys  Thr Asn Lys Pro Ser  Arg Leu Pro Phe Leu  Asp Ile Ala Pro
1355                 1360                 1365

ctt  gat atc gga gga gct  gat cac gag ttt ttt  gtt gat atc gga      4326
Leu  Asp Ile Gly Gly Ala  Asp His Glu Phe Phe  Val Asp Ile Gly
1370                 1375                 1380

cct  gtt tgt ttt aag taa tgagctcgcg gccgcatc                        4362
Pro  Val Cys Phe Lys
1385


<210> SEQ ID NO 6
<211> LENGTH: 1389
<212> TYPE: PRT
<213> ORGANISM: Artificial sequence
<220> FEATURE:
<223> OTHER INFORMATION: Synthetic Construct

<400> SEQUENCE: 6

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala Gln Leu Leu
        35                  40                  45

Gln Glu Glu Thr Val Arg Lys Gly Pro Ala Gly Asp Arg Gly Pro Arg
    50                  55                  60

Gly Glu Arg Gly Pro Pro Gly Pro Pro Gly Arg Asp Gly Glu Asp Gly
65                  70                  75                  80

Pro Thr Gly Pro Pro Gly Pro Pro Gly Pro Pro Gly Pro Pro Gly Leu
                85                  90                  95

Gly Gly Asn Phe Ala Ala Gln Tyr Asp Gly Lys Gly Val Gly Leu Gly
            100                 105                 110

Pro Gly Pro Met Gly Leu Met Gly Pro Arg Gly Pro Pro Gly Ala Ala
        115                 120                 125

Gly Ala Pro Gly Pro Gln Gly Phe Gln Gly Pro Ala Gly Glu Pro Gly
    130                 135                 140

Glu Pro Gly Gln Thr Gly Pro Ala Gly Ala Arg Gly Pro Ala Gly Pro
145                 150                 155                 160

Pro Gly Lys Ala Gly Glu Asp Gly His Pro Gly Lys Pro Gly Arg Pro
                165                 170                 175

Gly Glu Arg Gly Val Val Gly Pro Gln Gly Ala Arg Gly Phe Pro Gly
            180                 185                 190

Thr Pro Gly Leu Pro Gly Phe Lys Gly Ile Arg Gly His Asn Gly Leu
        195                 200                 205

Asp Gly Leu Lys Gly Gln Pro Gly Ala Pro Gly Val Lys Gly Glu Pro
```

```
    210                 215                 220

Gly Ala Pro Gly Glu Asn Gly Thr Pro Gly Gln Thr Gly Ala Arg Gly
225                 230                 235                 240

Leu Pro Gly Glu Arg Gly Arg Val Gly Ala Pro Gly Pro Ala Gly Ala
                245                 250                 255

Arg Gly Ser Asp Gly Ser Val Gly Pro Val Gly Pro Ala Gly Pro Ile
            260                 265                 270

Gly Ser Ala Gly Pro Pro Gly Phe Pro Gly Ala Pro Gly Pro Lys Gly
        275                 280                 285

Glu Ile Gly Ala Val Gly Asn Ala Gly Pro Thr Gly Pro Ala Gly Pro
    290                 295                 300

Arg Gly Glu Val Gly Leu Pro Gly Leu Ser Gly Pro Val Gly Pro Pro
305                 310                 315                 320

Gly Asn Pro Gly Ala Asn Gly Leu Thr Gly Ala Lys Gly Ala Ala Gly
                325                 330                 335

Leu Pro Gly Val Ala Gly Ala Pro Gly Leu Pro Gly Pro Arg Gly Ile
            340                 345                 350

Pro Gly Pro Val Gly Ala Ala Gly Ala Thr Gly Ala Arg Gly Leu Val
        355                 360                 365

Gly Glu Pro Gly Pro Ala Gly Ser Lys Gly Glu Ser Gly Asn Lys Gly
    370                 375                 380

Glu Pro Gly Ser Ala Gly Pro Gln Gly Pro Pro Gly Pro Ser Gly Glu
385                 390                 395                 400

Glu Gly Lys Arg Gly Pro Asn Gly Glu Ala Gly Ser Ala Gly Pro Pro
                405                 410                 415

Gly Pro Pro Gly Leu Arg Gly Ser Pro Gly Ser Arg Gly Leu Pro Gly
            420                 425                 430

Ala Asp Gly Arg Ala Gly Val Met Gly Pro Pro Gly Ser Arg Gly Ala
        435                 440                 445

Ser Gly Pro Ala Gly Val Arg Gly Pro Asn Gly Asp Ala Gly Arg Pro
    450                 455                 460

Gly Glu Pro Gly Leu Met Gly Pro Arg Gly Leu Pro Gly Ser Pro Gly
465                 470                 475                 480

Asn Ile Gly Pro Ala Gly Lys Glu Gly Pro Val Gly Leu Pro Gly Ile
                485                 490                 495

Asp Gly Arg Pro Gly Pro Ile Gly Pro Ala Gly Ala Arg Gly Glu Pro
            500                 505                 510

Gly Asn Ile Gly Phe Pro Gly Pro Lys Gly Pro Thr Gly Asp Pro Gly
        515                 520                 525

Lys Asn Gly Asp Lys Gly His Ala Gly Leu Ala Gly Ala Arg Gly Ala
    530                 535                 540

Pro Gly Pro Asp Gly Asn Asn Gly Ala Gln Gly Pro Pro Gly Pro Gln
545                 550                 555                 560

Gly Val Gln Gly Gly Lys Gly Glu Gln Gly Pro Ala Gly Pro Pro Gly
                565                 570                 575

Phe Gln Gly Leu Pro Gly Pro Ser Gly Pro Ala Gly Glu Val Gly Lys
            580                 585                 590

Pro Gly Glu Arg Gly Leu His Gly Glu Phe Gly Leu Pro Gly Pro Ala
        595                 600                 605

Gly Pro Arg Gly Glu Arg Gly Pro Pro Gly Glu Ser Gly Ala Ala Gly
    610                 615                 620

Pro Thr Gly Pro Ile Gly Ser Arg Gly Pro Ser Gly Pro Pro Gly Pro
625                 630                 635                 640
```

```
Asp Gly Asn Lys Gly Glu Pro Gly Val Val Gly Ala Val Gly Thr Ala
                645                 650                 655

Gly Pro Ser Gly Pro Ser Gly Leu Pro Gly Glu Arg Gly Ala Ala Gly
            660                 665                 670

Ile Pro Gly Gly Lys Gly Glu Lys Gly Glu Pro Gly Leu Arg Gly Glu
        675                 680                 685

Ile Gly Asn Pro Gly Arg Asp Gly Ala Arg Gly Ala His Gly Ala Val
    690                 695                 700

Gly Ala Pro Gly Pro Ala Gly Ala Thr Gly Asp Arg Gly Glu Ala Gly
705                 710                 715                 720

Ala Ala Gly Pro Ala Gly Pro Ala Gly Pro Arg Gly Ser Pro Gly Glu
                725                 730                 735

Arg Gly Glu Val Gly Pro Ala Gly Pro Asn Gly Phe Ala Gly Pro Ala
            740                 745                 750

Gly Ala Ala Gly Gln Pro Gly Ala Lys Gly Glu Arg Gly Gly Lys Gly
        755                 760                 765

Pro Lys Gly Glu Asn Gly Val Val Gly Pro Thr Gly Pro Val Gly Ala
    770                 775                 780

Ala Gly Pro Ala Gly Pro Asn Gly Pro Pro Gly Pro Ala Gly Ser Arg
785                 790                 795                 800

Gly Asp Gly Gly Pro Pro Gly Met Thr Gly Phe Pro Gly Ala Ala Gly
                805                 810                 815

Arg Thr Gly Pro Pro Gly Pro Ser Gly Ile Ser Gly Pro Pro Gly Pro
            820                 825                 830

Pro Gly Pro Ala Gly Lys Glu Gly Leu Arg Gly Pro Arg Gly Asp Gln
        835                 840                 845

Gly Pro Val Gly Arg Thr Gly Glu Val Gly Ala Val Gly Pro Pro Gly
    850                 855                 860

Phe Ala Gly Glu Lys Gly Pro Ser Gly Glu Ala Gly Thr Ala Gly Pro
865                 870                 875                 880

Pro Gly Thr Pro Gly Pro Gln Gly Leu Leu Gly Ala Pro Gly Ile Leu
                885                 890                 895

Gly Leu Pro Gly Ser Arg Gly Glu Arg Gly Leu Pro Gly Val Ala Gly
            900                 905                 910

Ala Val Gly Glu Pro Gly Pro Leu Gly Ile Ala Gly Pro Pro Gly Ala
        915                 920                 925

Arg Gly Pro Pro Gly Ala Val Gly Ser Pro Gly Val Asn Gly Ala Pro
    930                 935                 940

Gly Glu Ala Gly Arg Asp Gly Asn Pro Gly Asn Asp Gly Pro Pro Gly
945                 950                 955                 960

Arg Asp Gly Gln Pro Gly His Lys Gly Glu Arg Gly Tyr Pro Gly Asn
                965                 970                 975

Ile Gly Pro Val Gly Ala Ala Gly Ala Pro Gly Pro His Gly Pro Val
            980                 985                 990

Gly Pro Ala Gly Lys His Gly Asn  Arg Gly Glu Thr Gly  Pro Ser Gly
        995                 1000                1005

Pro Val  Gly Pro Ala Gly Ala  Val Gly Pro Arg Gly  Pro Ser Gly
    1010                1015                1020

Pro Gln  Gly Ile Arg Gly Asp  Lys Gly Glu Pro Gly  Glu Lys Gly
    1025                1030                1035

Pro Arg  Gly Leu Pro Gly Phe  Lys Gly His Asn Gly  Leu Gln Gly
    1040                1045                1050
```

```
Leu Pro  Gly Ile Ala Gly His  His Gly Asp Gln Gly  Ala Pro Gly
    1055                 1060                 1065

Ser Val  Gly Pro Ala Gly Pro  Arg Gly Pro Ala Gly  Pro Ser Gly
    1070                 1075                 1080

Pro Ala  Gly Lys Asp Gly Arg  Thr Gly His Pro Gly  Thr Val Gly
    1085                 1090                 1095

Pro Ala  Gly Ile Arg Gly Pro  Gln Gly His Gln Gly  Pro Ala Gly
    1100                 1105                 1110

Pro Pro  Gly Pro Pro Gly Pro  Pro Gly Pro Pro Gly  Val Ser Gly
    1115                 1120                 1125

Gly Gly  Tyr Asp Phe Gly Tyr  Asp Gly Asp Phe Tyr  Arg Ala Asp
    1130                 1135                 1140

Gln Pro  Arg Ser Ala Pro Ser  Leu Arg Pro Lys Asp  Tyr Glu Val
    1145                 1150                 1155

Asp Ala  Thr Leu Lys Ser Leu  Asn Asn Gln Ile Glu  Thr Leu Leu
    1160                 1165                 1170

Thr Pro  Glu Gly Ser Arg Lys  Asn Pro Ala Arg Thr  Cys Arg Asp
    1175                 1180                 1185

Leu Arg  Leu Ser His Pro Glu  Trp Ser Ser Gly Tyr  Tyr Trp Ile
    1190                 1195                 1200

Asp Pro  Asn Gln Gly Cys Thr  Met Glu Ala Ile Lys  Val Tyr Cys
    1205                 1210                 1215

Asp Phe  Pro Thr Gly Glu Thr  Cys Ile Arg Ala Gln  Pro Glu Asn
    1220                 1225                 1230

Ile Pro  Ala Lys Asn Trp Tyr  Arg Ser Ser Lys Asp  Lys Lys His
    1235                 1240                 1245

Val Trp  Leu Gly Glu Thr Ile  Asn Ala Gly Ser Gln  Phe Glu Tyr
    1250                 1255                 1260

Asn Val  Glu Gly Val Thr Ser  Lys Glu Met Ala Thr  Gln Leu Ala
    1265                 1270                 1275

Phe Met  Arg Leu Leu Ala Asn  Tyr Ala Ser Gln Asn  Ile Thr Tyr
    1280                 1285                 1290

His Cys  Lys Asn Ser Ile Ala  Tyr Met Asp Glu Glu  Thr Gly Asn
    1295                 1300                 1305

Leu Lys  Lys Ala Val Ile Leu  Gln Gly Ser Asn Asp  Val Glu Leu
    1310                 1315                 1320

Val Ala  Glu Gly Asn Ser Arg  Phe Thr Tyr Thr Val  Leu Val Asp
    1325                 1330                 1335

Gly Cys  Ser Lys Lys Thr Asn  Glu Trp Gly Lys Thr  Ile Ile Glu
    1340                 1345                 1350

Tyr Lys  Thr Asn Lys Pro Ser  Arg Leu Pro Phe Leu  Asp Ile Ala
    1355                 1360                 1365

Pro Leu  Asp Ile Gly Gly Ala  Asp His Glu Phe Phe  Val Asp Ile
    1370                 1375                 1380

Gly Pro  Val Cys Phe Lys
    1385
```

<210> SEQ ID NO 7
<211> LENGTH: 127
<212> TYPE: DNA
<213> ORGANISM: Artificial sequence
<220> FEATURE:
<223> OTHER INFORMATION: Synthetic sequence containing the coding region of the appoplast signal of Arabidopsis thaliana endo-1,4-beta-glucanase and flanking regions

<400> SEQUENCE: 7

```
gccatggcta ggaagtcttt gattttccca gtgattcttc ttgctgtgct tcttttctct     60

ccacctattt actctgctgg acacgattat agggatgctc ttaggaagtc atctatggct    120

caattgc                                                              127
```

<210> SEQ ID NO 8
<211> LENGTH: 127
<212> TYPE: DNA
<213> ORGANISM: Artificial sequence
<220> FEATURE:
<223> OTHER INFORMATION: Synthetic sequence of the appoplast signal of Arabidopsis thaliana endo-1,4-beta-glucanase and flanking regions
<220> FEATURE:
<221> NAME/KEY: CDS
<222> LOCATION: (10)..(120)

<400> SEQUENCE: 8

```
gccatggct agg aag tct ttg att ttc cca gtg att ctt ctt gct gtg ctt      51
          Arg Lys Ser Leu Ile Phe Pro Val Ile Leu Leu Ala Val Leu
          1               5                   10

ctt ttc tct cca cct att tac tct gct gga cac gat tat agg gat gct       99
Leu Phe Ser Pro Pro Ile Tyr Ser Ala Gly His Asp Tyr Arg Asp Ala
15                  20                  25                  30

ctt agg aag tca tct atg gct caattgc                                  127
Leu Arg Lys Ser Ser Met Ala
                35
```

<210> SEQ ID NO 9
<211> LENGTH: 37
<212> TYPE: PRT
<213> ORGANISM: Artificial sequence
<220> FEATURE:
<223> OTHER INFORMATION: Synthetic Construct

<400> SEQUENCE: 9

```
Arg Lys Ser Leu Ile Phe Pro Val Ile Leu Leu Ala Val Leu Leu Phe
1               5                   10                  15

Ser Pro Pro Ile Tyr Ser Ala Gly His Asp Tyr Arg Asp Ala Leu Arg
            20                  25                  30

Lys Ser Ser Met Ala
        35
```

<210> SEQ ID NO 10
<211> LENGTH: 1037
<212> TYPE: DNA
<213> ORGANISM: Artificial sequence
<220> FEATURE:
<223> OTHER INFORMATION: Chrysanthemum rbcS1 promoter and 5' UTR

<400> SEQUENCE: 10

```
aaatggcgcg ccaagcttag acaaacaccc cttgttatac aaagaatttc gctttacaaa     60

atcaaattcg agaaaataat atatgcacta aataagatca ttcggatcca atctaaccaa    120

ttacgatacg ctttgggtac acttgatttt tgtttcagta gttacatata tcttgtttta    180

tatgctatct ttaaggatct tcactcaaag actatttgtt gatgttcttg atggggctcg    240

gaagatttga tatgatacac tctaatcttt aggagatacc agccaggatt atattcagta    300

agacaatcaa attttacgtg ttcaaactcg ttatcttttc atttaatgga tgagccagaa    360

tctctataga atgattgcaa tcgagaatat gttcggccga tatccctttg ttggcttcaa    420

tattctacat atcacacaag aatcgaccgt attgtaccct ctttccataa aggaacacac    480
```

```
agtatgcaga tgcttttttc ccacatgcag taacataggt attcaaaaat ggctaaaaga    540

agttggataa caaattgaca actatttcca tttctgttat ataaatttca caacacacaa    600

aagcccgtaa tcaagagtct gcccatgtac gaaataactt ctattatttg gtattgggcc    660

taagcccagc tcagagtacg tgggggtacc acatatagga aggtaacaaa atactgcaag    720

atagccccat aacgtaccag cctctcctta ccacgaagag ataagatata agacccaccc    780

tgccacgtgt cacatcgtca tggtggttaa tgataaggga ttacatcctt ctatgtttgt    840

ggacatgatg catgtaatgt catgagccac atgatccaat ggccacagga acgtaagaat    900

gtagatagat ttgattttgt ccgttagata gcaaacaaca ttataaaagg tgtgtatcaa    960

tacgaactaa ttcactcatt ggattcatag aagtccattc ctcctaagta tctaaacata   1020

tgcaattgtc gactaaa                                                  1037


<210> SEQ ID NO 11
<211> LENGTH: 975
<212> TYPE: DNA
<213> ORGANISM: Artificial sequence
<220> FEATURE:
<223> OTHER INFORMATION: Chrysanthemum rbcS1  3'UTR and terminator

<400> SEQUENCE: 11

aaaaggatcc gcggccgcat aagttttact atttaccaag acttttgaat attaaccttc     60

ttgtaacgag tcggttaaat ttgattgttt agggttttgt attatttttt tttggtcttt    120

taattcatca ctttaattcc ctaattgtct gttcatttcg ttgtttgttt ccggatcgat    180

aatgaaatgt aagagatatc atatataaat aataaattgt cgtttcatat ttgcaatctt    240

tttttacaaa cctttaatta attgtatgta tgacattttc ttcttgttat attaggggga    300

aataatgtta aataaaagta caaaataaac tacagtacat cgtactgaat aaattaccta    360

gccaaaaagt acacctttcc atatacttcc tacatgaagg cattttcaac attttcaaat    420

aaggaatgct acaaccgcat aataacatcc acaaattttt ttataaaata acatgtcaga    480

cagtgattga aagattttat tatagtttcg ttatcttctt ttctcattaa gcgaatcact    540

acctaacacg tcattttgtg aaatattttt tgaatgtttt tatatagttg tagcattcct    600

cttttcaaat tagggtttgt ttgagatagc atttcagccg gttcatacaa cttaaaagca    660

tactctaatg ctggaaaaaa gactaaaaaa tcttgtaagt tagcgcagaa tattgaccca    720

aattatatac acacatgacc ccatatagag actaattaca cttttaacca ctaataatta    780

ttactgtatt ataacatcta ctaattaaac ttgtgagttt ttgctagaat tattatcata    840

tatactaaaa ggcaggaacg caaacattgc cccggtactg tagcaactac ggtagacgca    900

ttaattgtct atagtggacg cattaattaa ccaaaaccgc ctctttcccc ttcttcttga    960

agcttgagct ctttt                                                     975


<210> SEQ ID NO 12
<211> LENGTH: 1633
<212> TYPE: DNA
<213> ORGANISM: Artificial sequence
<220> FEATURE:
<223> OTHER INFORMATION: Synthetic sequence containing the coding
      regions of the vacuolar signal sequence of barley gene for Thiol
      protease aleurain precursor fused to the human Prolyl
      4-hydroxylase beta subunit and flanking regions

<400> SEQUENCE: 12

ctcgagtaaa ccatggctca tgctagggtt ttgcttttgg ctcttgctgt tcttgctact     60
```

```
gctgctgttg ctgtggcttc ttcttcatct ttcgctgatt ctaacccaat taggccagtg    120

actgatagag ctgcttctac tcttgctcaa ttggtcgaca tggatgctcc agaagaggag    180

gatcacgttc ttgtgcttag gaagtctaac ttcgctgaag ctcttgctgc tcacaagtac    240

cttcttgtgg agttttatgc tccttggtgc ggacattgca aagctcttgc tccagagtat    300

gctaaggctg ctggaaagtt gaaggctgag ggatctgaaa ttaggcttgc taaagtggat    360

gctactgagg agtctgatct tgctcaacag tacggagtta ggggataccc aactattaag    420

ttcttcagga acggagatac tgcttctcca aaggagtata ctgctggaag ggaggctgat    480

gatattgtga actggcttaa gaagagaact ggaccagctg ctactactct tccagatgga    540

gctgctgctg aatctcttgt ggagtcatct gaggtggcag tgattggatt cttcaaggat    600

gtggagtctg attctgctaa gcagttcctt caagctgctg aggctattga tgatattcca    660

ttcggaatta cttctaactc tgatgtgttc tctaagtacc agcttgataa ggatggagtg    720

gtgcttttca agaaattcga tgagggaagg aacaatttcg agggagaggt gacaaaggag    780

aaccttcttg atttcattaa gcacaaccag cttccacttg tgattgagtt cactgagcag    840

actgctccaa agattttcgg aggagagatt aagactcaca ttcttctttt ccttccaaag    900

tctgtgtctg attacgatgg aaagttgtct aacttcaaga ctgctgctga gtctttcaag    960

ggaaagattc ttttcatttt cattgattct gatcacactg ataaccagag gattcttgag   1020

ttcttcggac ttaagaagga agagtgccca gctgttaggc ttattactct tgaggaggag   1080

atgactaagt acaagccaga gtctgaagaa cttactgctg agaggattac tgagttctgc   1140

cacagattcc ttgagggaaa gattaagcca caccttatgt ctcaagagct tccagaggat   1200

tgggataagc agccagttaa ggtgttggtg ggtaaaaact tcgaggatgt ggctttcgat   1260

gagaagaaga acgtgttcgt ggagttctac gcaccttggt gtggtcactg taagcagctt   1320

gctccaattt gggataagtt gggagagact tacaaggatc acgagaacat tgtgattgct   1380

aagatggatt ctactgctaa cgaggtggag gctgttaagg ttcactcttt cccaactttg   1440

aagttcttcc cagcttctgc tgataggact gtgattgatt acaacggaga aaggactctt   1500

gatggattca agaagttcct tgagtctgga ggacaagatg gagctggaga tgatgatgat   1560

cttgaggatt tggaagaagc tgaggagcca gatatggagg aggatgatga tcagaaggct   1620

gtgtgatgag ctc                                                      1633
```

<210> SEQ ID NO 13
<211> LENGTH: 537
<212> TYPE: PRT
<213> ORGANISM: Artificial sequence
<220> FEATURE:
<223> OTHER INFORMATION: Synthetic sequence containing the vacuolar signal sequence of barley gene for Thiol protease aleurain precursor fused to the human Prolyl 4-hydroxylase beta subunit and flanking regions

<400> SEQUENCE: 13

```
Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala Gln Leu Val
        35                  40                  45

Asp Met Asp Ala Pro Glu Glu Glu Asp His Val Leu Val Leu Arg Lys
    50                  55                  60
```

```
Ser Asn Phe Ala Glu Ala Leu Ala Ala His Lys Tyr Leu Leu Val Glu
65                  70                  75                  80

Phe Tyr Ala Pro Trp Cys Gly His Cys Lys Ala Leu Ala Pro Glu Tyr
                85                  90                  95

Ala Lys Ala Ala Gly Lys Leu Lys Ala Glu Gly Ser Glu Ile Arg Leu
            100                 105                 110

Ala Lys Val Asp Ala Thr Glu Glu Ser Asp Leu Ala Gln Gln Tyr Gly
        115                 120                 125

Val Arg Gly Tyr Pro Thr Ile Lys Phe Phe Arg Asn Gly Asp Thr Ala
    130                 135                 140

Ser Pro Lys Glu Tyr Thr Ala Gly Arg Glu Ala Asp Asp Ile Val Asn
145                 150                 155                 160

Trp Leu Lys Lys Arg Thr Gly Pro Ala Ala Thr Thr Leu Pro Asp Gly
                165                 170                 175

Ala Ala Ala Glu Ser Leu Val Glu Ser Ser Glu Val Ala Val Ile Gly
            180                 185                 190

Phe Phe Lys Asp Val Glu Ser Asp Ser Ala Lys Gln Phe Leu Gln Ala
        195                 200                 205

Ala Glu Ala Ile Asp Asp Ile Pro Phe Gly Ile Thr Ser Asn Ser Asp
    210                 215                 220

Val Phe Ser Lys Tyr Gln Leu Asp Lys Asp Gly Val Val Leu Phe Lys
225                 230                 235                 240

Lys Phe Asp Glu Gly Arg Asn Asn Phe Glu Gly Glu Val Thr Lys Glu
                245                 250                 255

Asn Leu Leu Asp Phe Ile Lys His Asn Gln Leu Pro Leu Val Ile Glu
            260                 265                 270

Phe Thr Glu Gln Thr Ala Pro Lys Ile Phe Gly Gly Glu Ile Lys Thr
        275                 280                 285

His Ile Leu Leu Phe Leu Pro Lys Ser Val Ser Asp Tyr Asp Gly Lys
    290                 295                 300

Leu Ser Asn Phe Lys Thr Ala Ala Glu Ser Phe Lys Gly Lys Ile Leu
305                 310                 315                 320

Phe Ile Phe Ile Asp Ser Asp His Thr Asp Asn Gln Arg Ile Leu Glu
                325                 330                 335

Phe Phe Gly Leu Lys Lys Glu Glu Cys Pro Ala Val Arg Leu Ile Thr
            340                 345                 350

Leu Glu Glu Glu Met Thr Lys Tyr Lys Pro Glu Ser Glu Glu Leu Thr
        355                 360                 365

Ala Glu Arg Ile Thr Glu Phe Cys His Arg Phe Leu Glu Gly Lys Ile
    370                 375                 380

Lys Pro His Leu Met Ser Gln Glu Leu Pro Glu Asp Trp Asp Lys Gln
385                 390                 395                 400

Pro Val Lys Val Leu Val Gly Lys Asn Phe Glu Asp Val Ala Phe Asp
                405                 410                 415

Glu Lys Lys Asn Val Phe Val Glu Phe Tyr Ala Pro Trp Cys Gly His
            420                 425                 430

Cys Lys Gln Leu Ala Pro Ile Trp Asp Lys Leu Gly Glu Thr Tyr Lys
        435                 440                 445

Asp His Glu Asn Ile Val Ile Ala Lys Met Asp Ser Thr Ala Asn Glu
    450                 455                 460

Val Glu Ala Val Lys Val His Ser Phe Pro Thr Leu Lys Phe Phe Pro
465                 470                 475                 480

Ala Ser Ala Asp Arg Thr Val Ile Asp Tyr Asn Gly Glu Arg Thr Leu
```

```
                485                 490                 495

Asp Gly Phe Lys Lys Phe Leu Glu Ser Gly Gly Gln Asp Gly Ala Gly
            500                 505                 510

Asp Asp Asp Asp Leu Glu Asp Leu Glu Glu Ala Glu Glu Pro Asp Met
        515                 520                 525

Glu Glu Asp Asp Asp Gln Lys Ala Val
    530                 535
```

```
<210> SEQ ID NO 14
<211> LENGTH: 1723
<212> TYPE: DNA
<213> ORGANISM: Artificial sequence
<220> FEATURE:
<223> OTHER INFORMATION: Synthetic sequence containing the coding
      regions of the vacuolar signal sequence of barley gene for Thiol
      protease aleurain precursor fused to the human Prolyl
      4-hydroxylase alpha-1 subunit and flanking regions

<400> SEQUENCE: 14

ctcgagtaaa ccatggctca tgctagggtt ttgcttttgg ctcttgctgt tcttgctact     60

gctgctgttg ctgtggcttc ttcttcatct ttcgctgatt ctaacccaat taggccagtg    120

actgatagag ctgcttctac tcttgctcaa ttggtcgaca tgcacccagg attcttcact    180

tctattggac agatgactga tcttattcac actgagaagg atcttgtgac ttctcttaag    240

gattacatta aggctgagga ggataagttg gagcagatta agaagtgggc tgagaagttg    300

gataggctta cttctactgc tacaaaagat ccagagggat tcgttggtca tccagtgaac    360

gctttcaagt tgatgaagag gcttaacact gagtggagtg agcttgagaa ccttgtgctt    420

aaggatatgt ctgatggatt catttctaac cttactattc agaggcagta cttcccaaat    480

gatgaggatc aagtgggagc tgctaaggct cttcttaggc ttcaggatac ttacaacctt    540

gatactgata caatttctaa gggaaacctt ccaggagtta agcacaagtc tttccttact    600

gctgaggatt gcttcgagct tggaaaggtt gcatacactg aggctgatta ctaccacact    660

gagctttgga tggaacaagc tcttaggcaa cttgatgagg gagagatttc tactattgat    720

aaggtgtcag tgcttgatta cctttcttac gctgtgtacc agcagggtga tcttgataag    780

gctcttttgc ttactaagaa gttgcttgag cttgatccag aacatcagag ggctaacgga    840

aaccttaagt acttcgagta cattatggct aaggaaaagg atgtgaacaa gtctgcttct    900

gatgatcagt ctgatcaaaa gactactcca aagaagaagg gagtggctgt tgattatctt    960

cctgagaggc agaagtatga gatgttgtgt aggggagagg gtattaagat gactccaagg   1020

aggcagaaga agttgttctg caggtatcac gatggaaaca ggaacccaaa gttcattctt   1080

gctccagcta agcaagaaga tgagtgggat aagccaagga ttattaggtt ccacgatatt   1140

atttctgatg ctgagattga gattgtgaag gatcttgcta agccaagact taggagggct   1200

actatttcta accctattac tggtgatctt gagactgtgc actacaggat ttctaagtct   1260

gcttggcttt ctggatacga gaacccagtg gtgtctagga ttaacatgag gattcaggat   1320

cttactggac ttgatgtgtc tactgctgag gagcttcaag ttgctaacta cggagttgga   1380

ggacaatatg agccacactt cgatttcgct aggaaggatg agccagatgc ttttaaggag   1440

cttggaactg gaaacaggat tgctacttgg cttttctaca tgtctgatgt ttctgctgga   1500

ggagctactg ttttcccaga agtgggagct tctgtttggc caaagaaggg aactgctgtg   1560

ttctggtaca accttttcgc ttctggagag ggagattact ctactaggca tgctgcttgc   1620

ccagttcttg ttggaaacaa gtgggtgtca aacaagtggc ttcatgagag gggacaagag   1680
```

```
tttagaaggc catgcactct ttctgagctt gagtgatgag ctc                    1723


<210> SEQ ID NO 15
<211> LENGTH: 567
<212> TYPE: PRT
<213> ORGANISM: Artificial sequence
<220> FEATURE:
<223> OTHER INFORMATION: Synthetic sequence containing the vacuolar
      signal sequence of barley gene for Thiol protease aleurain
      precursor fused to the human Prolyl 4-hydroxylase alpha-1 subunit
      and flanking regions

<400> SEQUENCE: 15

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala Gln Leu Val
        35                  40                  45

Asp Met His Pro Gly Phe Phe Thr Ser Ile Gly Gln Met Thr Asp Leu
    50                  55                  60

Ile His Thr Glu Lys Asp Leu Val Thr Ser Leu Lys Asp Tyr Ile Lys
65                  70                  75                  80

Ala Glu Glu Asp Lys Leu Glu Gln Ile Lys Lys Trp Ala Glu Lys Leu
                85                  90                  95

Asp Arg Leu Thr Ser Thr Ala Thr Lys Asp Pro Glu Gly Phe Val Gly
            100                 105                 110

His Pro Val Asn Ala Phe Lys Leu Met Lys Arg Leu Asn Thr Glu Trp
        115                 120                 125

Ser Glu Leu Glu Asn Leu Val Leu Lys Asp Met Ser Asp Gly Phe Ile
    130                 135                 140

Ser Asn Leu Thr Ile Gln Arg Gln Tyr Phe Pro Asn Asp Glu Asp Gln
145                 150                 155                 160

Val Gly Ala Ala Lys Ala Leu Leu Arg Leu Gln Asp Thr Tyr Asn Leu
                165                 170                 175

Asp Thr Asp Thr Ile Ser Lys Gly Asn Leu Pro Gly Val Lys His Lys
            180                 185                 190

Ser Phe Leu Thr Ala Glu Asp Cys Phe Glu Leu Gly Lys Val Ala Tyr
        195                 200                 205

Thr Glu Ala Asp Tyr Tyr His Thr Glu Leu Trp Met Glu Gln Ala Leu
    210                 215                 220

Arg Gln Leu Asp Glu Gly Glu Ile Ser Thr Ile Asp Lys Val Ser Val
225                 230                 235                 240

Leu Asp Tyr Leu Ser Tyr Ala Val Tyr Gln Gln Gly Asp Leu Asp Lys
                245                 250                 255

Ala Leu Leu Leu Thr Lys Lys Leu Leu Glu Leu Asp Pro Glu His Gln
            260                 265                 270

Arg Ala Asn Gly Asn Leu Lys Tyr Phe Glu Tyr Ile Met Ala Lys Glu
        275                 280                 285

Lys Asp Val Asn Lys Ser Ala Ser Asp Asp Gln Ser Asp Gln Lys Thr
    290                 295                 300

Thr Pro Lys Lys Lys Gly Val Ala Val Asp Tyr Leu Pro Glu Arg Gln
305                 310                 315                 320

Lys Tyr Glu Met Leu Cys Arg Gly Glu Gly Ile Lys Met Thr Pro Arg
                325                 330                 335
```

```
Arg Gln Lys Lys Leu Phe Cys Arg Tyr His Asp Gly Asn Arg Asn Pro
            340                 345                 350

Lys Phe Ile Leu Ala Pro Ala Lys Gln Glu Asp Glu Trp Asp Lys Pro
        355                 360                 365

Arg Ile Ile Arg Phe His Asp Ile Ile Ser Asp Ala Glu Ile Glu Ile
    370                 375                 380

Val Lys Asp Leu Ala Lys Pro Arg Leu Arg Arg Ala Thr Ile Ser Asn
385                 390                 395                 400

Pro Ile Thr Gly Asp Leu Glu Thr Val His Tyr Arg Ile Ser Lys Ser
                405                 410                 415

Ala Trp Leu Ser Gly Tyr Glu Asn Pro Val Val Ser Arg Ile Asn Met
            420                 425                 430

Arg Ile Gln Asp Leu Thr Gly Leu Asp Val Ser Thr Ala Glu Glu Leu
        435                 440                 445

Gln Val Ala Asn Tyr Gly Val Gly Gly Gln Tyr Glu Pro His Phe Asp
    450                 455                 460

Phe Ala Arg Lys Asp Glu Pro Asp Ala Phe Lys Glu Leu Gly Thr Gly
465                 470                 475                 480

Asn Arg Ile Ala Thr Trp Leu Phe Tyr Met Ser Asp Val Ser Ala Gly
                485                 490                 495

Gly Ala Thr Val Phe Pro Glu Val Gly Ala Ser Val Trp Pro Lys Lys
            500                 505                 510

Gly Thr Ala Val Phe Trp Tyr Asn Leu Phe Ala Ser Gly Glu Gly Asp
        515                 520                 525

Tyr Ser Thr Arg His Ala Ala Cys Pro Val Leu Val Gly Asn Lys Trp
    530                 535                 540

Val Ser Asn Lys Trp Leu His Glu Arg Gly Gln Glu Phe Arg Arg Pro
545                 550                 555                 560

Cys Thr Leu Ser Glu Leu Glu
                565
```

<210> SEQ ID NO 16
<211> LENGTH: 928
<212> TYPE: DNA
<213> ORGANISM: Artificial sequence
<220> FEATURE:
<223> OTHER INFORMATION: Synthetic sequence containing the coding regions of the vacuolar signal sequence of barley gene for Thiol protease aleurain precursor fused to the plant Prolyl 4-hydroxylase Plant and flanking regions

<400> SEQUENCE: 16

```
ctcgagtaaa ccatggctca tgctagggtt ttgcttttgg ctcttgctgt tcttgctact     60

gctgctgttg ctgtggcttc ttcttcatct ttcgctgatt ctaacccaat taggccagtg    120

actgatagag ctgcttctac tcttgctcaa ttggtcgaca tgcttggtat tctttctctt    180

ccaaacgcta acaggaactc ttctaagact aacgatctta ctaacattgt gaggaagtct    240

gagacttctt ctggagatga ggagggaaat ggagaaagat gggtggaagt gatttcttgg    300

gagccaaggg ctgttgttta ccacaacttc cttactaatg aggagtgcga gcaccttatt    360

tctcttgcta agccatctat ggtgaagtct actgtggtgg atgagaaaac tggaggatct    420

aaggattcaa gagtgaggac ttcatctggt actttcctta ggaggggaca tgatgaagtt    480

gtggaagtta ttgagaagag gatttctgat ttcactttca ttccagtgga gaacggagaa    540

ggacttcaag ttcttcacta ccaagtggga caaaagtacg agccacacta cgattacttc    600

cttgatgagt tcaacactaa gaacggagga cagaggattg ctactgtgct tatgtacctt    660
```

```
tctgatgtgg atgatggagg agagactgtt tttccagctg ctaggggaaa catttctgct    720

gttccttggt ggaacgagct ttctaagtgt ggaaaggagg gactttctgt gcttccaaag    780

aaaagggatg ctcttctttt ctggaacatg aggccagatg cttctcttga tccatcttct    840

cttcatggag gatgcccagt tgttaaggga aacaagtggt catctactaa gtggttccac    900

gtgcacgagt tcaaggtgta atgagctc                                       928


<210> SEQ ID NO 17
<211> LENGTH: 302
<212> TYPE: PRT
<213> ORGANISM: Artificial sequence
<220> FEATURE:
<223> OTHER INFORMATION: Synthetic sequence containing the vacuolar
      signal sequence of barley gene for Thiol protease aleurain
      precursor fused to the plant Prolyl 4-hydroxylase Plant and
      flanking regions

<400> SEQUENCE: 17

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala Gln Leu Val
        35                  40                  45

Asp Met Leu Gly Ile Leu Ser Leu Pro Asn Ala Asn Arg Asn Ser Ser
    50                  55                  60

Lys Thr Asn Asp Leu Thr Asn Ile Val Arg Lys Ser Glu Thr Ser Ser
65                  70                  75                  80

Gly Asp Glu Glu Gly Asn Gly Glu Arg Trp Val Glu Val Ile Ser Trp
                85                  90                  95

Glu Pro Arg Ala Val Val Tyr His Asn Phe Leu Thr Asn Glu Glu Cys
            100                 105                 110

Glu His Leu Ile Ser Leu Ala Lys Pro Ser Met Val Lys Ser Thr Val
        115                 120                 125

Val Asp Glu Lys Thr Gly Gly Ser Lys Asp Ser Arg Val Arg Thr Ser
    130                 135                 140

Ser Gly Thr Phe Leu Arg Arg Gly His Asp Glu Val Val Glu Val Ile
145                 150                 155                 160

Glu Lys Arg Ile Ser Asp Phe Thr Phe Ile Pro Val Glu Asn Gly Glu
                165                 170                 175

Gly Leu Gln Val Leu His Tyr Gln Val Gly Gln Lys Tyr Glu Pro His
            180                 185                 190

Tyr Asp Tyr Phe Leu Asp Glu Phe Asn Thr Lys Asn Gly Gly Gln Arg
        195                 200                 205

Ile Ala Thr Val Leu Met Tyr Leu Ser Asp Val Asp Asp Gly Gly Glu
    210                 215                 220

Thr Val Phe Pro Ala Ala Arg Gly Asn Ile Ser Ala Val Pro Trp Trp
225                 230                 235                 240

Asn Glu Leu Ser Lys Cys Gly Lys Glu Gly Leu Ser Val Leu Pro Lys
                245                 250                 255

Lys Arg Asp Ala Leu Leu Phe Trp Asn Met Arg Pro Asp Ala Ser Leu
            260                 265                 270

Asp Pro Ser Ser Leu His Gly Gly Cys Pro Val Val Lys Gly Asn Lys
        275                 280                 285

Trp Ser Ser Thr Lys Trp Phe His Val His Glu Phe Lys Val
```

290 295 300

<210> SEQ ID NO 18
<211> LENGTH: 2689
<212> TYPE: DNA
<213> ORGANISM: Artificial sequence
<220> FEATURE:
<223> OTHER INFORMATION: Synthetic sequence containing the coding regions of the human Procollagen C-proteinase and flanking regions

<400> SEQUENCE: 18
agatctatcg atgcatgcca tggtaccgcg ccatggctca attggctgca acatcaaggc 60
ctgaaagagt ttggccagat ggtgttattc ctttcgttat tggtggaaac tttactggat 120
ctcagagagc agtttttaga caagctatga gacattggga aaagcacact tgtgtgacat 180
tccttgaaag gactgatgaa gattcttata ttgtgttcac ataccgtcca tgtggatgct 240
gctcatatgt tggtagaagg ggaggaggtc cacaagcaat ttctattgga aaaaactgcg 300
ataagttcgg aattgtggtg catgaattgg gacatgttgt tggtttctgg cacgaacaca 360
caaggccaga tagggatagg cacgtgtcta ttgtgaggga aaacattcag ccaggtcaag 420
agtacaattt tcttaagatg gaacctcaag aggtggaatc tctcggagag acttacgact 480
tcgactccat catgcactac gcaaggaata ctttcagcag gggcatcttc ttggatacca 540
ttgtgcctaa gtacgaggtg aacggcgtta agccacctat tggtcaaagg actaggctct 600
ctaagggtga tattgcacag gctaggaagc tctacaaatg tccagcatgc ggagaaactc 660
ttcaggattc cactggcaac ttctcatctc cagagtaccc aaacggatac tctgctcata 720
tgcactgtgt ttggaggatc tcagtgactc ctggagagaa gatcatcctc aacttcactt 780
ccctcgatct ctatcgttct aggctctgtt ggtacgacta tgtggaagtg agagatggct 840
tctggagaaa ggctccactt agaggaaggt tctgcggatc taaacttcct gagccaatcg 900
tgtctactga ttccagattg tgggtggagt tcaggtcctc ttctaattgg gttggcaagg 960 gctttttgc tgtgtacgag gctatttgtg gcggcgacgt gaaaaaggac tacggacata 1020
ttcaaagtcc aaattaccca gatgattacc gtccttcaaa agtgtgtatt tggaggattc 1080
aagtgagtga gggtttccat gttggattga cattccaatc tttcgaaatt gagagacacg 1140
attcatgcgc atacgattat ttggaagtga gagatggaca ctctgaatct tctacactta 1200
ttggaaggta ctgcggttat gagaaacctg atgatattaa gtctacttct agtaggttgt 1260
ggcttaaatt tgtgtcagat ggttctatta acaaggctgg tttcgcagtg aacttcttca 1320
aggaagtgga tgaatgctca agacctaaca gaggaggatg tgagcaaaga tgccttaaca 1380
ctttgggaag ttacaagtgt tcttgcgatc ctggatacga gttggctcct gataagagaa 1440
gatgcgaagc tgcttgcggt ggtttttga caaaattgaa cggatctatt acttctcctg 1500
gatggccaaa agagtaccca cctaataaga attgcatttg gcagcttgtt gcacctactc 1560
agtaccgtat ttcattgcaa ttcgattttt tcgagactga gggtaatgat gtgtgcaagt 1620
acgatttcgt ggaagtgaga tcaggtctta ctgctgatag taaattgcac ggaaagttct 1680
gcggatctga aaaaccagaa gtgattacat cacagtacaa caatatgagg gtggagttca 1740
aatctgataa tactgtttct aaaaaaggtt ttaaggcaca tttcttttct gataaggacg 1800
agtgctctaa agataatggt ggttgccagc aggattgcgt gaacacattc ggttcatatg 1860
agtgccaatg ccgtagtgga tttgttcttc acgataacaa acatgattgc aaagaggcag 1920
gttgcgatca caaggtgaca tctacttcag gtactatcac atctccaaac tggcctgata 1980

```
agtatccttc aaaaaaagaa tgtacatggg caatttcttc tacaccaggt catagggtta   2040

agttgacatt catggagatg gatattgaga gtcaaccaga gtgcgcttat gatcatcttg   2100

aggtgttcga tggaagggat gctaaggctc ctgttcttgg tagattctgt ggtagtaaaa   2160

agccagaacc agtgcttgca acaggatcta ggatgttcct tagattctac tctgataact   2220

cagttcagag gaaaggattc caagctagtc acgcaactga atgcggtgga caagttagag   2280

cagatgttaa gactaaggat ctttactcac acgcacagtt cggagataac aactaccctg   2340

gaggagttga ttgcgagtgg gttattgtgg ctgaagaggg atacggagtt gagcttgttt   2400

tccagacatt cgaggtggag gaggaaactg attgcggtta cgattatatg gaactttttg   2460

atggatacga tagtactgct ccaagacttg gaaggtattg tggtagtggt ccaccagaag   2520

aggtgtactc agctggagat agtgttcttg ttaagttcca cagtgatgat acaattacta   2580

agaagggatt ccatcttaga tatacttcaa ctaagtttca ggatactctt cattctagga   2640

agtaatgagc tcgcggccgc atccaagctt ctgcagacgc gtcgacgtc                2689
```

<210> SEQ ID NO 19
<211> LENGTH: 870
<212> TYPE: PRT
<213> ORGANISM: Artificial sequence
<220> FEATURE:
<223> OTHER INFORMATION: Synthetic sequence containing the human Procollagen C-proteinase and flanking regions

<400> SEQUENCE: 19

```
Met Ala Gln Leu Ala Ala Thr Ser Arg Pro Glu Arg Val Trp Pro Asp
1               5                   10                  15

Gly Val Ile Pro Phe Val Ile Gly Gly Asn Phe Thr Gly Ser Gln Arg
            20                  25                  30

Ala Val Phe Arg Gln Ala Met Arg His Trp Glu Lys His Thr Cys Val
        35                  40                  45

Thr Phe Leu Glu Arg Thr Asp Glu Asp Ser Tyr Ile Val Phe Thr Tyr
    50                  55                  60

Arg Pro Cys Gly Cys Cys Ser Tyr Val Gly Arg Arg Gly Gly Gly Pro
65                  70                  75                  80

Gln Ala Ile Ser Ile Gly Lys Asn Cys Asp Lys Phe Gly Ile Val Val
                85                  90                  95

His Glu Leu Gly His Val Val Gly Phe Trp His Glu His Thr Arg Pro
            100                 105                 110

Asp Arg Asp Arg His Val Ser Ile Val Arg Glu Asn Ile Gln Pro Gly
        115                 120                 125

Gln Glu Tyr Asn Phe Leu Lys Met Glu Pro Gln Glu Val Glu Ser Leu
    130                 135                 140

Gly Glu Thr Tyr Asp Phe Asp Ser Ile Met His Tyr Ala Arg Asn Thr
145                 150                 155                 160

Phe Ser Arg Gly Ile Phe Leu Asp Thr Ile Val Pro Lys Tyr Glu Val
                165                 170                 175

Asn Gly Val Lys Pro Pro Ile Gly Gln Arg Thr Arg Leu Ser Lys Gly
            180                 185                 190

Asp Ile Ala Gln Ala Arg Lys Leu Tyr Lys Cys Pro Ala Cys Gly Glu
        195                 200                 205

Thr Leu Gln Asp Ser Thr Gly Asn Phe Ser Ser Pro Glu Tyr Pro Asn
    210                 215                 220

Gly Tyr Ser Ala His Met His Cys Val Trp Arg Ile Ser Val Thr Pro
225                 230                 235                 240
```

```
Gly Glu Lys Ile Ile Leu Asn Phe Thr Ser Leu Asp Leu Tyr Arg Ser
                245                 250                 255

Arg Leu Cys Trp Tyr Asp Tyr Val Glu Val Arg Asp Gly Phe Trp Arg
            260                 265                 270

Lys Ala Pro Leu Arg Gly Arg Phe Cys Gly Ser Lys Leu Pro Glu Pro
        275                 280                 285

Ile Val Ser Thr Asp Ser Arg Leu Trp Val Glu Phe Arg Ser Ser Ser
    290                 295                 300

Asn Trp Val Gly Lys Gly Phe Phe Ala Val Tyr Glu Ala Ile Cys Gly
305                 310                 315                 320

Gly Asp Val Lys Lys Asp Tyr Gly His Ile Gln Ser Pro Asn Tyr Pro
                325                 330                 335

Asp Asp Tyr Arg Pro Ser Lys Val Cys Ile Trp Arg Ile Gln Val Ser
            340                 345                 350

Glu Gly Phe His Val Gly Leu Thr Phe Gln Ser Phe Glu Ile Glu Arg
        355                 360                 365

His Asp Ser Cys Ala Tyr Asp Tyr Leu Glu Val Arg Asp Gly His Ser
    370                 375                 380

Glu Ser Ser Thr Leu Ile Gly Arg Tyr Cys Gly Tyr Glu Lys Pro Asp
385                 390                 395                 400

Asp Ile Lys Ser Thr Ser Ser Arg Leu Trp Leu Lys Phe Val Ser Asp
                405                 410                 415

Gly Ser Ile Asn Lys Ala Gly Phe Ala Val Asn Phe Phe Lys Glu Val
            420                 425                 430

Asp Glu Cys Ser Arg Pro Asn Arg Gly Gly Cys Glu Gln Arg Cys Leu
        435                 440                 445

Asn Thr Leu Gly Ser Tyr Lys Cys Ser Cys Asp Pro Gly Tyr Glu Leu
    450                 455                 460

Ala Pro Asp Lys Arg Arg Cys Glu Ala Ala Cys Gly Gly Phe Leu Thr
465                 470                 475                 480

Lys Leu Asn Gly Ser Ile Thr Ser Pro Gly Trp Pro Lys Glu Tyr Pro
                485                 490                 495

Pro Asn Lys Asn Cys Ile Trp Gln Leu Val Ala Pro Thr Gln Tyr Arg
            500                 505                 510

Ile Ser Leu Gln Phe Asp Phe Phe Glu Thr Glu Gly Asn Asp Val Cys
        515                 520                 525

Lys Tyr Asp Phe Val Glu Val Arg Ser Gly Leu Thr Ala Asp Ser Lys
    530                 535                 540

Leu His Gly Lys Phe Cys Gly Ser Glu Lys Pro Glu Val Ile Thr Ser
545                 550                 555                 560

Gln Tyr Asn Asn Met Arg Val Glu Phe Lys Ser Asp Asn Thr Val Ser
                565                 570                 575

Lys Lys Gly Phe Lys Ala His Phe Phe Ser Asp Lys Asp Glu Cys Ser
            580                 585                 590

Lys Asp Asn Gly Gly Cys Gln Gln Asp Cys Val Asn Thr Phe Gly Ser
        595                 600                 605

Tyr Glu Cys Gln Cys Arg Ser Gly Phe Val Leu His Asp Asn Lys His
    610                 615                 620

Asp Cys Lys Glu Ala Gly Cys Asp His Lys Val Thr Ser Thr Ser Gly
625                 630                 635                 640

Thr Ile Thr Ser Pro Asn Trp Pro Asp Lys Tyr Pro Ser Lys Lys Glu
                645                 650                 655
```

```
Cys Thr Trp Ala Ile Ser Ser Thr Pro Gly His Arg Val Lys Leu Thr
            660                 665                 670

Phe Met Glu Met Asp Ile Glu Ser Gln Pro Glu Cys Ala Tyr Asp His
        675                 680                 685

Leu Glu Val Phe Asp Gly Arg Asp Ala Lys Ala Pro Val Leu Gly Arg
    690                 695                 700

Phe Cys Gly Ser Lys Lys Pro Glu Pro Val Leu Ala Thr Gly Ser Arg
705                 710                 715                 720

Met Phe Leu Arg Phe Tyr Ser Asp Asn Ser Val Gln Arg Lys Gly Phe
                725                 730                 735

Gln Ala Ser His Ala Thr Glu Cys Gly Gly Gln Val Arg Ala Asp Val
            740                 745                 750

Lys Thr Lys Asp Leu Tyr Ser His Ala Gln Phe Gly Asp Asn Asn Tyr
        755                 760                 765

Pro Gly Gly Val Asp Cys Glu Trp Val Ile Val Ala Glu Glu Gly Tyr
    770                 775                 780

Gly Val Glu Leu Val Phe Gln Thr Phe Glu Val Glu Glu Glu Thr Asp
785                 790                 795                 800

Cys Gly Tyr Asp Tyr Met Glu Leu Phe Asp Gly Tyr Asp Ser Thr Ala
                805                 810                 815

Pro Arg Leu Gly Arg Tyr Cys Gly Ser Gly Pro Pro Glu Glu Val Tyr
            820                 825                 830

Ser Ala Gly Asp Ser Val Leu Val Lys Phe His Ser Asp Asp Thr Ile
        835                 840                 845

Thr Lys Lys Gly Phe His Leu Arg Tyr Thr Ser Thr Lys Phe Gln Asp
    850                 855                 860

Thr Leu His Ser Arg Lys
865                 870


<210> SEQ ID NO 20
<211> LENGTH: 2912
<212> TYPE: DNA
<213> ORGANISM: Artificial sequence
<220> FEATURE:
<223> OTHER INFORMATION: Synthetic sequence containing the coding
      regions of the human Procollagen I N-proteinase and flanking
      regions

<400> SEQUENCE: 20

gcgccatggc tcaattgagg agaagggcta ggagacacgc agctgatgat gattacaaca      60

ttgaagtttt gcttggtgtt gatgatagtg tggtgcaatt ccacggaaaa gagcatgttc     120

agaaatatct tttgacactt atgaatattg tgaacgaaat ctaccatgat gagtctttgg     180

gagcacacat taacgtggtt cttgtgagga ttattcttct ttcatacggt aaatctatgt     240

cacttattga gattggaaac ccttctcagt ctcttgagaa tgtgtgcaga tgggcatacc     300

ttcaacagaa gcctgatact ggacacgatg agtatcacga tcacgctatt ttccttacaa     360

ggcaggattt cggtccaagt ggaatgcaag gatatgctcc tgttactggt atgtgccacc     420

ctgttaggtc ttgtacactt aaccacgagg atggtttttc atctgctttc gtggtggctc     480

atgagacagg tcatgttttg ggaatggaac atgatggaca gggtaataga tgtggagatg     540

aagtgagact tggttcaatt atggctcctc ttgttcaagc tgcttttcat aggttccact     600

ggagtaggtg ttcacagcaa gagttgagta gataccttca ttcttacgat tgcttgcttg     660

atgatccatt tgctcatgat tggccagctt tgcctcaact tcctggattg cactactcta     720

tgaacgagca gtgcagattt gatttcggtc ttggttacat gatgtgcaca gctttcagga     780
```

```
ctttcgatcc atgcaaacag ttgtggtgtt cacacccaga taacccatat ttctgtaaaa    840

caaaaaaagg tccaccactt gatggtacta tgtgcgcacc tggaaagcac tgcttcaagg    900

gacactgcat ttggcttact cctgatattc ttaaaaggga tggatcatgg ggagcttggt    960

ctccattcgg aagttgctca agaacttgcg gaacaggtgt taagtttaga actaggcagt   1020

gcgataatcc acaccctgct aatggtggta gaacttgctc tggacttgct tacgattttc   1080

agttgtgttc taggcaagat tgccctgata gtcttgctga ttttagagaa gagcaatgta   1140

gacagtggga tctttacttt gagcacggcg acgctcagca ccactggctt ccacacgagc   1200

atagagatgc aaaagaaagg tgtcaccttt attgcgagag tagagagact ggagaggtgg   1260

tgtcaatgaa gagaatggtg cacgatggta caaggtgttc ttataaggat gcattctctt   1320

tgtgtgtgag gggagattgc aggaaagtgg gttgtgatgg agtgattgga tctagtaagc   1380

aagaagataa gtgcggagtg tgcggaggag ataactctca ttgcaaggtt gtgaaaggaa   1440

cttttacaag atcaccaaaa aaacacggtt acattaagat gttcgaaatt cctgctggag   1500

caaggcattt gcttattcag gaagtggatg caacatctca ccacttggca gtgaaaaacc   1560

ttgagactgg aaaattcatt ttgaacgagg agaacgatgt tgatgcatct agtaagactt   1620

tcattgcaat gggtgttgaa tgggagtata gggatgagga tggaagggaa acacttcaaa   1680

caatgggtcc tcttcatgga acaattactg tgttggtgat tccagtggga gatacaaggg   1740

tgtcattgac atacaagtat atgattcacg aggatagtct taacgttgat gataacaacg   1800

ttttggaaga agattctgtg gtttacgagt gggctcttaa gaaatggtca ccttgctcta   1860

agccatgtgg tggaggaagt cagttcacta agtatggttg taggaggagg cttgatcata   1920

agatggttca taggggattt tgcgcagcac ttagtaagcc aaaggcaatt aggagggctt   1980

gtaaccctca agaatgctca caaccagttt gggtgacagg agagtgggag ccatgttcac   2040

aaacatgcgg aagaactgga atgcaagtta gatcagttag atgcattcaa cctcttcatg   2100

ataacactac aagaagtgtg cacgcaaaac actgtaacga tgctaggcca gagagtagaa   2160

gagcttgctc tagggaactt tgccctggta gatggagggc aggaccttgg agtcagtgct   2220

ctgtgacatg tggaaacggt actcaggaaa gacctgttcc atgtagaact gctgatgata   2280

gtttcggaat ttgtcaggag gaaaggccag aaacagctag gacttgtaga cttggacctt   2340

gtcctaggaa tatttctgat cctagtaaaa aatcatacgt ggtgcaatgg ttgagtaggc   2400

cagatccaga ttcaccaatt aggaagattt cttcaaaagg acactgccag ggtgataaga   2460

gtattttctg cagaatggaa gttcttagta ggtactgttc tattccaggt tataacaaac   2520

tttcttgtaa gagttgcaac ttgtataaca atcttactaa cgtggagggt agaattgaac   2580

ctccaccagg aaagcacaac gatattgatg tgtttatgcc tactcttcct gtgccaacag   2640

ttgcaatgga agttagacct tctccatcta ctccacttga ggtgccactt aatgcatcaa   2700

gtactaacgc tactgaggat cacccagaga ctaacgcagt tgatgagcct tataagattc   2760

acggacttga ggatgaggtt cagccaccaa accttattcc taggaggcca agtccttacg   2820

aaaaaactag aaatcagagg attcaggagc ttattgatga gatgaggaaa aaggagatgc   2880

ttggaaagtt ctaatgagct cgcggccgca tc                                 2912
```

<210> SEQ ID NO 21
<211> LENGTH: 962
<212> TYPE: PRT
<213> ORGANISM: Artificial sequence
<220> FEATURE:

<223> OTHER INFORMATION: Synthetic sequence containing the human Procollagen I N-proteinase and flanking regions

<400> SEQUENCE: 21

```
Met Ala Gln Leu Arg Arg Arg Ala Arg Arg His Ala Ala Asp Asp Asp
1               5                   10                  15

Tyr Asn Ile Glu Val Leu Leu Gly Val Asp Asp Ser Val Val Gln Phe
            20                  25                  30

His Gly Lys Glu His Val Gln Lys Tyr Leu Leu Thr Leu Met Asn Ile
        35                  40                  45

Val Asn Glu Ile Tyr His Asp Glu Ser Leu Gly Ala His Ile Asn Val
    50                  55                  60

Val Leu Val Arg Ile Ile Leu Leu Ser Tyr Gly Lys Ser Met Ser Leu
65                  70                  75                  80

Ile Glu Ile Gly Asn Pro Ser Gln Ser Leu Glu Asn Val Cys Arg Trp
                85                  90                  95

Ala Tyr Leu Gln Gln Lys Pro Asp Thr Gly His Asp Glu Tyr His Asp
            100                 105                 110

His Ala Ile Phe Leu Thr Arg Gln Asp Phe Gly Pro Ser Gly Met Gln
        115                 120                 125

Gly Tyr Ala Pro Val Thr Gly Met Cys His Pro Val Arg Ser Cys Thr
    130                 135                 140

Leu Asn His Glu Asp Gly Phe Ser Ser Ala Phe Val Val Ala His Glu
145                 150                 155                 160

Thr Gly His Val Leu Gly Met Glu His Asp Gly Gln Gly Asn Arg Cys
                165                 170                 175

Gly Asp Glu Val Arg Leu Gly Ser Ile Met Ala Pro Leu Val Gln Ala
            180                 185                 190

Ala Phe His Arg Phe His Trp Ser Arg Cys Ser Gln Gln Glu Leu Ser
        195                 200                 205

Arg Tyr Leu His Ser Tyr Asp Cys Leu Leu Asp Asp Pro Phe Ala His
    210                 215                 220

Asp Trp Pro Ala Leu Pro Gln Leu Pro Gly Leu His Tyr Ser Met Asn
225                 230                 235                 240

Glu Gln Cys Arg Phe Asp Phe Gly Leu Gly Tyr Met Met Cys Thr Ala
                245                 250                 255

Phe Arg Thr Phe Asp Pro Cys Lys Gln Leu Trp Cys Ser His Pro Asp
            260                 265                 270

Asn Pro Tyr Phe Cys Lys Thr Lys Lys Gly Pro Pro Leu Asp Gly Thr
        275                 280                 285

Met Cys Ala Pro Gly Lys His Cys Phe Lys Gly His Cys Ile Trp Leu
    290                 295                 300

Thr Pro Asp Ile Leu Lys Arg Asp Gly Ser Trp Gly Ala Trp Ser Pro
305                 310                 315                 320

Phe Gly Ser Cys Ser Arg Thr Cys Gly Thr Gly Val Lys Phe Arg Thr
                325                 330                 335

Arg Gln Cys Asp Asn Pro His Pro Ala Asn Gly Gly Arg Thr Cys Ser
            340                 345                 350

Gly Leu Ala Tyr Asp Phe Gln Leu Cys Ser Arg Gln Asp Cys Pro Asp
        355                 360                 365

Ser Leu Ala Asp Phe Arg Glu Glu Gln Cys Arg Gln Trp Asp Leu Tyr
    370                 375                 380

Phe Glu His Gly Asp Ala Gln His His Trp Leu Pro His Glu His Arg
385                 390                 395                 400
```

```
Asp Ala Lys Glu Arg Cys His Leu Tyr Cys Glu Ser Arg Glu Thr Gly
                405                 410                 415

Glu Val Val Ser Met Lys Arg Met Val His Asp Gly Thr Arg Cys Ser
            420                 425                 430

Tyr Lys Asp Ala Phe Ser Leu Cys Val Arg Gly Asp Cys Arg Lys Val
        435                 440                 445

Gly Cys Asp Gly Val Ile Gly Ser Ser Lys Gln Glu Asp Lys Cys Gly
    450                 455                 460

Val Cys Gly Gly Asp Asn Ser His Cys Lys Val Val Lys Gly Thr Phe
465                 470                 475                 480

Thr Arg Ser Pro Lys Lys His Gly Tyr Ile Lys Met Phe Glu Ile Pro
                485                 490                 495

Ala Gly Ala Arg His Leu Leu Ile Gln Glu Val Asp Ala Thr Ser His
            500                 505                 510

His Leu Ala Val Lys Asn Leu Glu Thr Gly Lys Phe Ile Leu Asn Glu
        515                 520                 525

Glu Asn Asp Val Asp Ala Ser Ser Lys Thr Phe Ile Ala Met Gly Val
    530                 535                 540

Glu Trp Glu Tyr Arg Asp Glu Asp Gly Arg Glu Thr Leu Gln Thr Met
545                 550                 555                 560

Gly Pro Leu His Gly Thr Ile Thr Val Leu Val Ile Pro Val Gly Asp
                565                 570                 575

Thr Arg Val Ser Leu Thr Tyr Lys Tyr Met Ile His Glu Asp Ser Leu
            580                 585                 590

Asn Val Asp Asp Asn Asn Val Leu Glu Glu Asp Ser Val Val Tyr Glu
        595                 600                 605

Trp Ala Leu Lys Lys Trp Ser Pro Cys Ser Lys Pro Cys Gly Gly Gly
    610                 615                 620

Ser Gln Phe Thr Lys Tyr Gly Cys Arg Arg Arg Leu Asp His Lys Met
625                 630                 635                 640

Val His Arg Gly Phe Cys Ala Ala Leu Ser Lys Pro Lys Ala Ile Arg
                645                 650                 655

Arg Ala Cys Asn Pro Gln Glu Cys Ser Gln Pro Val Trp Val Thr Gly
            660                 665                 670

Glu Trp Glu Pro Cys Ser Gln Thr Cys Gly Arg Thr Gly Met Gln Val
        675                 680                 685

Arg Ser Val Arg Cys Ile Gln Pro Leu His Asp Asn Thr Thr Arg Ser
    690                 695                 700

Val His Ala Lys His Cys Asn Asp Ala Arg Pro Glu Ser Arg Arg Ala
705                 710                 715                 720

Cys Ser Arg Glu Leu Cys Pro Gly Arg Trp Arg Ala Gly Pro Trp Ser
                725                 730                 735

Gln Cys Ser Val Thr Cys Gly Asn Gly Thr Gln Glu Arg Pro Val Pro
            740                 745                 750

Cys Arg Thr Ala Asp Asp Ser Phe Gly Ile Cys Gln Glu Glu Arg Pro
        755                 760                 765

Glu Thr Ala Arg Thr Cys Arg Leu Gly Pro Cys Pro Arg Asn Ile Ser
    770                 775                 780

Asp Pro Ser Lys Lys Ser Tyr Val Val Gln Trp Leu Ser Arg Pro Asp
785                 790                 795                 800

Pro Asp Ser Pro Ile Arg Lys Ile Ser Ser Lys Gly His Cys Gln Gly
                805                 810                 815
```

```
Asp Lys Ser Ile Phe Cys Arg Met Glu Val Leu Ser Arg Tyr Cys Ser
            820                 825                 830

Ile Pro Gly Tyr Asn Lys Leu Ser Cys Lys Ser Cys Asn Leu Tyr Asn
        835                 840                 845

Asn Leu Thr Asn Val Glu Gly Arg Ile Glu Pro Pro Gly Lys His
    850                 855                 860

Asn Asp Ile Asp Val Phe Met Pro Thr Leu Pro Val Pro Thr Val Ala
865                 870                 875                 880

Met Glu Val Arg Pro Ser Pro Ser Thr Pro Leu Glu Val Pro Leu Asn
                885                 890                 895

Ala Ser Ser Thr Asn Ala Thr Glu Asp His Pro Glu Thr Asn Ala Val
            900                 905                 910

Asp Glu Pro Tyr Lys Ile His Gly Leu Glu Asp Glu Val Gln Pro Pro
        915                 920                 925

Asn Leu Ile Pro Arg Arg Pro Ser Pro Tyr Glu Lys Thr Arg Asn Gln
    930                 935                 940

Arg Ile Gln Glu Leu Ile Asp Glu Met Arg Lys Lys Glu Met Leu Gly
945                 950                 955                 960

Lys Phe


<210> SEQ ID NO 22
<211> LENGTH: 2888
<212> TYPE: DNA
<213> ORGANISM: Artificial sequence
<220> FEATURE:
<223> OTHER INFORMATION: Synthetic sequence containing the coding
      regions of the vacuolar signal sequence of barley gene for Thiol
      protease aleurain precursor fused to the human Lysyl hydroxylase 3
      and flanking regions

<400> SEQUENCE: 22

gcgaattcgc tagctatcac tgaaaagaca gcaagacaat ggtgtctcga tgcaccagaa     60

ccacatcttt gcagcagatg tgaagcagcc agagtggtcc acaagacgca ctcagaaaag    120

gcatcttcta ccgacacaga aaaagacaac cacagctcat catccaacat gtagactgtc    180

gttatgcgtc ggctgaagat aagactgacc ccaggccagc actaaagaag aaataatgca    240

agtggtccta gctccacttt agctttaata attatgtttc attattattc tctgcttttg    300

ctctctatat aaagagcttg tattttcatt tgaaggcaga ggcgaacaca cacacagaac    360

ctccctgctt acaaaccaga tcttaaacca tggctcacgc tagggttttg cttcttgctc    420

ttgctgttct tgctactgct gctgttgctg tggcttcttc aagttctttc gctgattcta    480

acccaattag gccagtgact gatagagctg cttctactct tgctcaattg agatctatgt    540

ctgatagacc aaggggaagg gatccagtta atccagagaa gttgcttgtg attactgtgg    600

ctactgctga gactgaagga taccttagat tccttaggag tgctgagttc ttcaactaca    660

ctgtgaggac tcttggactt ggagaagaat ggaggggagg agatgttgct agaactgttg    720

gaggaggaca gaaagtgaga tggcttaaga aagagatgga gaagtacgct gatagggagg    780

atatgattat tatgttcgtg gattcttacg atgtgattct tgctggatct ccaactgagc    840

ttttgaagaa attcgttcag tctggatcta ggcttctttt ctctgctgag tctttttgtt    900

ggccagaatg ggacttgct gagcaatatc cagaagtggg aactggaaag agattcctta    960

actctggagg attcattgga ttcgctacta ctattcacca gattgtgagg cagtggaagt   1020

acaaggatga cgatgatgat cagcttttct acactaggct ttaccttgat ccaggactta   1080

gggagaagtt gtctcttaac cttgatcaca agtctaggat tttccagaac cttaacggtg   1140
```

```
ctcttgatga ggttgtgctt aagttcgata ggaacagagt gaggattagg aacgtggctt   1200

acgatactct tcctattgtg gtgcatggaa acggaccaac aaaactccag cttaactacc   1260

ttggaaacta cgttccaaac ggatggactc cagaaggagg atgtggattc tgcaatcagg   1320

ataggagaac tcttccagga ggacaaccac caccaagagt tttccttgct gtgttcgttg   1380

aacagccaac tccattcctt ccaagattcc ttcagaggct tcttcttttg gattacccac   1440

cagatagggt gacacttttc cttcacaaca acgaggtttt ccacgagcca cacattgctg   1500

attcttggcc acagcttcag gatcatttct ctgctgtgaa gttggttggt ccagaagaag   1560

ctctttctcc aggagaagct agggatatgg ctatggattt gtgcaggcag gatccagagt   1620

gcgagttcta cttctctctt gatgctgatg ctgtgcttac taaccttcag actcttagga   1680

ttcttattga ggagaacagg aaagtgattg ctccaatgct ttctaggcac ggaaagttgt   1740

ggtctaattt ctggggtgct ctttctcctg atgagtacta cgctagatca gaggactacg   1800

tggagcttgt tcagagaaag agagtgggag tttggaacgt tccttatatt tctcaggctt   1860

acgtgattag ggagatact cttaggatgg agcttccaca gagggatgtt ttctctggat   1920

ctgatactga tccagatatg gctttctgca agtctttcag ggataaggga attttccttc   1980

acctttctaa ccagcatgag ttcggaagat tgcttgctac ttcaagatac gatactgagc   2040

accttcatcc tgatctttgg cagattttcg ataacccagt ggattggaag gagcagtaca   2100

ttcacgagaa ctactctagg gctcttgaag gagaaggaat tgtggagcaa ccatgcccag   2160

atgtttactg gttcccactt ctttctgagc aaatgtgcga tgagcttgtt gctgagatgg   2220

agcattacgg acaatggagt ggaggtagac atgaggattc taggcttgct ggaggatacg   2280

agaacgttcc aactgtggat attcacatga agcaagtggg atacgaggat caatggcttc   2340

agcttcttag gacttatgtg ggaccaatga ctgagtctct ttcccagga taccacacta   2400

aggctagggc tgttatgaac ttcgttgtga ggtatcgtcc agatgagcaa ccatctctta   2460

ggccacacca cgattcttct actttcactc ttaacgtggc tcttaaccac aagggacttg   2520

attatgaggg aggaggatgc cgtttcctta gatacgattg cgtgatttct tcaccaagaa   2580

agggatgggc tcttcttcat ccaggaaggc ttactcatta ccacgaggga cttccaacta   2640

cttggggaac tagatatatt atggtgtctt tcgtggatcc atgactgctt taatgagata   2700

tgcgagacgc ctatgatcgc atgatatttg ctttcaattc tgttgtgcac gttgtaaaaa   2760

acctgagcat gtgtagctca gatccttacc gccggtttcg gttcattcta atgaatatat   2820

cacccgttac tatcgtattt ttatgaataa tattctccgt tcaatttact gattgtccag   2880

aattcgcg                                                             2888
```

<210> SEQ ID NO 23
<211> LENGTH: 764
<212> TYPE: PRT
<213> ORGANISM: Artificial sequence
<220> FEATURE:
<223> OTHER INFORMATION: Synthetic sequence containing the vacuolar signal sequence of barley gene for Thiol protease aleurain precursor fused to the human Lysyl hydroxylase 3 and flanking regions

<400> SEQUENCE: 23

```
Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30
```

```
Ile Arg Pro Val Thr Asp Arg Ala Ala Ser Thr Leu Ala Gln Leu Arg
        35                  40                  45

Ser Met Ser Asp Arg Pro Arg Gly Arg Asp Pro Val Asn Pro Glu Lys
    50                  55                  60

Leu Leu Val Ile Thr Val Ala Thr Ala Glu Thr Glu Gly Tyr Leu Arg
65                  70                  75                  80

Phe Leu Arg Ser Ala Glu Phe Phe Asn Tyr Thr Val Arg Thr Leu Gly
                85                  90                  95

Leu Gly Glu Glu Trp Arg Gly Gly Asp Val Ala Arg Thr Val Gly Gly
            100                 105                 110

Gly Gln Lys Val Arg Trp Leu Lys Lys Glu Met Glu Lys Tyr Ala Asp
        115                 120                 125

Arg Glu Asp Met Ile Ile Met Phe Val Asp Ser Tyr Asp Val Ile Leu
    130                 135                 140

Ala Gly Ser Pro Thr Glu Leu Leu Lys Lys Phe Val Gln Ser Gly Ser
145                 150                 155                 160

Arg Leu Leu Phe Ser Ala Glu Ser Phe Cys Trp Pro Glu Trp Gly Leu
                165                 170                 175

Ala Glu Gln Tyr Pro Glu Val Gly Thr Gly Lys Arg Phe Leu Asn Ser
            180                 185                 190

Gly Gly Phe Ile Gly Phe Ala Thr Thr Ile His Gln Ile Val Arg Gln
        195                 200                 205

Trp Lys Tyr Lys Asp Asp Asp Asp Asp Gln Leu Phe Tyr Thr Arg Leu
    210                 215                 220

Tyr Leu Asp Pro Gly Leu Arg Glu Lys Leu Ser Leu Asn Leu Asp His
225                 230                 235                 240

Lys Ser Arg Ile Phe Gln Asn Leu Asn Gly Ala Leu Asp Glu Val Val
                245                 250                 255

Leu Lys Phe Asp Arg Asn Arg Val Arg Ile Arg Asn Val Ala Tyr Asp
            260                 265                 270

Thr Leu Pro Ile Val Val His Gly Asn Gly Pro Thr Lys Leu Gln Leu
        275                 280                 285

Asn Tyr Leu Gly Asn Tyr Val Pro Asn Gly Trp Thr Pro Glu Gly Gly
    290                 295                 300

Cys Gly Phe Cys Asn Gln Asp Arg Arg Thr Leu Pro Gly Gly Gln Pro
305                 310                 315                 320

Pro Pro Arg Val Phe Leu Ala Val Phe Val Glu Gln Pro Thr Pro Phe
                325                 330                 335

Leu Pro Arg Phe Leu Gln Arg Leu Leu Leu Leu Asp Tyr Pro Pro Asp
            340                 345                 350

Arg Val Thr Leu Phe Leu His Asn Asn Glu Val Phe His Glu Pro His
        355                 360                 365

Ile Ala Asp Ser Trp Pro Gln Leu Gln Asp His Phe Ser Ala Val Lys
    370                 375                 380

Leu Val Gly Pro Glu Glu Ala Leu Ser Pro Gly Glu Ala Arg Asp Met
385                 390                 395                 400

Ala Met Asp Leu Cys Arg Gln Asp Pro Glu Cys Glu Phe Tyr Phe Ser
                405                 410                 415

Leu Asp Ala Asp Ala Val Leu Thr Asn Leu Gln Thr Leu Arg Ile Leu
            420                 425                 430

Ile Glu Glu Asn Arg Lys Val Ile Ala Pro Met Leu Ser Arg His Gly
        435                 440                 445
```

```
Lys Leu Trp Ser Asn Phe Trp Gly Ala Leu Ser Pro Asp Glu Tyr Tyr
    450                 455                 460

Ala Arg Ser Glu Asp Tyr Val Glu Leu Val Gln Arg Lys Arg Val Gly
465                 470                 475                 480

Val Trp Asn Val Pro Tyr Ile Ser Gln Ala Tyr Val Ile Arg Gly Asp
                485                 490                 495

Thr Leu Arg Met Glu Leu Pro Gln Arg Asp Val Phe Ser Gly Ser Asp
            500                 505                 510

Thr Asp Pro Asp Met Ala Phe Cys Lys Ser Phe Arg Asp Lys Gly Ile
        515                 520                 525

Phe Leu His Leu Ser Asn Gln His Glu Phe Gly Arg Leu Leu Ala Thr
    530                 535                 540

Ser Arg Tyr Asp Thr Glu His Leu His Pro Asp Leu Trp Gln Ile Phe
545                 550                 555                 560

Asp Asn Pro Val Asp Trp Lys Glu Gln Tyr Ile His Glu Asn Tyr Ser
                565                 570                 575

Arg Ala Leu Glu Gly Glu Gly Ile Val Glu Gln Pro Cys Pro Asp Val
            580                 585                 590

Tyr Trp Phe Pro Leu Leu Ser Glu Gln Met Cys Asp Glu Leu Val Ala
        595                 600                 605

Glu Met Glu His Tyr Gly Gln Trp Ser Gly Gly Arg His Glu Asp Ser
    610                 615                 620

Arg Leu Ala Gly Gly Tyr Glu Asn Val Pro Thr Val Asp Ile His Met
625                 630                 635                 640

Lys Gln Val Gly Tyr Glu Asp Gln Trp Leu Gln Leu Leu Arg Thr Tyr
                645                 650                 655

Val Gly Pro Met Thr Glu Ser Leu Phe Pro Gly Tyr His Thr Lys Ala
            660                 665                 670

Arg Ala Val Met Asn Phe Val Val Arg Tyr Arg Pro Asp Glu Gln Pro
        675                 680                 685

Ser Leu Arg Pro His His Asp Ser Ser Thr Phe Thr Leu Asn Val Ala
    690                 695                 700

Leu Asn His Lys Gly Leu Asp Tyr Glu Gly Gly Gly Cys Arg Phe Leu
705                 710                 715                 720

Arg Tyr Asp Cys Val Ile Ser Ser Pro Arg Lys Gly Trp Ala Leu Leu
                725                 730                 735

His Pro Gly Arg Leu Thr His Tyr His Glu Gly Leu Pro Thr Thr Trp
            740                 745                 750

Gly Thr Arg Tyr Ile Met Val Ser Phe Val Asp Pro
        755                 760


<210> SEQ ID NO 24
<211> LENGTH: 45
<212> TYPE: PRT
<213> ORGANISM: Artificial sequence
<220> FEATURE:
<223> OTHER INFORMATION: Vacuole signal sequence of barley gene for
      Thiol protease aleurain precursor

<400> SEQUENCE: 24

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala
        35                  40                  45
```

```
<210> SEQ ID NO 25
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 25

atcaccagga gaacagggac catc                                              24


<210> SEQ ID NO 26
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 26

tccacttcca aatctctatc cctaacaac                                         29


<210> SEQ ID NO 27
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 27

aggcattaga ggcgataagg gag                                               23


<210> SEQ ID NO 28
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 28

tcaatccaat aatagccact tgaccac                                           27


<210> SEQ ID NO 29
<211> LENGTH: 102
<212> TYPE: DNA
<213> ORGANISM: Artificial sequence
<220> FEATURE:
<223> OTHER INFORMATION: pBINPLUS multiple cloning site

<400> SEQUENCE: 29

atgaccatga ttacgccaag ctggcgcgcc aagcttgcat gcctgcaggt cgactctaga       60

ggatccccgg gtaccgagct cgaattctta attaacaatt ca                         102
```